United States Patent [19]
Jaszai

[11] Patent Number: 5,402,892
[45] Date of Patent: Apr. 4, 1995

[54] IMPACT RESISTANT WRAPPING SYSTEM

[75] Inventor: Zoltan K. Jaszai, Tokyo, Japan

[73] Assignee: Burlington Consolidated Limited Incorporation, Dublin, Ireland

[21] Appl. No.: 113,660

[22] Filed: Aug. 31, 1993

[30] Foreign Application Priority Data

Aug. 31, 1992 [JP] Japan .................................. 4-232312
Sep. 24, 1992 [JP] Japan .................................. 4-255098
Jan. 12, 1993 [JP] Japan .................................. 5-003638

[51] Int. Cl.⁶ ............................................. B65D 81/14
[52] U.S. Cl. ................................. 206/522; 206/523; 206/524.8; 137/223
[58] Field of Search ............... 206/446, 521, 522, 523, 206/524, 524.8; 137/223, 230; 229/87.02; 383/86, 87

[56] References Cited

U.S. PATENT DOCUMENTS

| | | | |
|---|---|---|---|
| 3,412,521 | 11/1968 | Bauman | 206/523 |
| 4,155,453 | 5/1979 | Ono | 206/522 |
| 4,193,499 | 3/1980 | Lookholder | 206/524 |
| 4,262,801 | 4/1981 | Avery | 206/522 |
| 4,295,566 | 10/1981 | Vincek | 206/524.8 |
| 4,620,633 | 11/1986 | Lookholder | 206/523 |
| 4,924,899 | 5/1990 | Po | 137/232 |
| 5,009,318 | 4/1991 | Lepinoy | 206/522 |
| 5,042,663 | 8/1991 | Heinrich | |
| 5,129,519 | 7/1992 | David et al. | 206/523 |

FOREIGN PATENT DOCUMENTS

| | | |
|---|---|---|
| 0434447 | 6/1991 | European Pat. Off. . |
| 51-93720 | 7/1976 | Japan . |
| 2184997 | 7/1987 | United Kingdom . |
| 2230509 | 10/1990 | United Kingdom ................ 206/522 |
| 87/02012 | 4/1987 | WIPO . |

Primary Examiner—Jimmy G. Foster
Attorney, Agent, or Firm—Wenderoth, Lind & Ponack

[57] ABSTRACT

An impact resistant wrapping system for packaging fragile articles is formed in a sheet by sealing, under pressure, two single or multi-layer or laminated flexible membranes having gas or air barrier properties, with cushioning-cellular material such as sponge foam confined in a single airtight cavity defined between the membranes. The wrapping system is in a flat state in which the cushioning-cellular material is constricted in the cavity. In use, the sheet-like wrapping system is wound or folded around the article and is retained in its wrapping state with fastening members. Air is introduced into the cavity by opening an air valve or puncturing the wrapping system at any surface point thereof, so as to allow the cushioning-cellular material to expand and force the inner of the membranes against the article, whereby the article can be securely protected from shock and damage. After use, by removing air from the cavity formed between the outer and inner membranes through the air valve to constrict the cushioning-cellular material, and closing the air valve or applying an adhesive treated surface patch to maintain the compressed state of the cushioning-cellular material in the cavity, the wrapping system can be reused.

18 Claims, 62 Drawing Sheets

F I G. 31
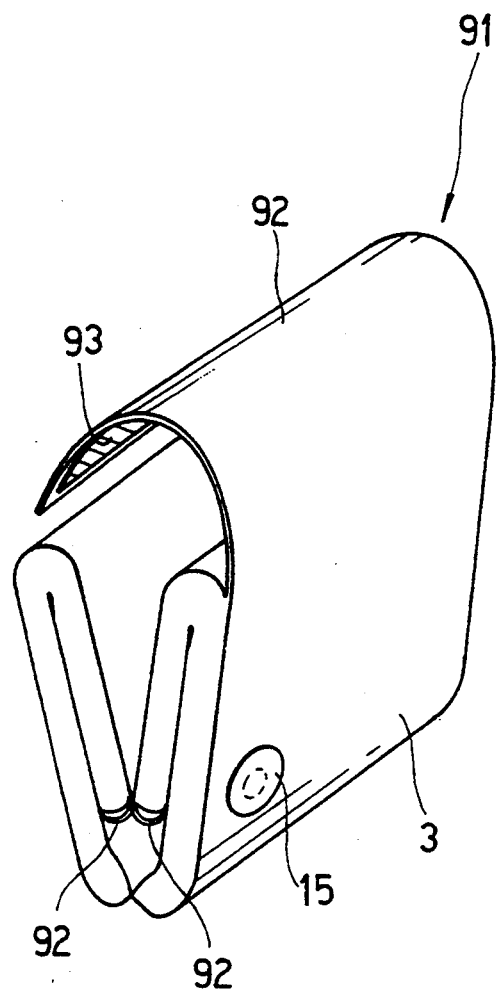

F I G. 39
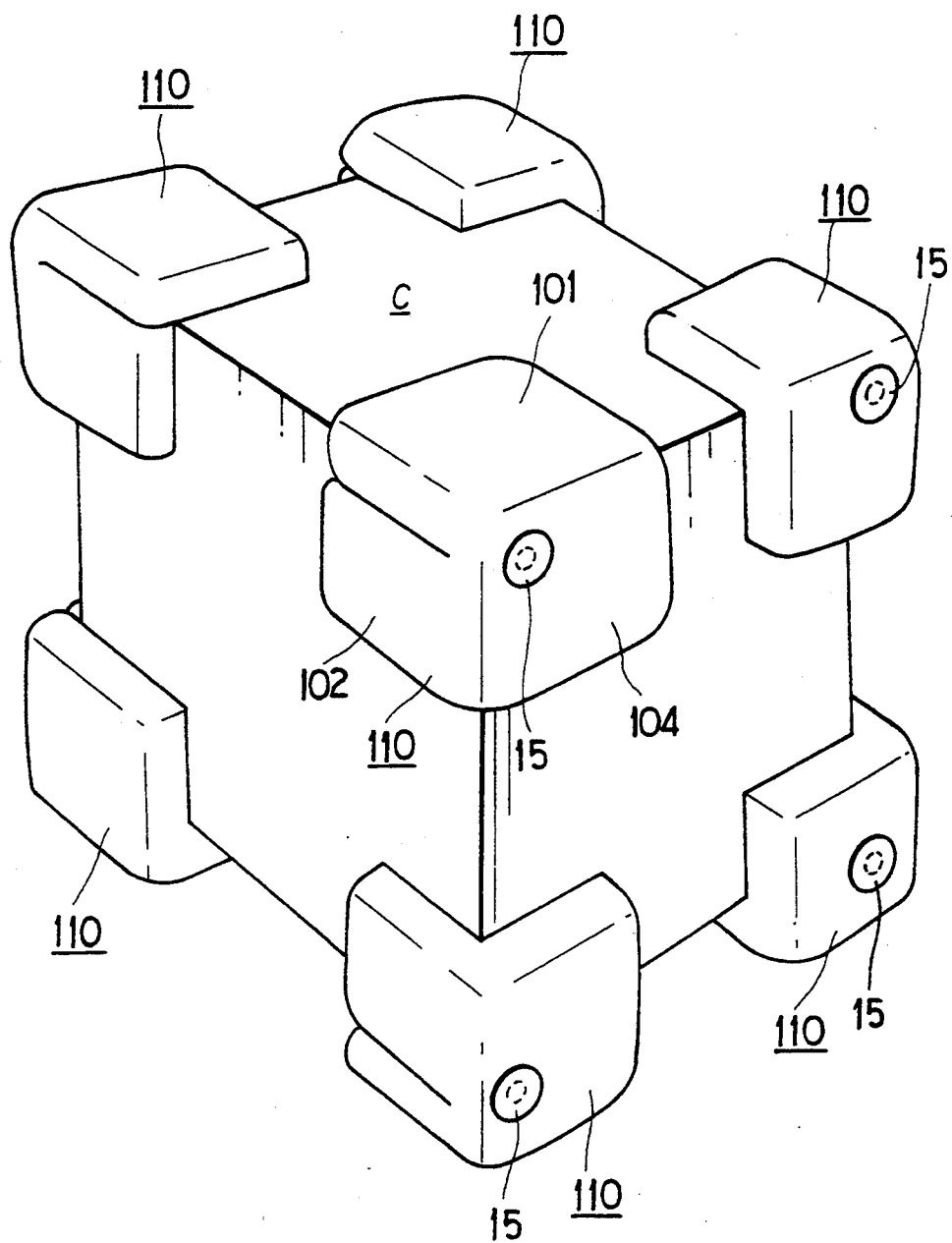

FIG. 58
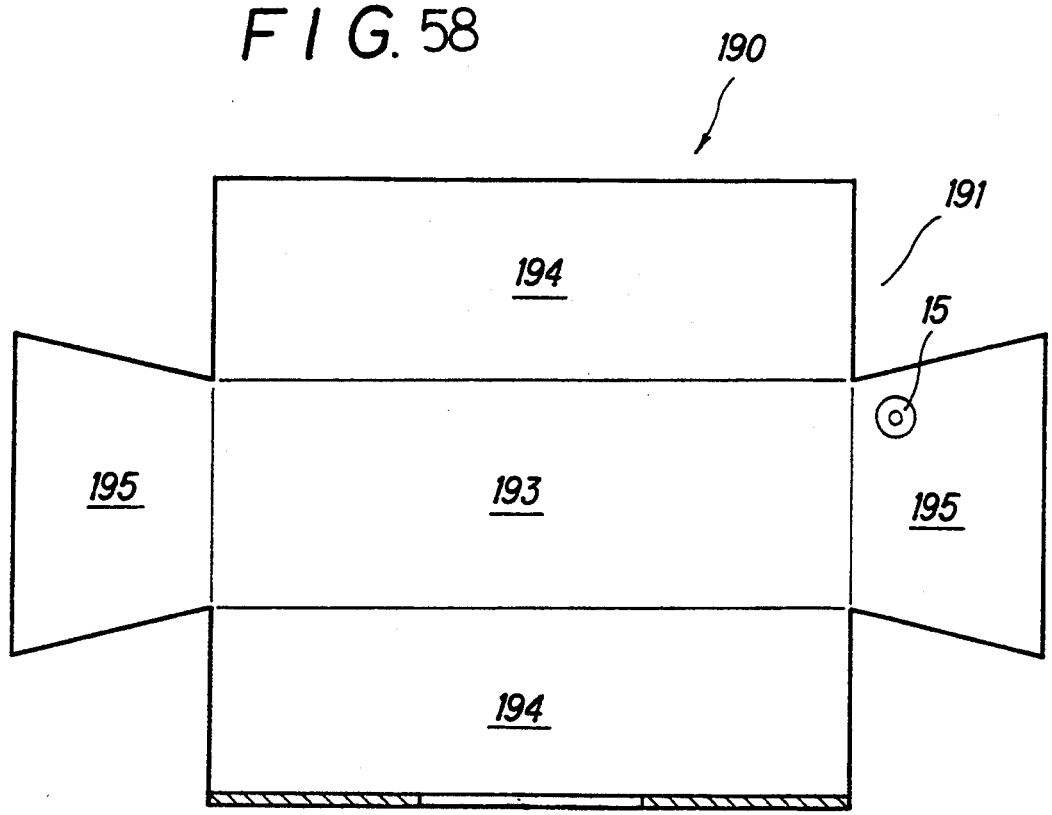
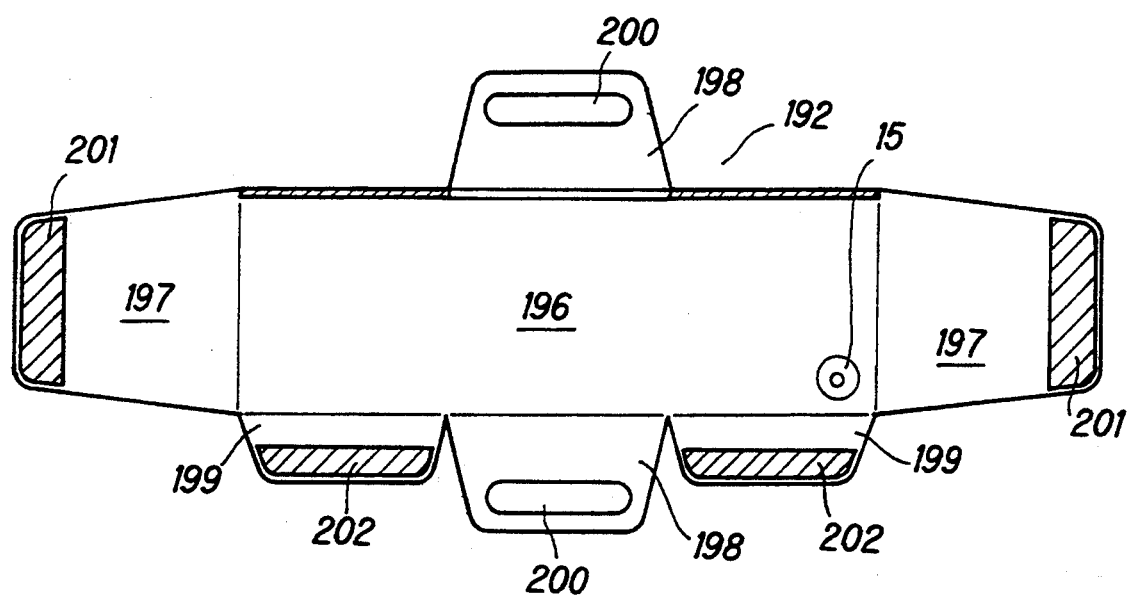

F I G. 63
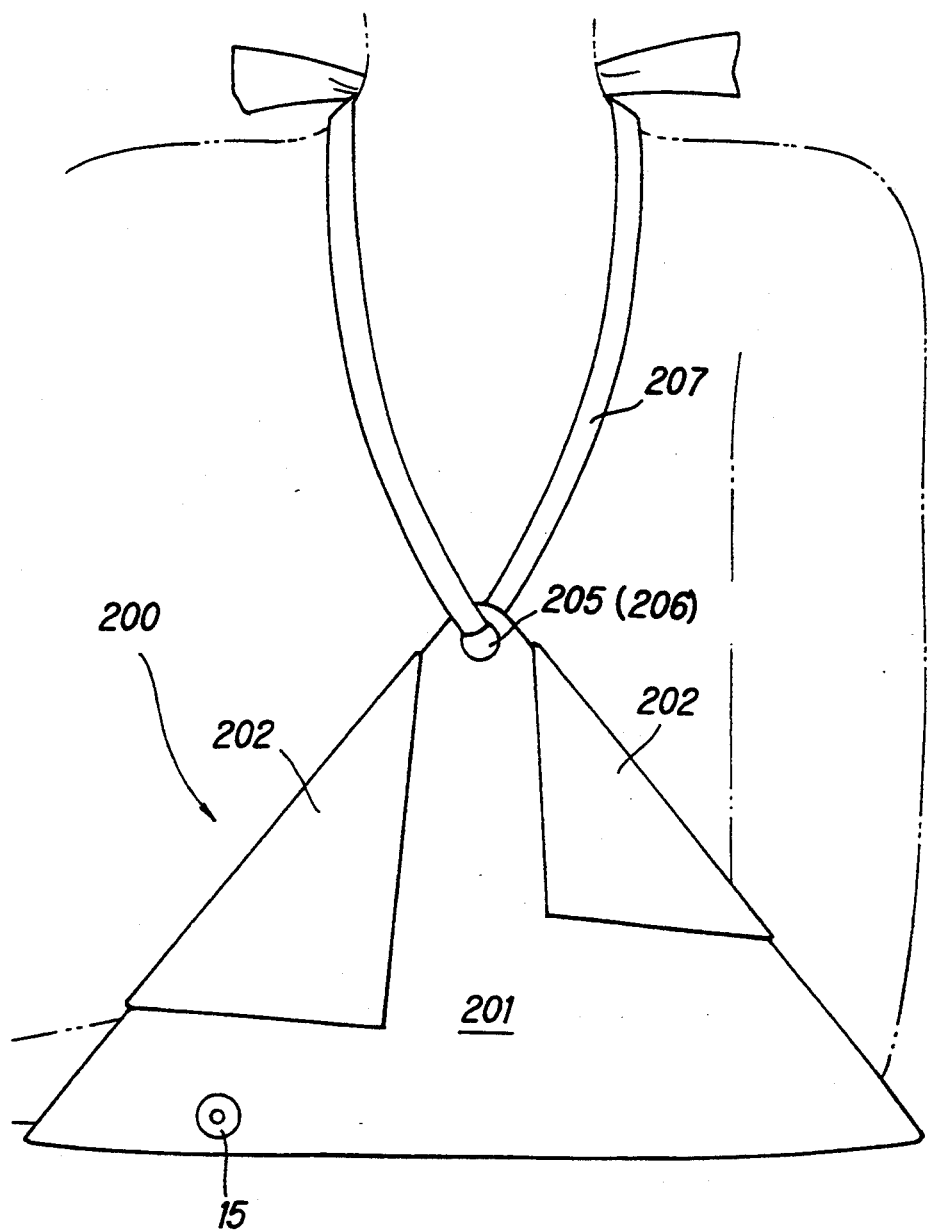

F I G. 72
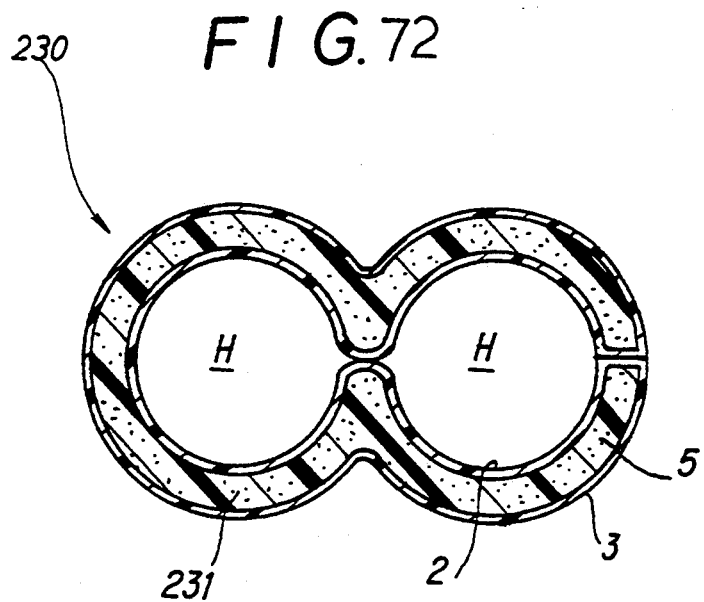
F I G. 73
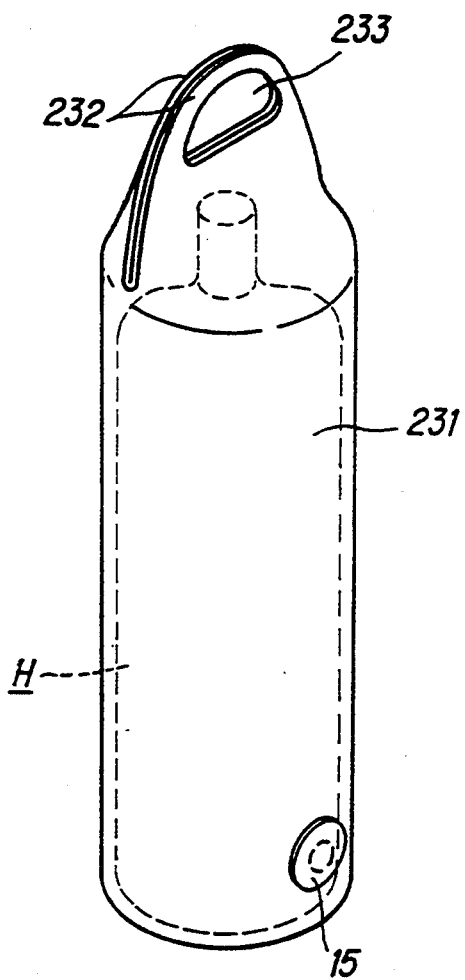

IMPACT RESISTANT WRAPPING SYSTEM

BACKGROUND OF THE INVENTION

1. Field of the Invention

This invention relates to an impact resistant wrapping system for protecting various fragile articles from shocks and damage, and more particularly to a wrapping means formed of laminated membranes filled with sponge foam or other material which usually assumes a flat state and expands to heighten the cushioning effect when wrapping an article for protection.

2. Description of the Prior Art

For the purpose of wrapping a fragile article, there have been extensively used a variety of wrappings of foamed plastics material having excellent cushioning properties, and packing or padding material of foamed styrol or the like. Since wrapping of this type has the ability of absorbing shock, which in general is in proportion to its volume, wrapping of large size is required for ensuring sufficient cushioning effect, but it is bulky and awkward to use.

As one example of a wrapping for an article to be transported, there has been proposed an inflatable package formed of an air bag having a cylindrical interior space for accommodating the article per Japanese Unexamined Patent Application Public Disclosure No. SHO 54-136985. The air bag is made by folding a double-ply sheet formed of two membranes of synthetic resin. This prior art package is used by inserting the article into the interior space of the air bag and introducing air between the membranes forming the air bag through a small air hole formed in one of the membranes to inflate the air bag.

In this prior art package, since the interior space defined in the air bag is formed in a cylindrical shape, the shape of the article to be wrapped is limited, and therefore, various articles having different shapes cannot aptly be wrapped. Furthermore, this package cannot be reused readily and is of no practical utility.

In Japanese Patent Application Publication No. SHO 63-502099 (corresp. to International Application No. PCT/US86/01989), a protective envelope for containing a fragile article is proposed, in which elastic cushion material is confined in a compressed flat state between airtight two-fold membranes constituting the protective envelope.

Similarly, this prior art protective envelope cannot cope with a variety of articles of different shapes. This is because the envelope is a definite shape and defined by basically sealing the envelope along the edges of the membranes so as to form an upper opening. Thus, this protective envelope cannot be applied to articles having various shapes, and is restricted in capacity for containing the article.

OBJECT OF THE INVENTION

An object of this invention is to eliminate the drawbacks suffered by conventional wrapping or packing means as described above and to provide a convenient wrapping means having excellent cushioning effect and which can be widely adapted to variations of shapes and sizes of articles to be wrapped.

Another object of this invention is to provide a wrapping that is easy to handle and simple in structure, and that is capable of being reused practically.

SUMMARY OF THE INVENTION

To attain the objects described above according to this invention, there is provided a wrapping means which comprises a sheet-like wrapping body formed of a first flexible membrane having gas barrier properties, and a second flexible membrane having gas barrier properties and being opposite to the first flexible membrane to define air-tightly a cavity between the first and second flexible membranes, one or more engaging members disposed on the wrapping body, elastic foam or other material placed in a compressed flat state in the cavity between the flexible membranes, and an air valve disposed on one of the flexible membranes, through which the cavity is open to introduce air into the cavity so as to allow the cushion material to expand.

The sheet-like wrapping body of the wrapping means according to this invention has a flexible triple-layer structure of the two flexible membranes and the elastic sponge foam or other material placed between the flexible membranes. One of the two flexible membranes serves as an inner wall which comes into direct contact with the given article to be wrapped, and the other flexible membrane is an outer wall of the wrapping means. The outer wall is operatively associated with the inner wall which changes in shape with the article wrapped in the wrapping body.

The sponge foam material placed between the flexible inner and outer membranes may be formed of synthetic resin foam, particularly compressed polyurethane foam, which is held in its compressed state under reduced pressure and expands in the atmosphere.

The first and second flexible membranes may be formed of plastic material having gas barrier properties, such as thermoplastic resin having very low permeability to air.

The engaging member attached to the flexible membranes may be formed of a set of female and male fastening members, pressure sensitive adhesive or a slide fastener such as a zip fastener. When using a surface fastener, a female fastening member attached to one of the flexible membranes is closely contacted with a male fastening member on the other flexible membrane.

The engaging member in this invention may be formed so as to extend outward from an edge portion of the sheet-like wrapping body.

Also, the engaging member in this invention may be provided with auxiliary cushioning pads for absorbing shocks. Similarly to the sheet-like wrapping body, the cushioning pad may comprise flexible inner and outer membranes between which a cavity is air-tightly defined, an elastic cushion material held in a compressed flat state between the flexible inner and outer membranes, and an air valve for permitting the cavity to open to the air.

The air valve in this invention includes a vent hole bored or cut in one of the flexible membranes and a sealing member for sealing the vent hole. This air valve may be located anywhere on the outer surface of the sheet-like wrapping body.

The sealing member attached to the flexible outer membrane may be formed of plastic material having gas barrier properties and can be peeled off from the air valve.

In another way, the sheet-like wrapping body of this invention may be provided with an air valve comprising a vent hole and a slide plate with an aperture, which is adapted for slidably opening the vent hole. The slide plate is provided with a sharp-edged cutter for cutting or boring a hole in the flexible outer membrane. For example, the slide plate assembled in the air valve may be formed of a substantially U-shaped triple-layer member having a vent hole formed in conjunction with a retaining plate disposed between two plastic plates, and a cutter member with a hole which is slidable in the triple-layer member so as to permit the vent hole to communicate with the hole in the cutter member.

The air valve may be operated by use of a valve string threaded into the cavity through one of the flexible membranes and a pull string connected to the valve string.

Moreover, the air valve in this invention may be integrally attached to the engaging member. For instance, the air valve may be formed by attaching the sealing member to a prescribed portion of the flexible outer membrane which is opposite to the engaging member fixed on the flexible inner membrane, so that the sealing member can be pricked with a needle-like blade.

The air valve may be provided with a simple sound generator capable of issuing a sound resulting from air flowing through the air valve.

The sheet-like wrapping body may be formed of a flexible gas-barrier plastic membrane, a laminated flexible plastic film formed on the plastic membrane, and flexible porous cushion material disposed on the surface of the plastic membrane opposite to the laminated plastic film.

According to this invention, a given article can be readily wrapped with the sheet-like wrapping body in accordance with the shape of the article and held by engaging the engaging member. Subsequently, the air valve is opened to introduce air into the cavity which has been kept at reduced pressure in the sheet-like wrapping body. Thus, the elastic cushion material held in its compressed state at reduced pressure in the sheet-like wrapping body spontaneously expands as the cavity is open to the air. As a result, the sheet-like wrapping body having the article wrapped entirely therein is inflated, and the joined engaging member exerts further tension force to the inflated wrapping body so as to tightly wrap the article with the wrapping body.

The article wrapped with the inflated wrapping body can easily be relieved only by disengaging the joined engaging member and unrolling the wrapping body. Then, the air valve is opened to draw out the air in the cavity of the wrapping body by using a vacuum cleaner or pressing the wrapping body by hand so as to compress the elastic cushion material placed in the cavity portion. Then, the air valve is closed to keep the elastic cushion material in the compressed flat state in the cavity. Thus, the wrapping means of this invention can be reused.

Other and further objects of this invention will become obvious upon an understanding of the illustrative embodiments about to be described or will be indicated in the appended claims, and various advantages not referred to herein will occur to one skilled in the art upon employment of the invention in practice.

BRIEF DESCRIPTION OF THE DRAWINGS

The other objects and features of the present invention will be hereinafter explained in detail with reference to the accompanying drawings, in which:

FIG. 31 is a perspective view of the wrapping means of FIG. 30, in use;

FIG. 39 is a perspective view of the wrapping means of FIG. 38, in use;

FIG. 58 is an unfolded view of a twentieth embodiment of the wrapping means of this invention, in its separated state;

FIG. 63 is a plan view of FIG. 62, in use;

FIG. 72 is a cross-sectional view showing the the wrapping means of FIG. 71, in use; and FIG. 73 is a perspective view of a twenty-fifth embodiment of the wrapping means of this invention.

DESCRIPTION OF THE PREFERRED EMBODIMENTS

With reference to FIG. 1 through FIG. 7, the first and second embodiments of the wrapping means of this invention will be described hereinafter.

Figure 1:
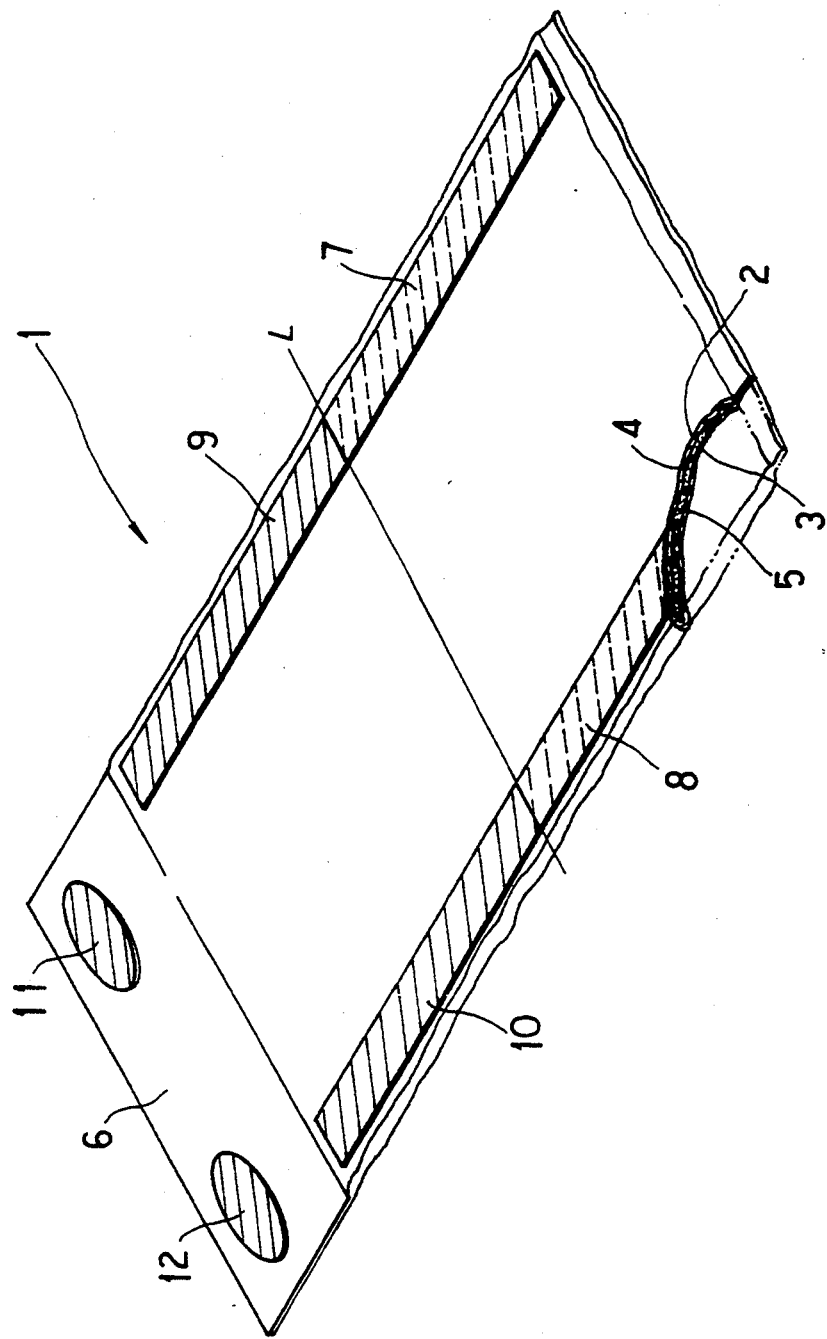
FIG. 1 is a partially sectioned perspective view showing a first embodiment of the wrapping means according to this invention.
Figure 2:
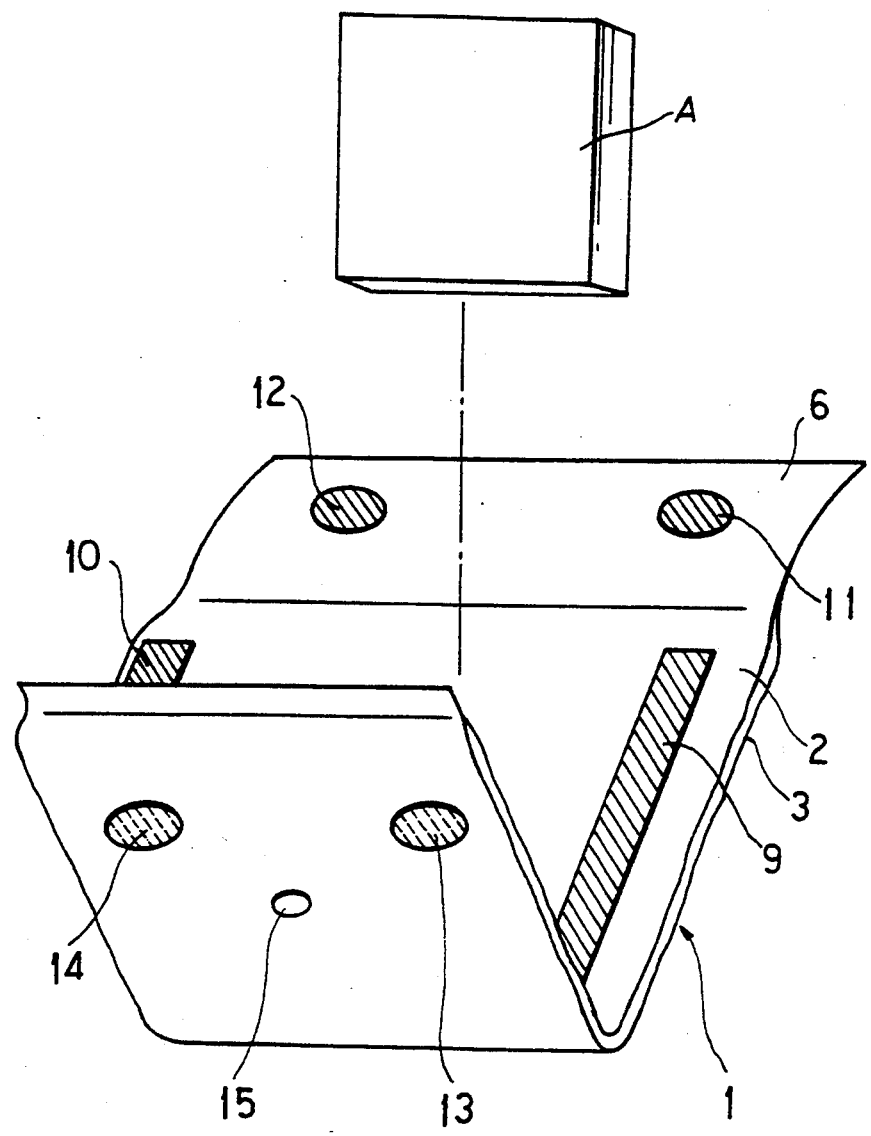
FIG. 2 is a perspective view showing the principal portion of FIG. 1.
Figure 3:
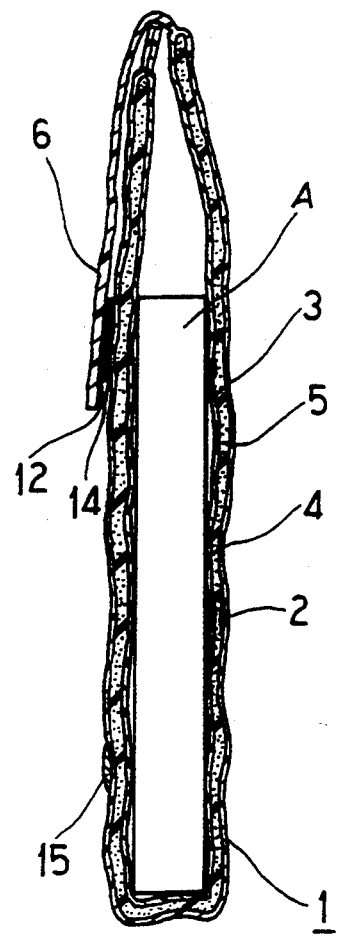
FIG. 3 is a section showing the manner of wrapping an article that is wrapped with the wrapping means of FIG. 1 in a flat state.
Figure 4:
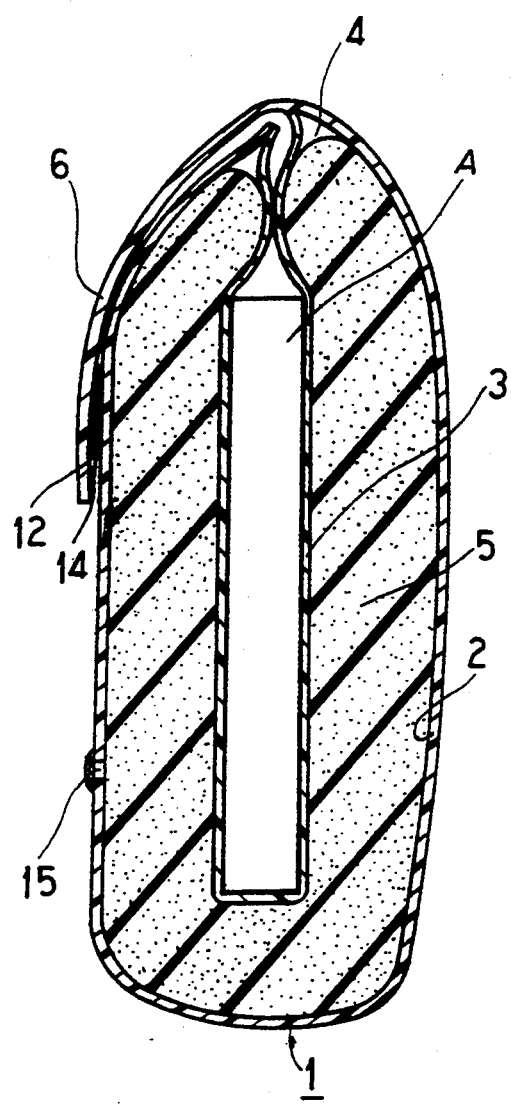
FIG. 4 is a longitudinal section showing the wrapping means of FIG. 3 in an inflated state.

The wrapping means of this invention comprises a sheet-like wrapping body 1 formed of a flexible inner membrane 2 having gas barrier properties and a flexible outer membrane 3 which has gas barrier properties and is opposite to the inner membrane 2 in a double-ply state, and elastic sponge foam cushion material 5 placed in a cavity 4 defined airtightly between the flexible inner and outer membranes 2 and 3. The elastic cushion material 5 is normally placed in its compressed flat state in the cavity between the flexible membranes. The wrapping means further includes a flexible lid cover 6 extending in the longitudinal direction from the wrapping body 1, and engaging members composed of female surface fasteners 7 and 8 attached to both side edge portions of one half of the flexible inner membrane 2 and male surface fasteners 9 and 10 attached to both side edge portions of the other half of the flexible inner membrane 2. The wrapping means has another engaging means composed of male surface fasteners 11 and 12 attached to the lid cover 6 and female surface fasteners 13 and 14 attached to the corresponding portions of the flexible outer membrane 3 as shown in FIG. 2. The flexible outer membrane 3 has an air valve 15.

The flexible inner and outer membranes 2 and 3 may be preferably formed of plastic material having gas barrier properties, or plastic-laminated paper.

Figure 5:
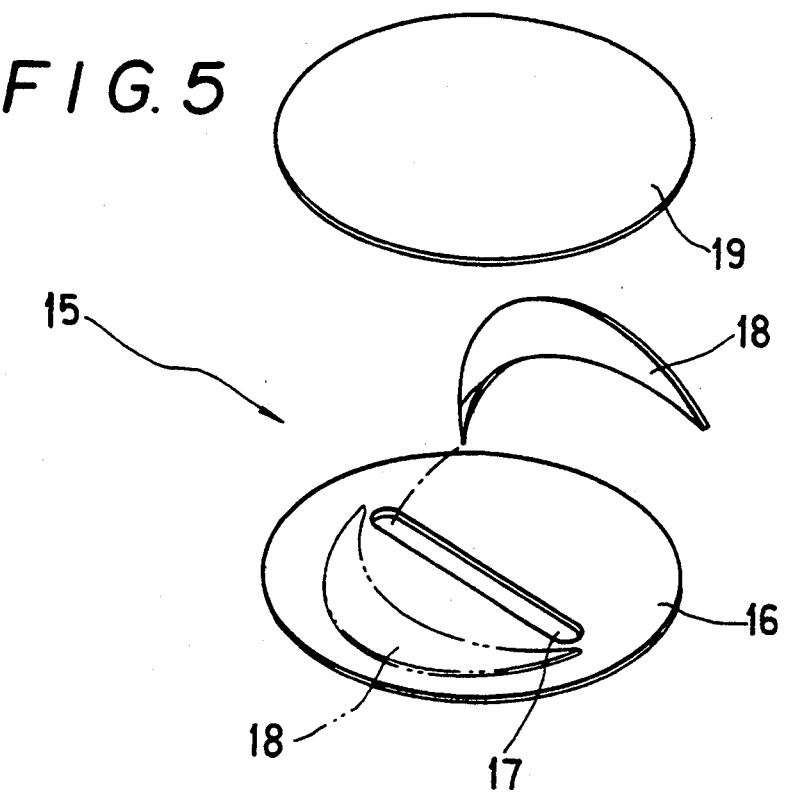
FIG. 5 is a perspective view showing an air valve with a cutter member.
Figure 6:
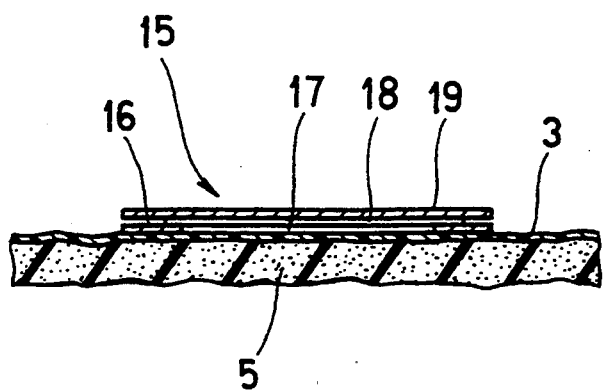
FIG. 6 is a sectional view of the air valve of FIG. 5 attached to the wrapping means.
Figure 7:
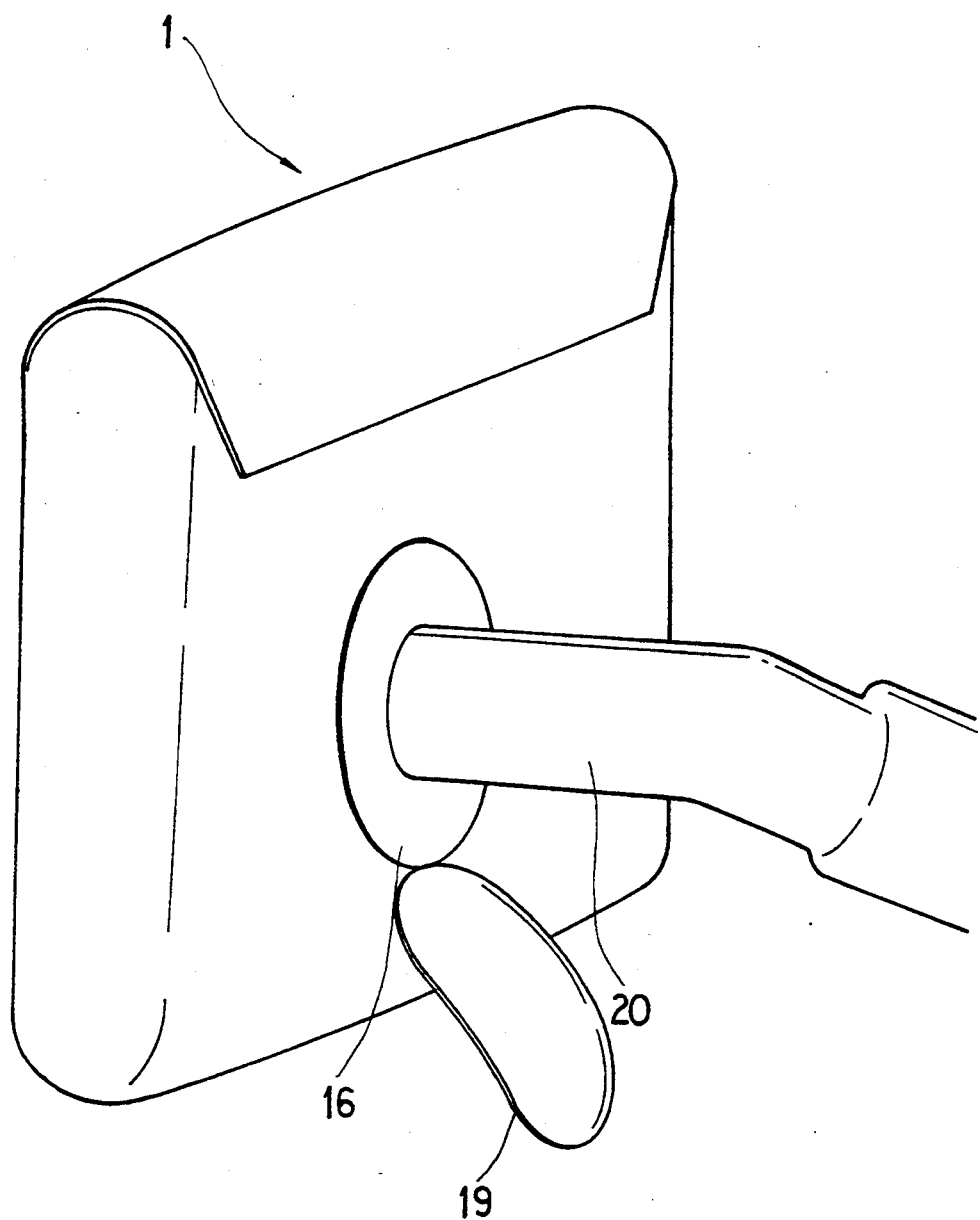
FIG. 7 is a perspective view showing the manner in which air is sucked out of the wrapping means.

As shown in FIG. 5 as the second embodiment of this invention, the air valve 15 may be constituted by a base 16 fixed on the flexible outer membrane 3, a cutter member 18 mounted on the base 16, and a sealing member 19 capable of being detachably attached to the base 16. The base 16 of the air valve is provided in its central portion thereof with an air vent 17 formed in a slit. The cutter member 18 is formed of rigid plastic material and is made thin so as to be stuck into the air vent 17 in the base 16. The sealing member 19 may be applied with pressure sensitive adhesive so as to be stuck to the base 16 by pressing to close the air vent 17.

When using the wrapping means as constructed above for wrapping a given article A, the sheet-like wrapping body 1 is folded in two along the center line L so that the article A is put between the folded half parts of the flexible inner membrane 2. Then, by engaging the female and male surface fasteners 7, 9 and 8, 10 and the female and male surface fasteners 11–14, the article is loosely wrapped with the wrapping means.

Thereafter, the sealing member 19 is removed from the air valve 15 to expose the base 16 so that the air vent 17 is opened by sticking the cutter member 18 thereinto. As a result, air is introduced into the cavity 4 formed between the outer and inner membranes 2 and 3, causing the cushion material 5 placed in its compressed flat state in the cavity 4 to expand spontaneously. Then, the air vent 17 may be finally sealed with the sealing member 19. Thus, the article is firmly wrapped with the wrapping means.

The article wrapped with the wrapping means can be released easily by disengaging the engaging members composed of the surface fasteners 7–14. The air may be sucked out from the cavity 4 defined between the outer and inner membranes 2 and 3 by using a vacuum cleaner or other suction means 20 (FIG. 7), or discharged by pressing the wrapping means by hand. When the wrapping means is contracted, the air vent 17 is sealed with the sealing member 19 so as to keep the wrapping means in its original flat state. Thus, the wrapping means of this invention can be reused usefully.

The sheet-like wrapping body 1 of this embodiment is formed by thermal-sealing the peripheral edge portions of the flexible inner and outer membranes joined together and made of compressed polyurethane foam having gas barrier properties, thus defining the cavity 4. Since the elastic sponge foam material 5 is made of compressed polyurethane foam, the cushion material 5 generally expands about six times as large as its original size. In the wrapping means actually produced according to this invention, the wrapping body which has a thickness of about 1 cm in its contracted state was inflated to about 7.6 cm in thickness. Thus, the given article A can be effectively wrapped with the wrapping body and securely protected from shocks caused in transit or storage.

Since the female and male surface fasteners attached to the flexible inner and outer membranes are used as engaging members, the condition in which the article is wrapped with the sheet-like wrapping body can be adequately maintained. In place of the surface fasteners, there may be used pressure sensitive adhesive or a slide fastener such as a zip fastener. With these fastener means, the flexible membranes can be engaged face to face with each other with a simple operation.

By using the wrapping means actually produced according to this embodiment of the present invention, the wrapping means could be decreased to 80% in storage space, one quarter in volume and two thirds in weight. Moreover, since the wrapping means according to this invention can be used without any other packing tape, wadding and so on, packing expenses can be markedly reduced to less than 63% in comparison with known wrapping or packing means.

Figure 8:
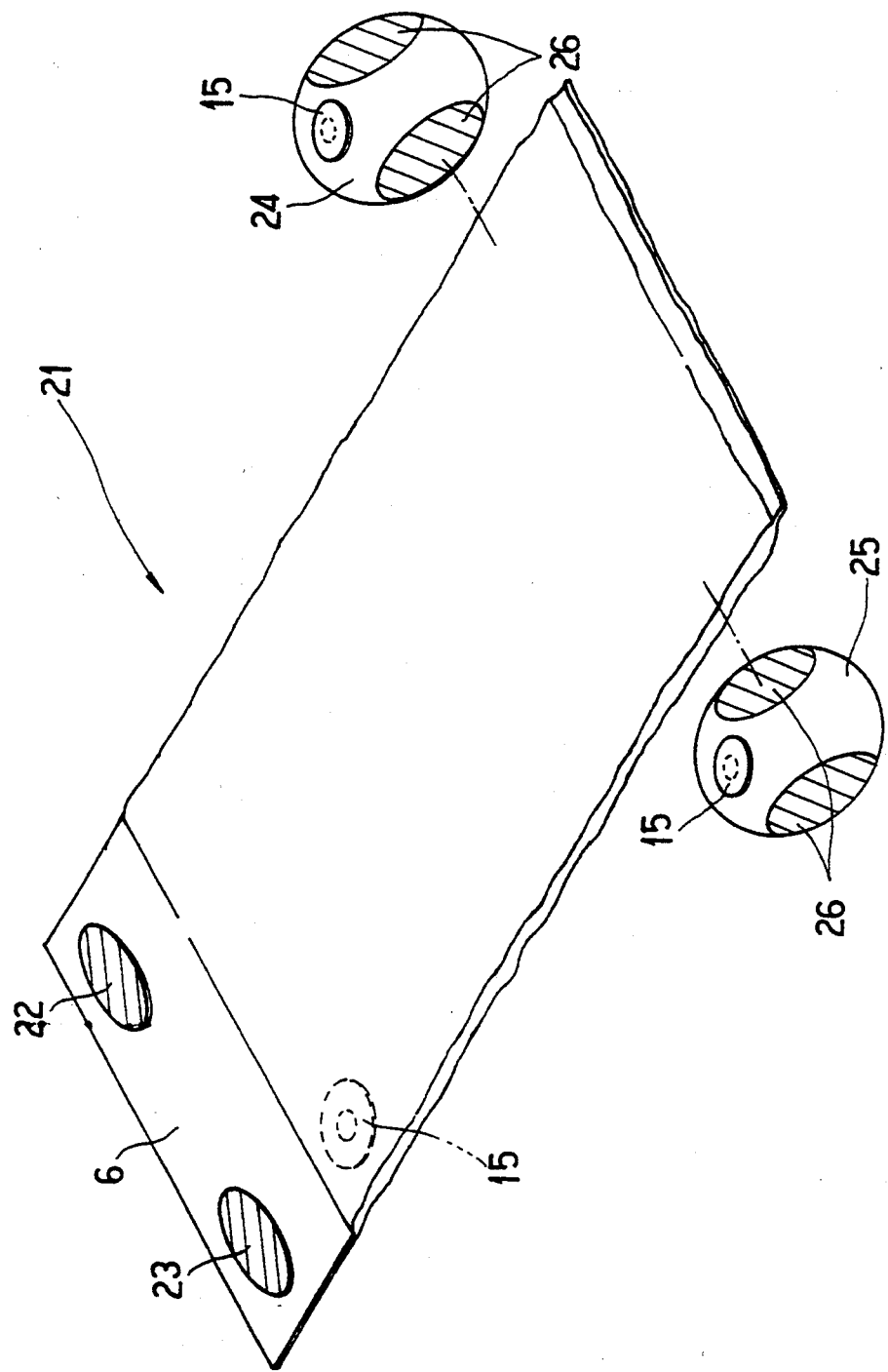
FIG. 8 is a perspective view showing a second embodiment of the wrapping means of this invention.
Figure 9:
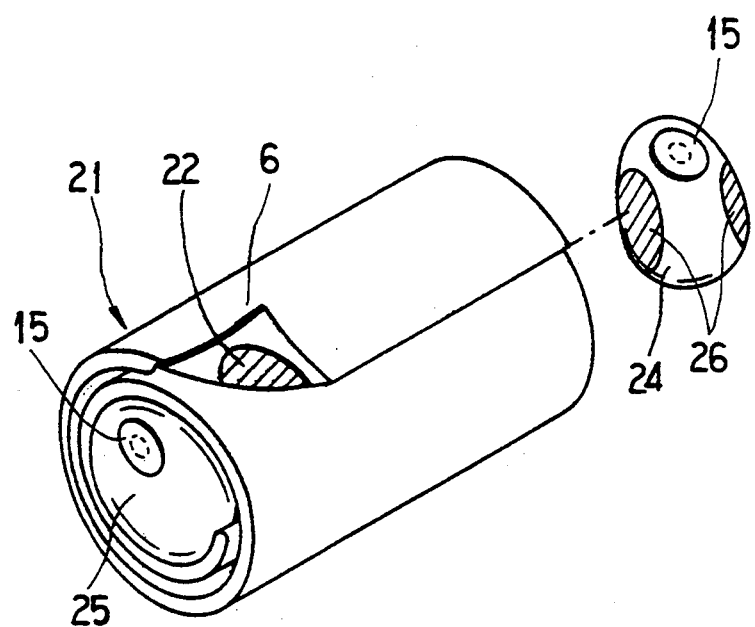
FIG. 9 is a perspective view of the wrapping means of FIG. 8, in use.

The second embodiment shown in FIG. 8 and FIG. 9 is adapted to wrap a cylindrical article and comprises a rectangular wrapping body 21 and a lid cover 6 with pressure sensitive adhesives 22 and 23. It is preferable to use round-shaped cushioning pads 24 and 25 with one or more pressure sensitive adhesives 26. The pressure sensitive adhesives 22, 23 and 26 each are covered with a release paper.

FIG. 9 shows the state in which the cylindrical article is wrapped with the wrapping means in the rolled state. The wrapping body 21 can be steadily retained in the cylindrical state of wrapping the cylindrical article by means of pressure sensitive adhesives 22 and 23. Then, the cushioning pads 24 and 25 are attached to the respective round end portions of the roll of the wrapping means to protect the wrapped article from shocks in all directions. This wrapping means according to this embodiment can be employed for wrapping receptacles for cosmetics, and medicines, various articles, expensive gifts and other valuable goods.

Figure 10:
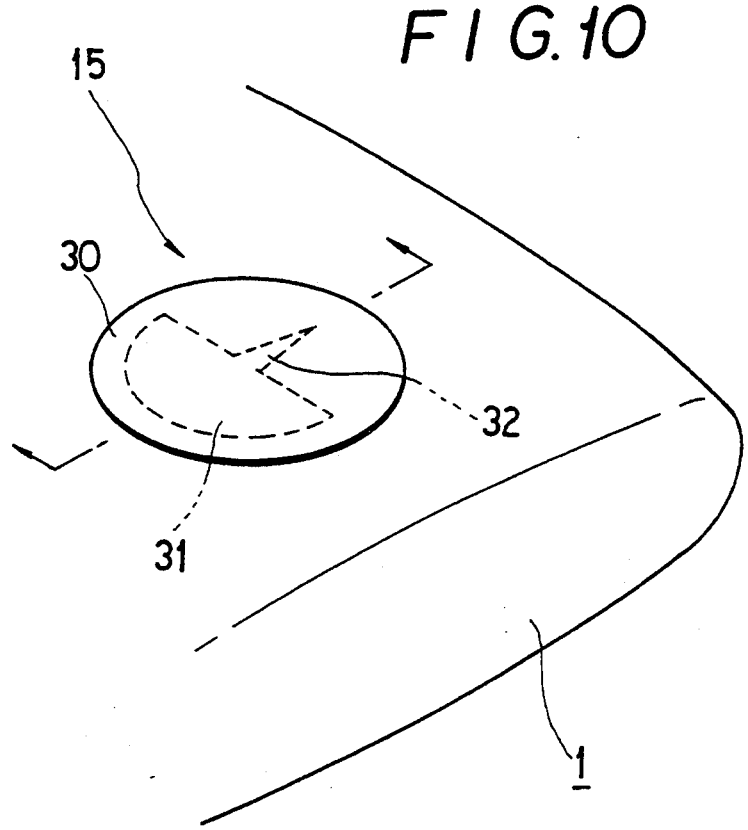
FIG. 10 is a perspective view showing an air valve disposed on the wrapping means of FIG. 8.
Figure 11:
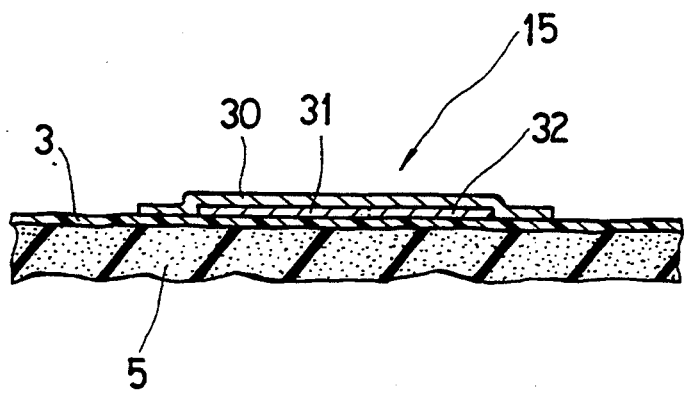
FIG. 11 is a sectional view of FIG. 10.
Figure 12:
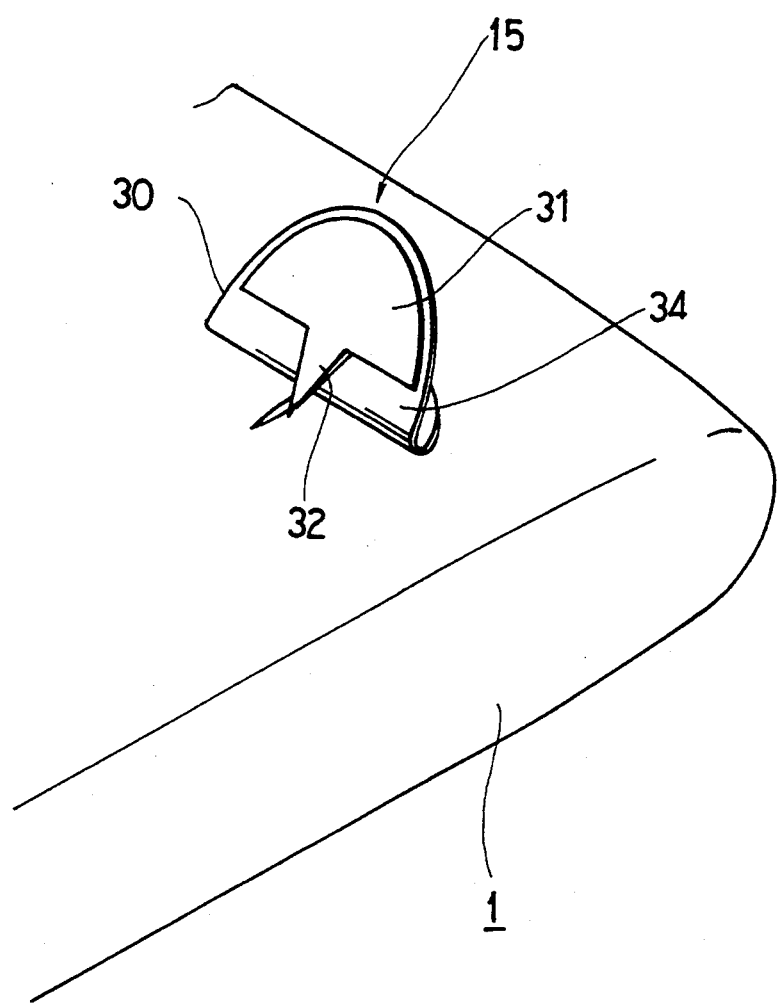
FIG. 12 is a perspective view showing the air valve of FIG. 10 in its operated state.

FIG. 10 through FIG. 12 show an embodiment of a modified air valve 15. A sealing member 30 is provided with a cutter member 31 having a pointed blade 32. The cutter member 31 is operated to automatically prick the flexible outer membrane 3 with the pointed blade 32 merely by pulling up the edge of the sealing member 30, thus allowing air to enter into the cavity through a hole cut by the cutter member 31. After introducing the air into the cavity in the wrapping body 1, the opening hole cut by the pointed blade 32 is again closed with the sealing member 30.

The cutter member 31 with the pointed blade 31 is formed of a rigid plastic plate or the like and made smaller than the sealing member 30. The cutter member 31 may be adhered along with the sealing member 30 to the flexible outer membrane 3 with a bonding agent. This embodiment has an advantage in that the cutter member 31 can be easily attached to the wrapping body 1 after producing the wrapping body 1.

Figure 13:
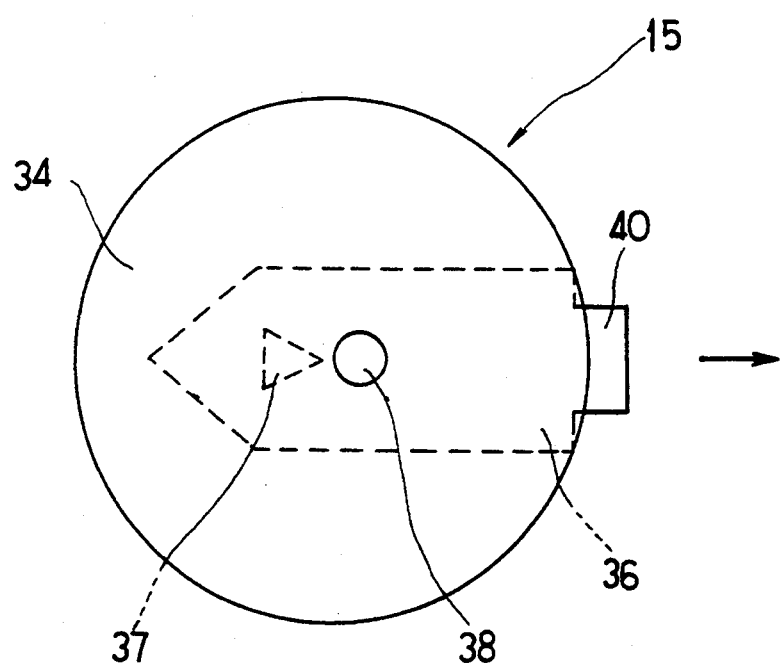
FIG. 13 is a plan view showing another of an air valve having a modified structure.
Figure 14:
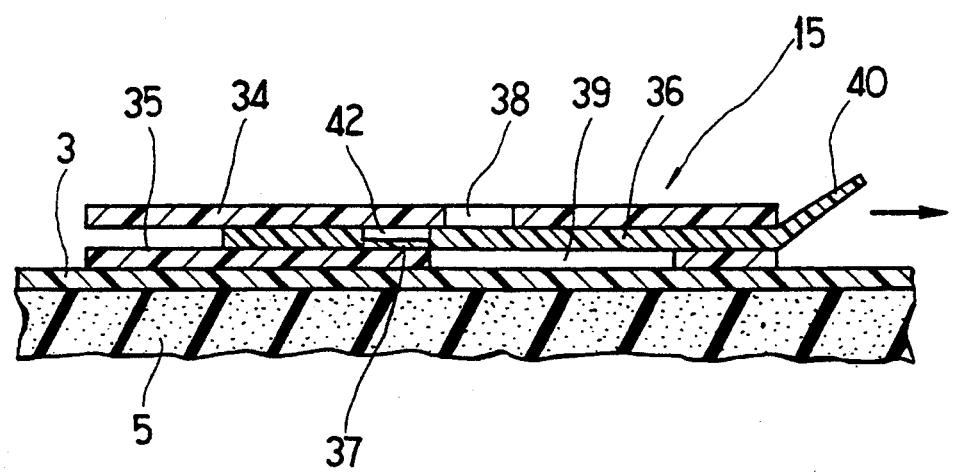
FIG. 14 is a section of the air valve of FIG. 13, in its closed state.
Figure 15:
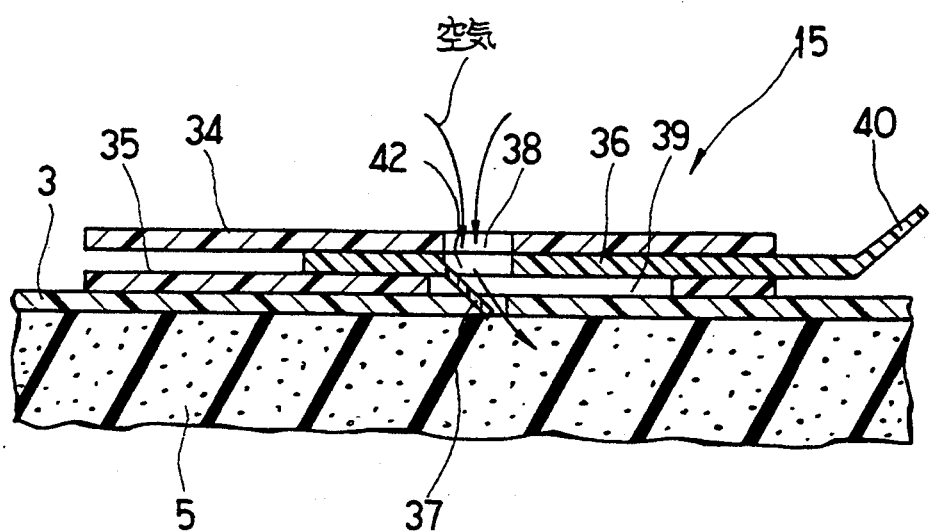
FIG. 15 is a section of the air valve of FIG. 13, in its open state.

FIG. 13 through FIG. 15 show an air valve 15 having a slide plate 36 slidably set between two plastic plates 34 and 35 having vent holes 38 and 39. The slide plate 36 has a sharp-edged cutter 37 elastically urged toward the flexible outer membrane 3. By manually sliding the slide plate 36 to align the cutter 37 with the hole 39, the cutter 37 urged downward pops automatically out to cut the flexible outer membrane 3, thus allowing air to flow into the cavity in the wrapping body through the holes 38, 42 and 39. As a result, the compressed cushion material placed in the, wrapping body expands spontaneously. According to this embodiment of the invention, the air valve 15 can be easily handled by using a pulling piece 40 extending from the slide plate 36.

Figure 16:
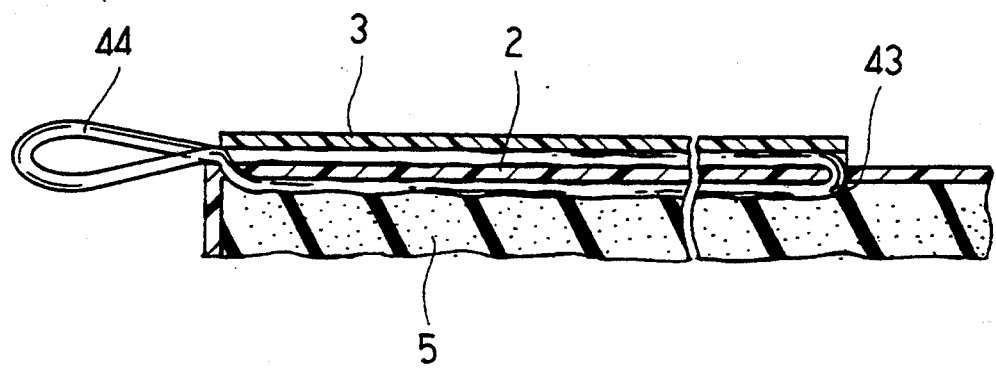
FIG. 16 is a view of another embodiment of an air valve of this invention.

FIG. 16 shows an embodiment of a string air valve 15 comprising a valve string 43 of proper length penetrating through the flexible outer membrane 3 and passing through the cavity 4, and a pull string 44 connected to the valve string 43 and extending outside. By pulling the pull string 44 by hand, the flexible inner membrane 2 is cut, thus allowing air to enter into the cavity 4 and the cushion material 5 to expand.

The air valve in this embodiment may be provided with a simple sound generator capable of producing an alarm sound by the action of air flowing through the air valve. By confirming that the alarm sound fades out, the completion of the introduction of air into the cavity which is carried out by use of a vacuum cleaner or the like can be recognized. Even when the air in the cavity is drawn out by using a vacuum cleaner or exerting pressure on the wrapping body by hand, the completion of drawing out the air from the cavity can be recognized by means of the sound generator.

Figure 17:
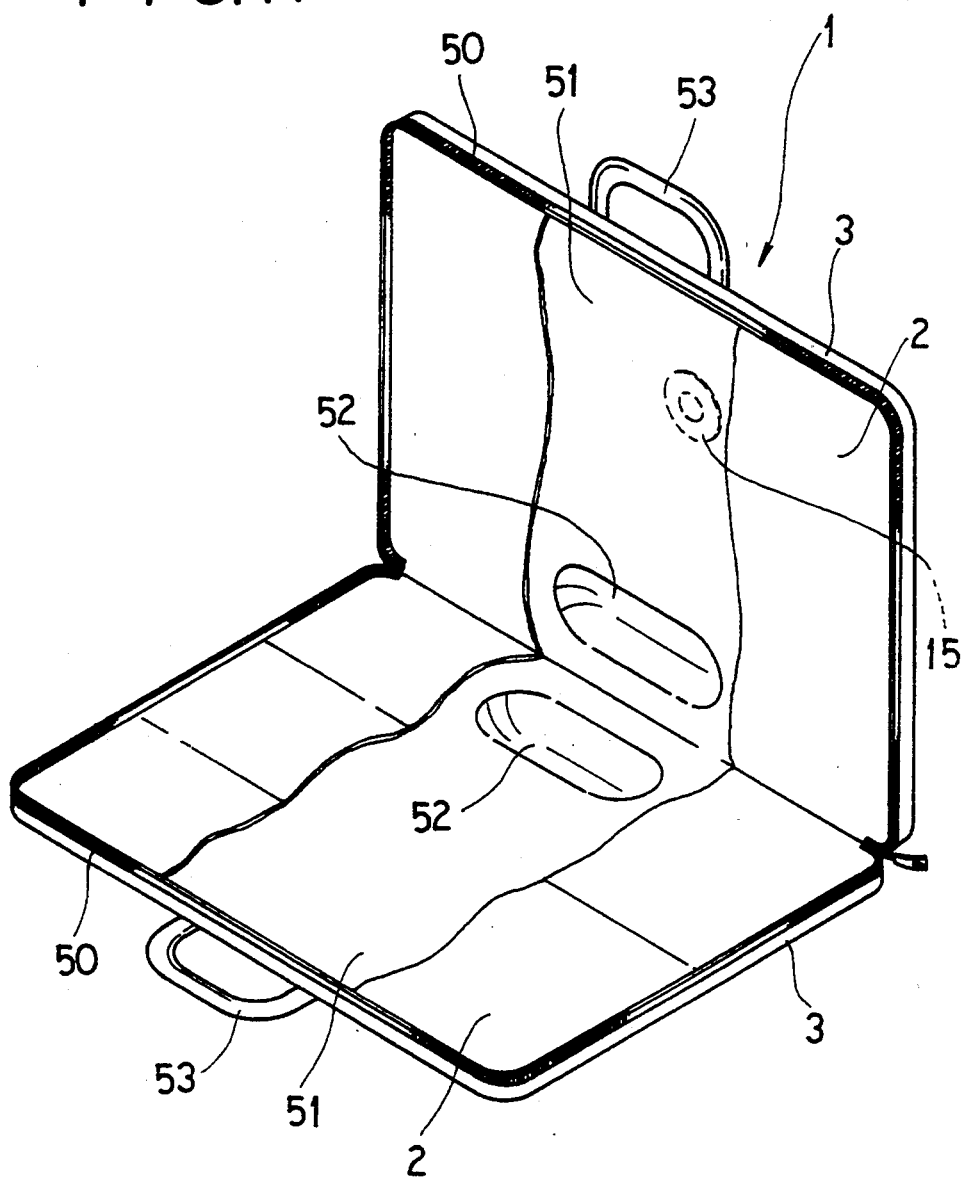
FIG. 17 is a perspective view of a third embodiment of wrapping means of this invention.

The embodiment of the wrapping means illustrated in FIG. 17 uses, as the engaging means, a slide fastener 50 such as a zip fastener. The slide fastener 50 is attached to the peripheral edge of a rectangular wrapping body 1. The flexible inner membranes 2 are provided with inside pockets 51 with openings 52 for accommodating a given article to be wrapped. With the inside pockets, the article can be securely held in the wrapping means of this embodiment by inflating the wrapping means by action of the air introduced through the air valve 15.

Figure 18:
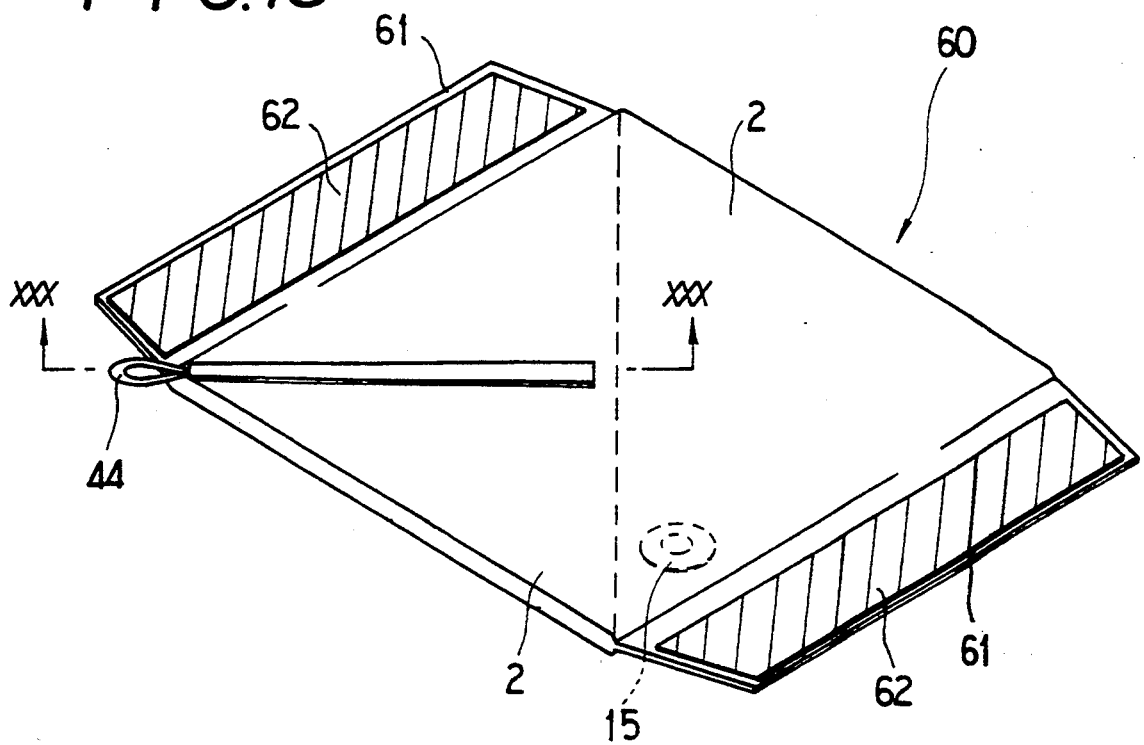
FIG. 18 is a perspective view of a fourth embodiment of the wrapping means of this invention, in its unfolded state.
Figure 19:
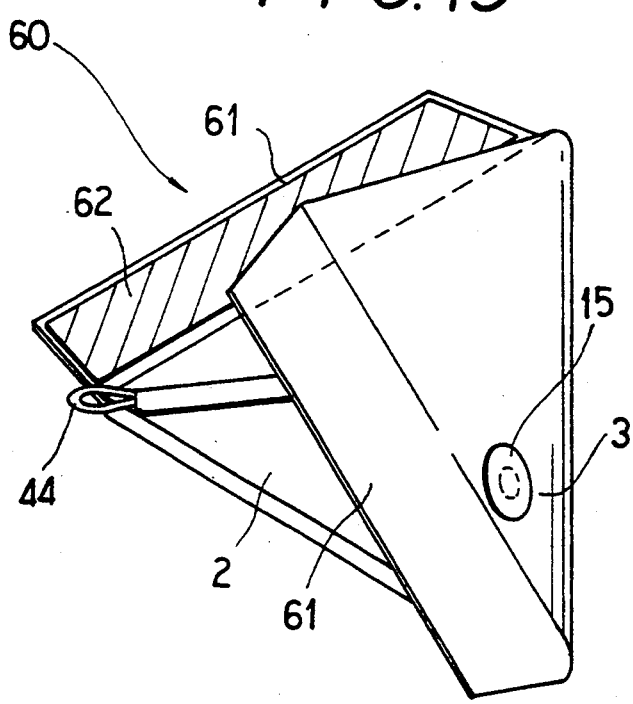
FIG. 19 is a perspective view of the wrapping means of FIG. 18, in its folded state.
Figure 20:
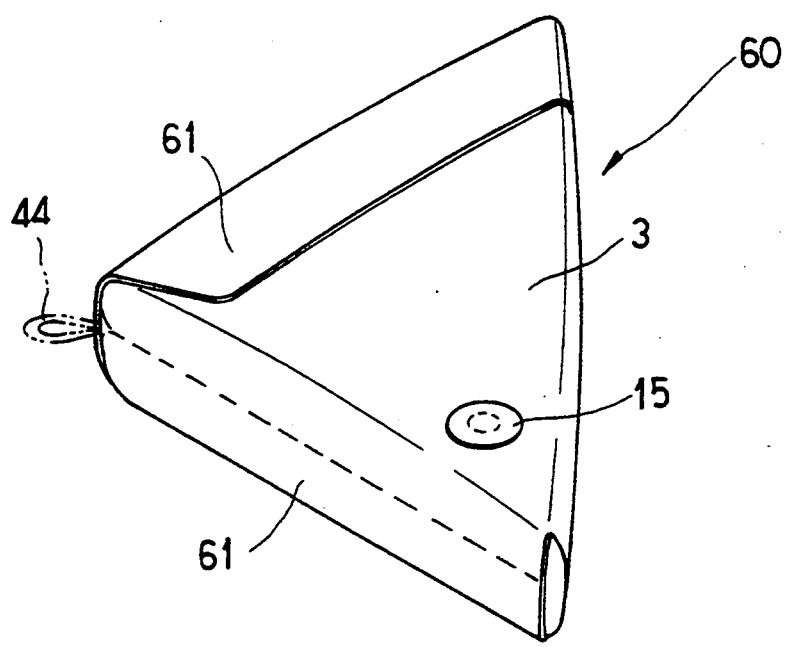
FIG. 20 is a perspective view of the wrapping means of FIG. 18, in use.

In the embodiment shown in FIG. 18 to FIG. 20, a sheet-like wrapping body 60 is used in such a manner that it is diagonally folded in two with the flexible inner membrane inside. The wrapping body 60 has lid covers 61 applied with pressure sensitive adhesives 62.

To be more specific, the wrapping body 60 is diagonally folded in two so as to assume a substantially conical shape as shown. The air valve in this embodiment is constituted by a pull string 44 which is pulled to cut the flexible inner membrane 2. As a result, air enters into the cavity in the wrapping body 60, thus expanding the elastic cushion material in the wrapping body. The wrapping means of this embodiment can be conveniently applied for wrapping various accessories, glasses, jewels and so on.

Figure 21:
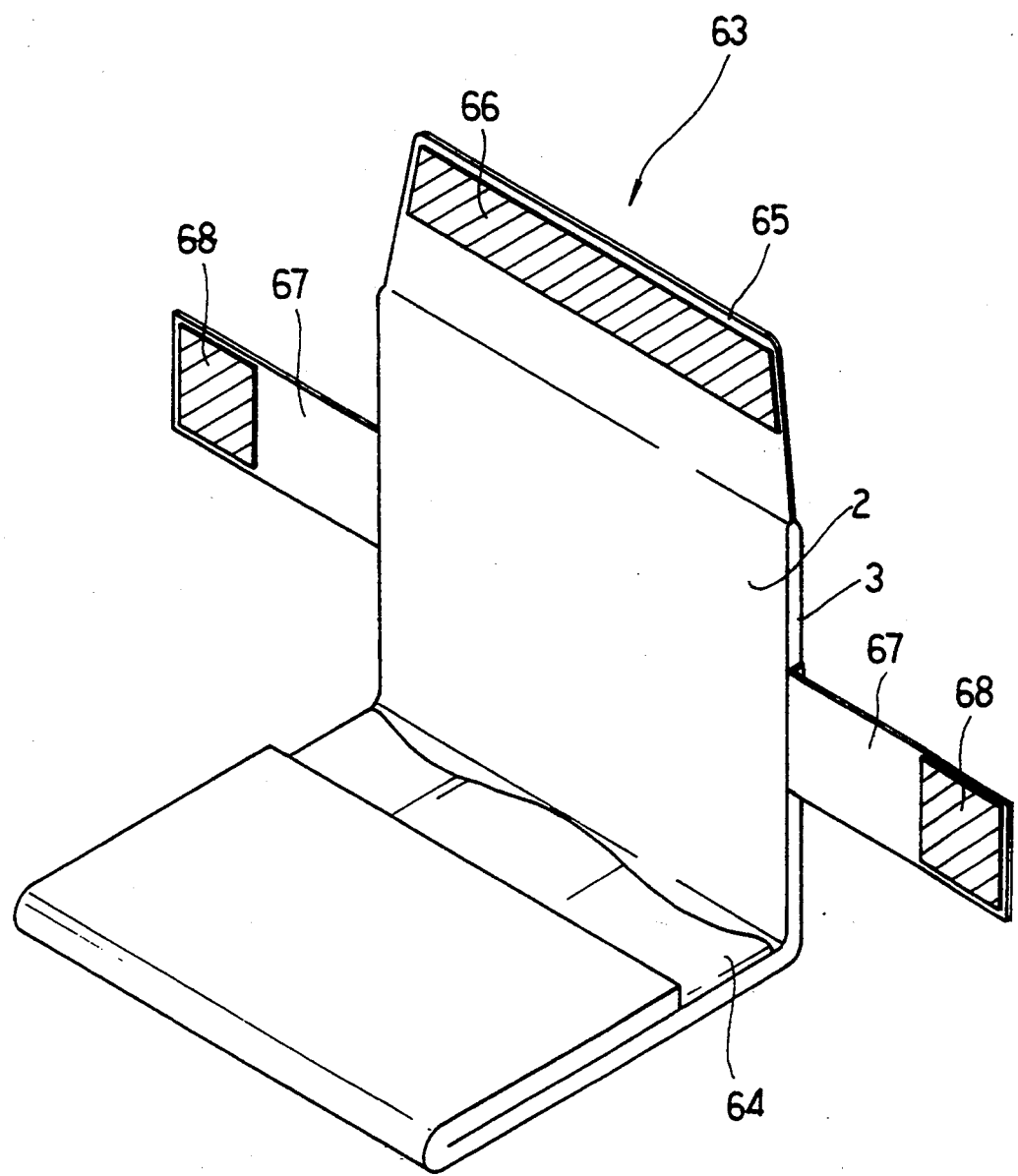
FIG. 21 is a perspective view of a fifth embodiment of the wrapping means of this invention.
Figure 22:
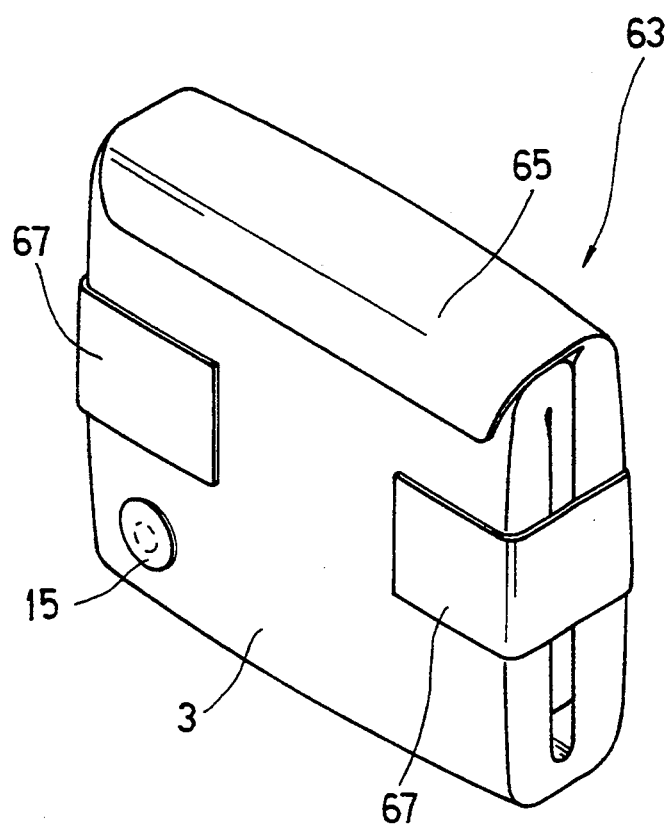
FIG. 22 is a perspective view of the wrapping means of FIG. 21, in use.

The embodiment shown in FIG. 21 and FIG. 22 has an inside pocket 64 in the flexible inner membrane 2 and in use is folded in three. Upon folding the wrapping body into three with flexible inner membrane 2 inside, a lid cover 65 and fixing bands 67 are fixed onto the flexible outer membrane 3 with pressure sensitive adhesives 66, 68 attached to the inner surface of the lid cover 65 and the fixing bands 67, respectively. According to the wrapping means of this embodiment, a given article can be appropriately wrapped and effectively protected from shocks. Particularly, compact disks, compact disk player, video cameras, electronic parts, various tools, optical equipment and so on can be securely protected from shocks which are possibly caused in transit or storage by use of the wrapping means according to this embodiment.

Figure 23:
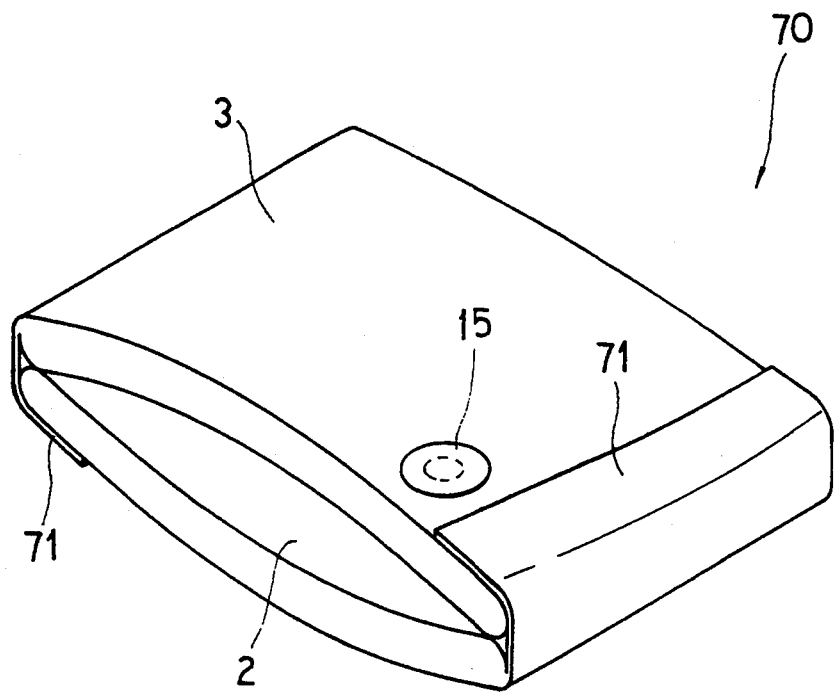
FIG. 23 is a perspective view of a sixth embodiment of the wrapping means of this invention.
Figure 24:
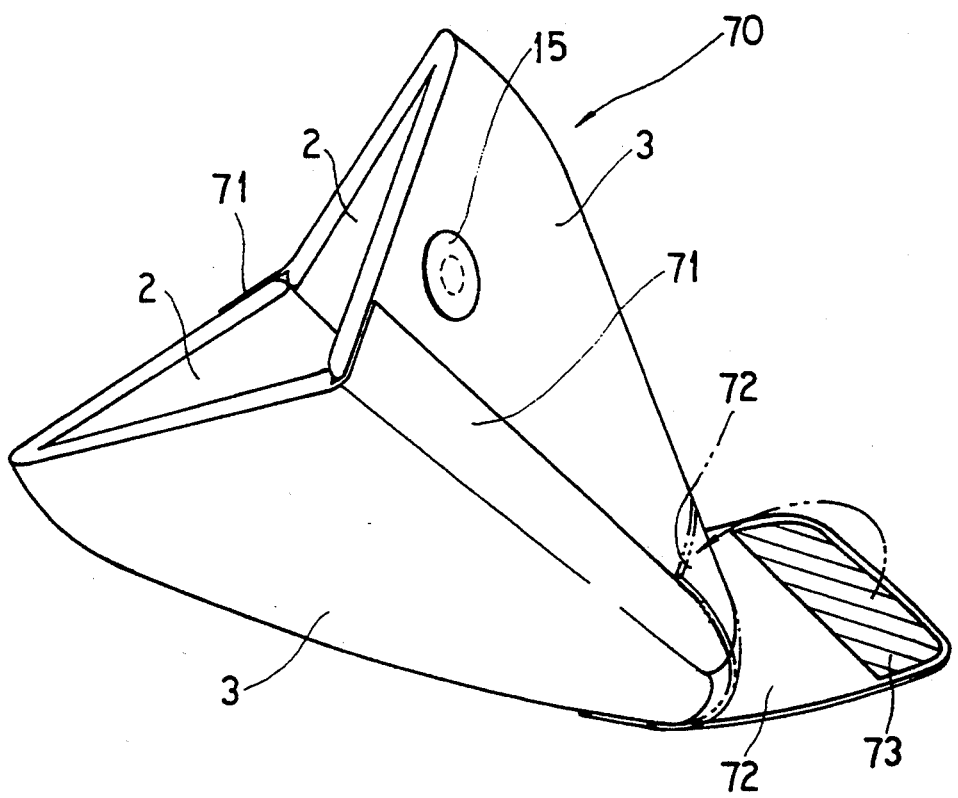
FIG. 24 is a perspective view of the wrapping means of FIG. 23, in its deformed state.

The embodiment shown in FIG. 23 and FIG. 24 uses a wrapping body 70 in the form of an envelope by fastening two lid covers 71 onto the outsides of a twice folded flexible outer membrane 3, and folding back and fastening a bottom cover 72 onto the flexible outer membrane 3 as shown in FIG. 24. The wrapping means according to this embodiment can be suitably applied for wrapping various articles having irregular shapes, bulky articles and so forth.

Figure 25:
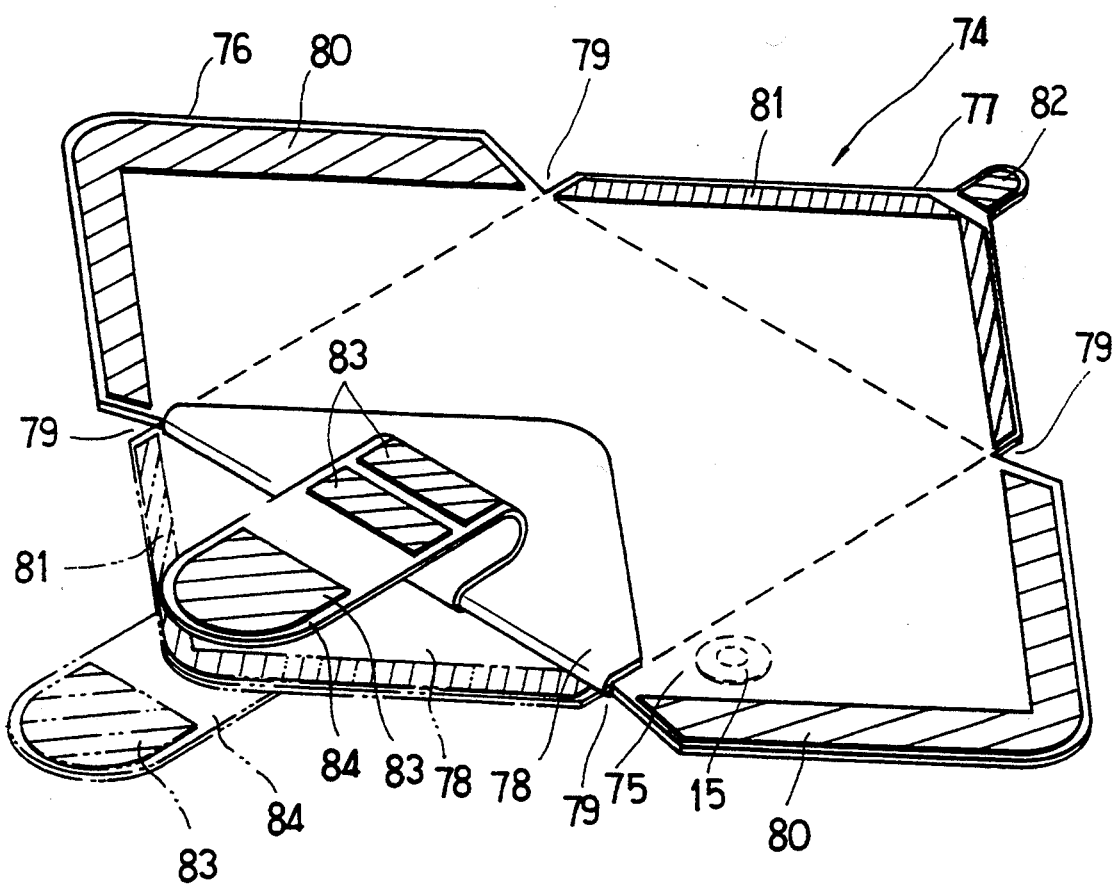
FIG. 25 is a perspective view of a seventh embodiment of the wrapping means of this invention.
Figure 26:
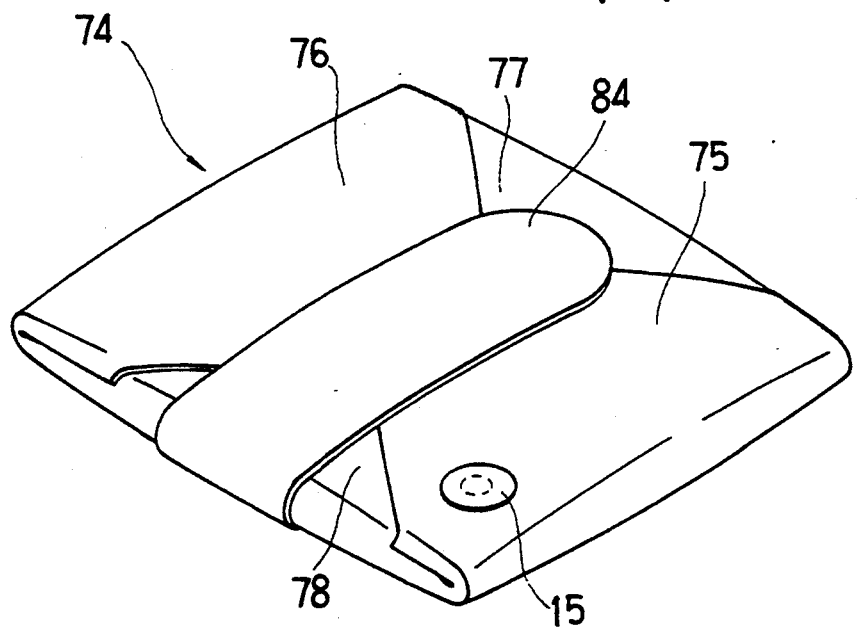
FIG. 26 is a perspective view of the wrapping means of FIG. 25, in use.

The wrapping body 74 of the embodiment shown in FIG. 25 and FIG. 26 comprises a square flexible inner membrane, four lid covers 75–78 shaped as isosceles triangle and attached to four corner portions of the flexible inner membrane, and a belt 84 provided on its inner side with pressure sensitive adhesives 83. Also, the lid covers 75–77 each have pressure sensitive adhesives 80. With the belt 84 and lid covers 75–78 having the pressure sensitive adhesives 80 and 83, the wrapping means of this embodiment can steadily wrap and protect articles of various shapes from shocks.

Figure 27:
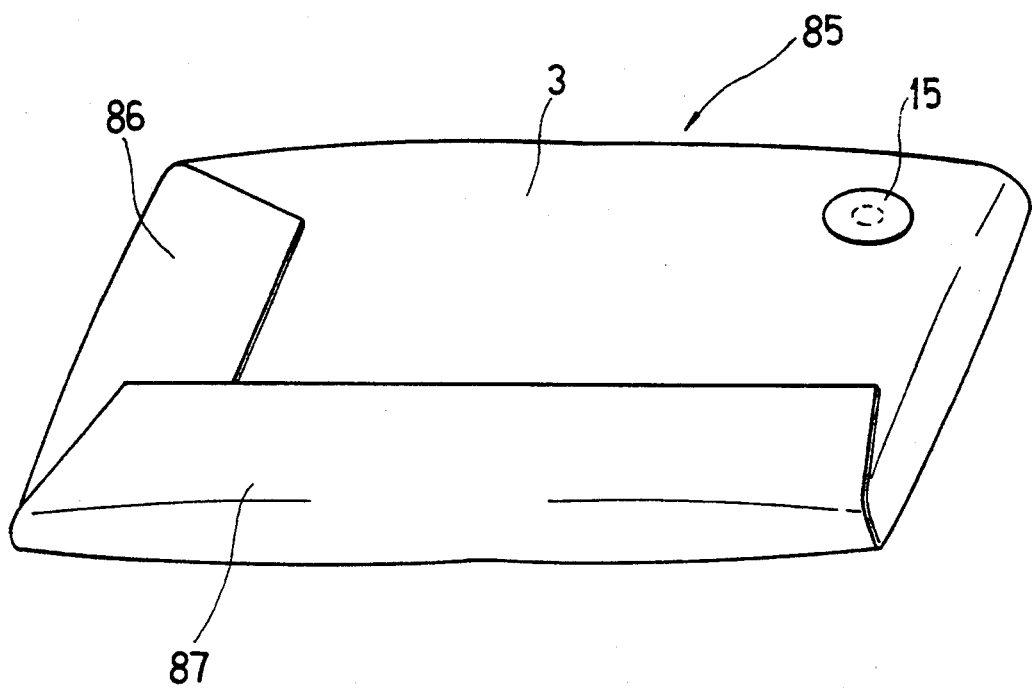
FIG. 27 is a perspective view of an eighth embodiment of this invention.

In the embodiment shown in FIG. 27, a sheet-like wrapping body 85 has side covers 86 and 87. One of the side covers 86 extends outward from a part of one of the longitudinal sides of the wrapping body 85, and the other side cover 87 extends outward from one of the lateral sides of the wrapping body 85. Upon folding the wrapping body 85 in two in the longitudinal direction, the side covers 86 and 87 are folded back and fastened onto the outside of the wrapping body 85 with pressure sensitive adhesives (not shown). The wrapping means according to this embodiment can firmly wrap and protect articles of various shapes from shocks.

Figure 28:
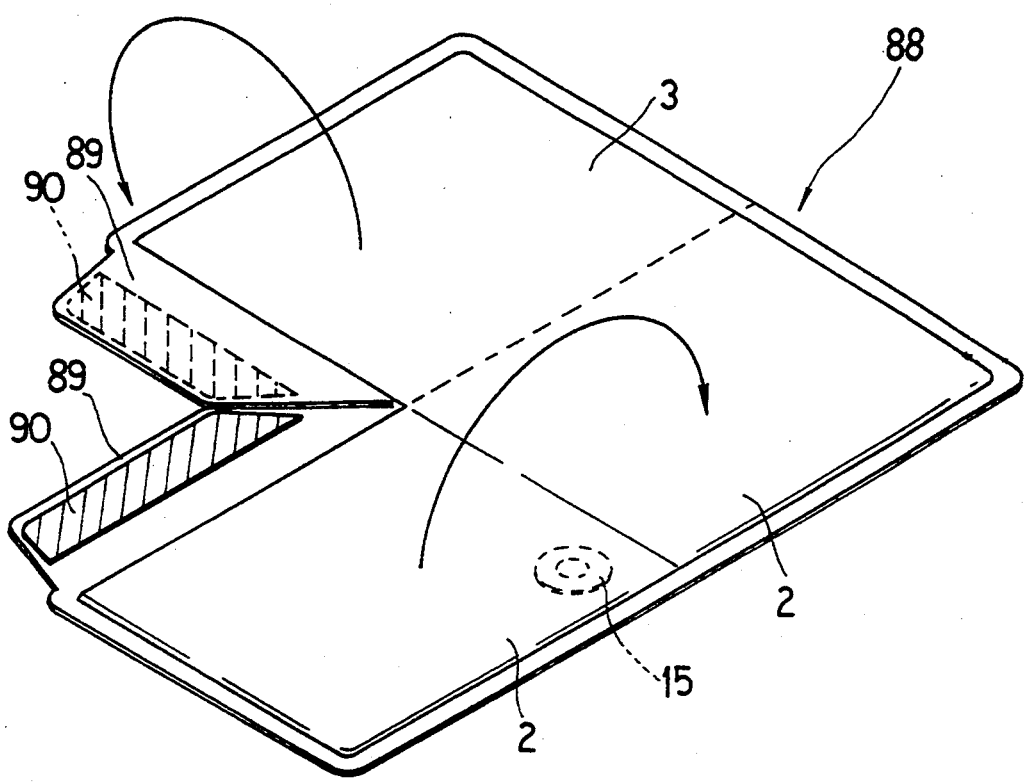
FIG. 28 is a perspective view of a ninth embodiment of the wrapping means of this invention.
Figure 29:
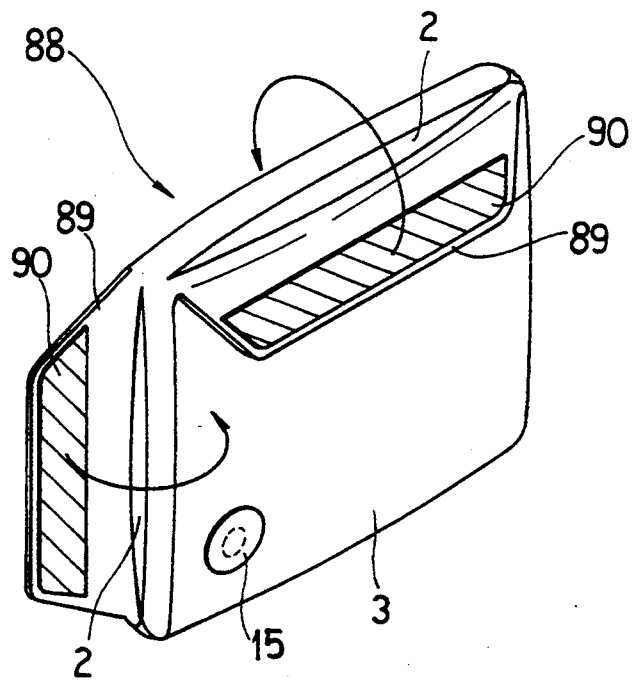
FIG. 29 is a perspective view of the wrapping means of FIG. 28, in use.

In the embodiment shown in FIGS. 28 and 29, a sheet-like wrapping body 88 is formed by arranging three rectangle flexible inner membranes 2 in an "L" shape having lid covers 89 with pressure sensitive adhesives 90.

The wrapping body 88 is folded in three as indicated by the arrows in FIG. 28. The edge portions on both sides of the wrapping body 88 are sealed thermally to form two pockets. The wrapping means having two pockets according to this embodiment can be used conveniently.

Figure 30:
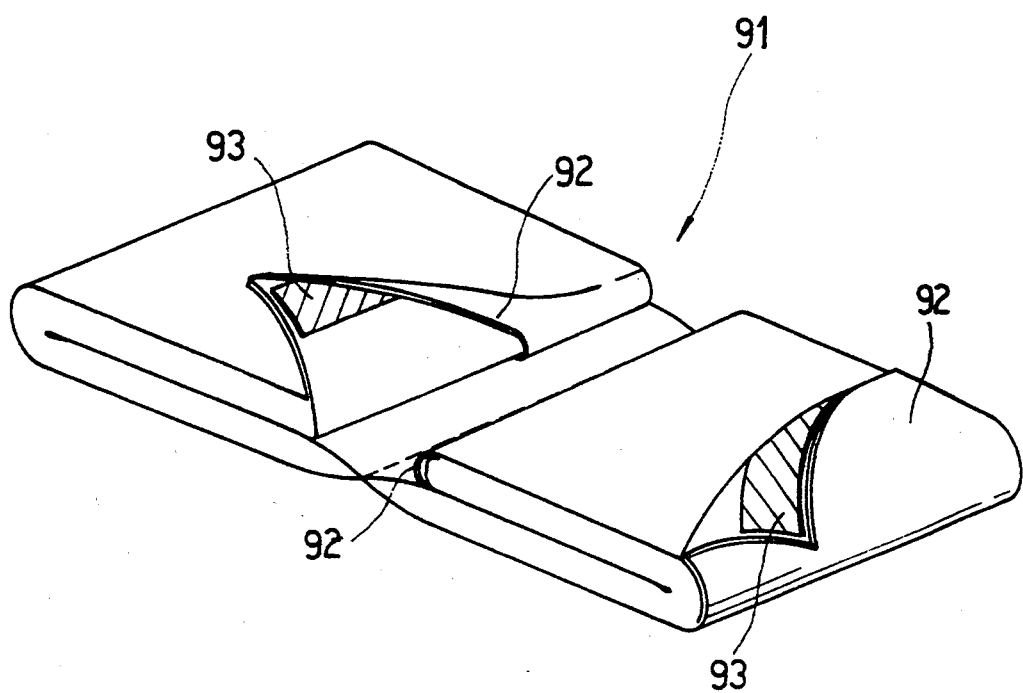
FIG. 30 is a perspective view of a tenth embodiment of the wrapping means of this invention.

The embodiment shown in FIGS. 30 and 31 comprises two wrapping bodies 91 connected to each other and lid covers 92 with pressure sensitive adhesives 93. The wrapping bodies 91 are together bundled up by one cover as shown in FIG. 31. The connected wrapping bodies 91 may be separated as the need arises.

Figure 32:
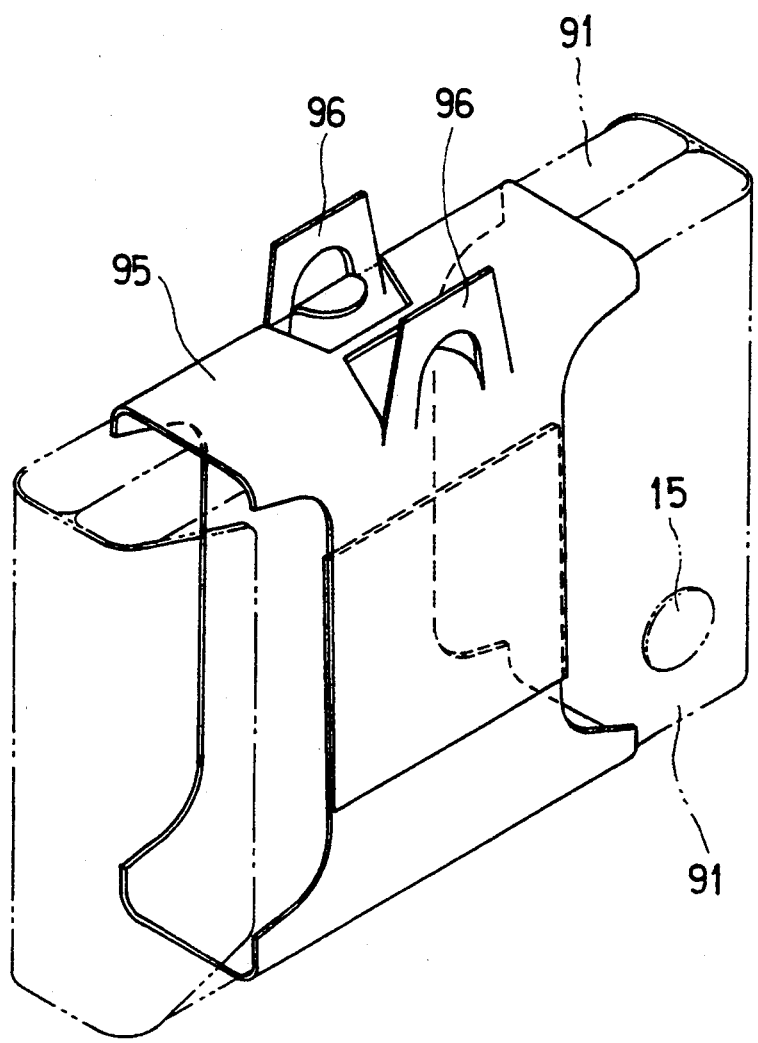
FIG. 32 is a perspective view of an eleventh embodiment of this invention.
Figure 33:
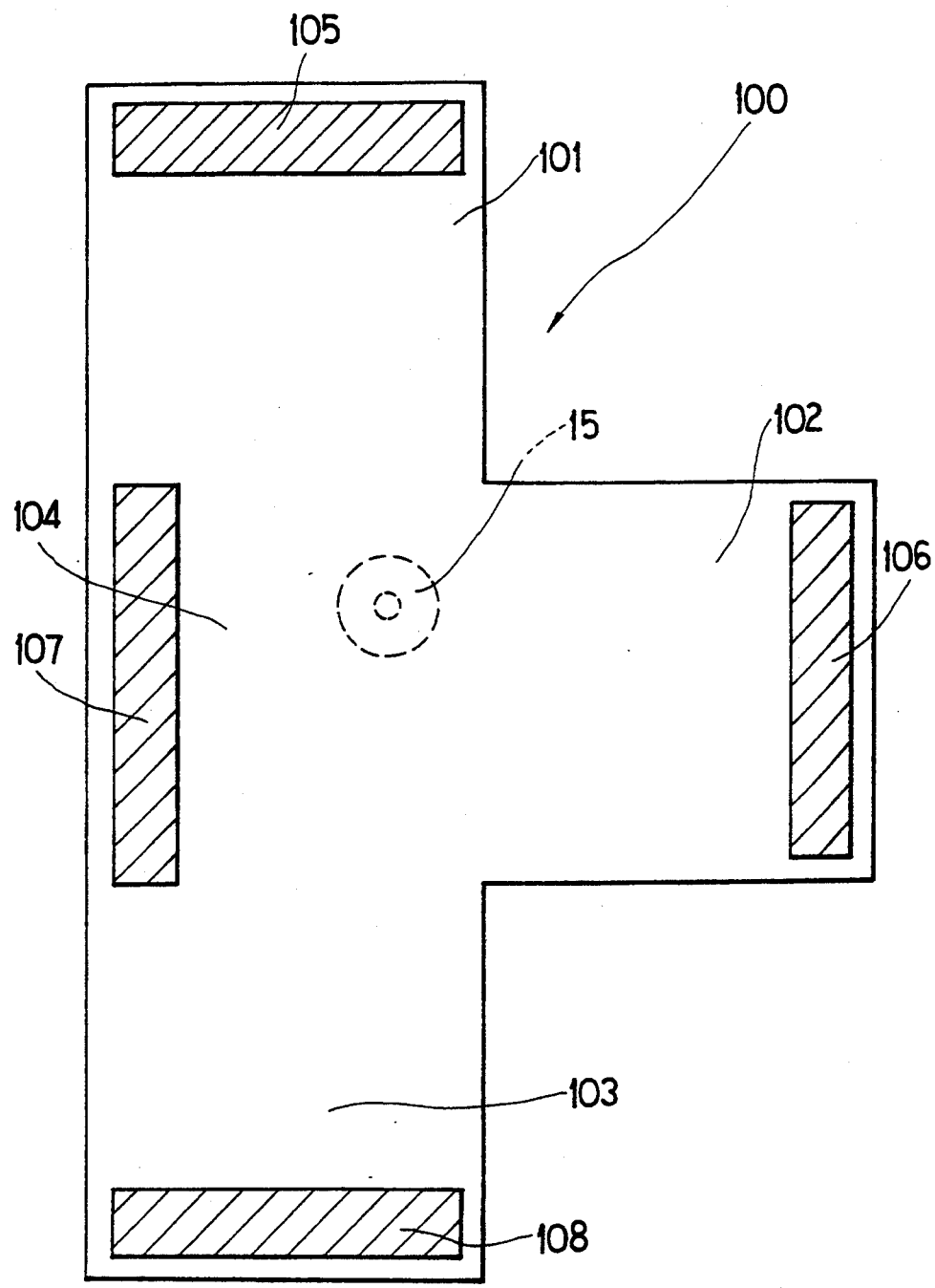
FIG. 33 is a plan view of a twelfth embodiment of the wrapping means of this invention, in its unfolded state.

In the embodiment shown in FIG. 32, for instance, two or more pictures are wrapped side by side with two-folded wrapping body 91 and bound fast with a carrier band 95. According to this wrapping means, the pictures are held firmly by the wrapping bodies which are inflated with air introduced thereinside and can be easily carried by use of handles 96.

FIG. 33 to FIG. 37 show an embodiment of this invention wherein a the sheet-like wrapping body 100 has a substantially T-shape including a central part 104, upper and lower parts 101 and 103 extending upward and downward from the central part 104, and a side part 102 extending laterally from one side of the central part 104. Also, the parts 101–104 have adhesive straps 105–108 on the peripheral side portions thereof.

Figure 34:
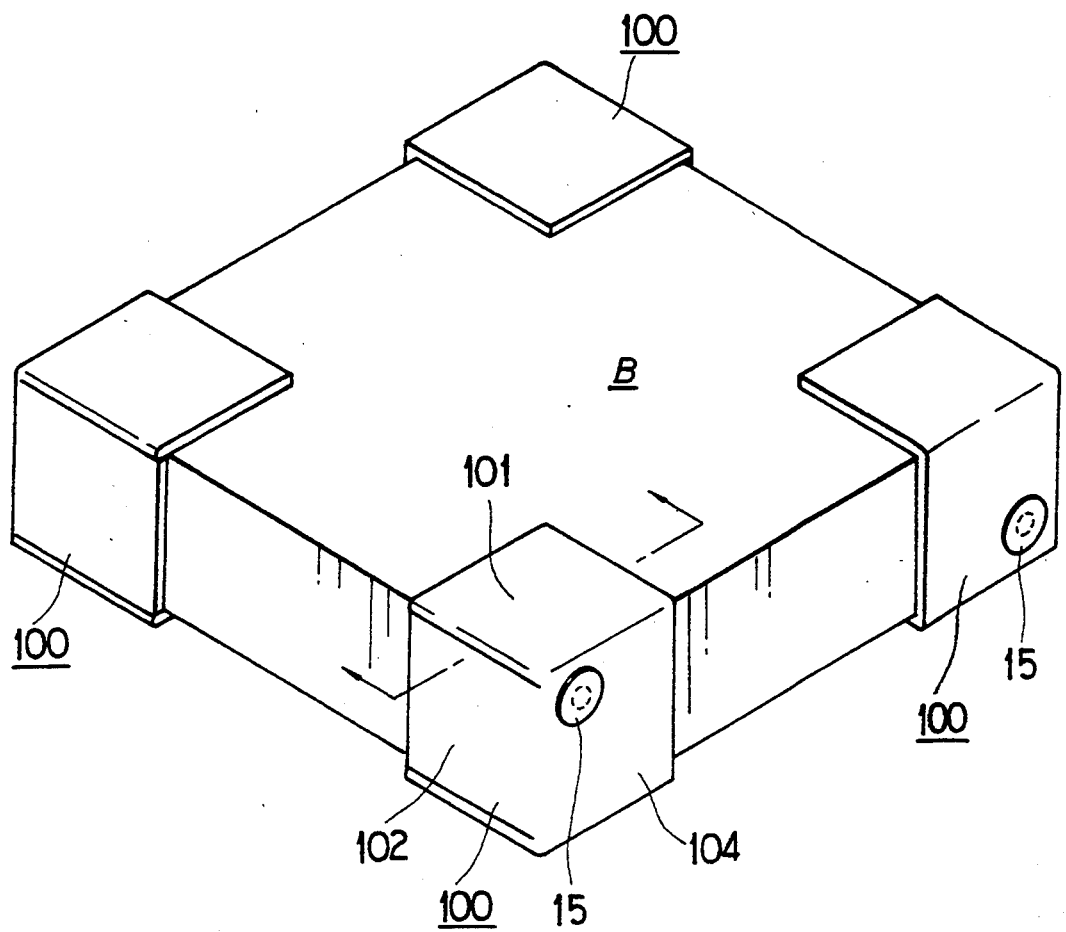
FIG. 34 is a perspective view showing a state in which the corners of an article are protected by the wrapping means of FIG. 33.
Figure 35:
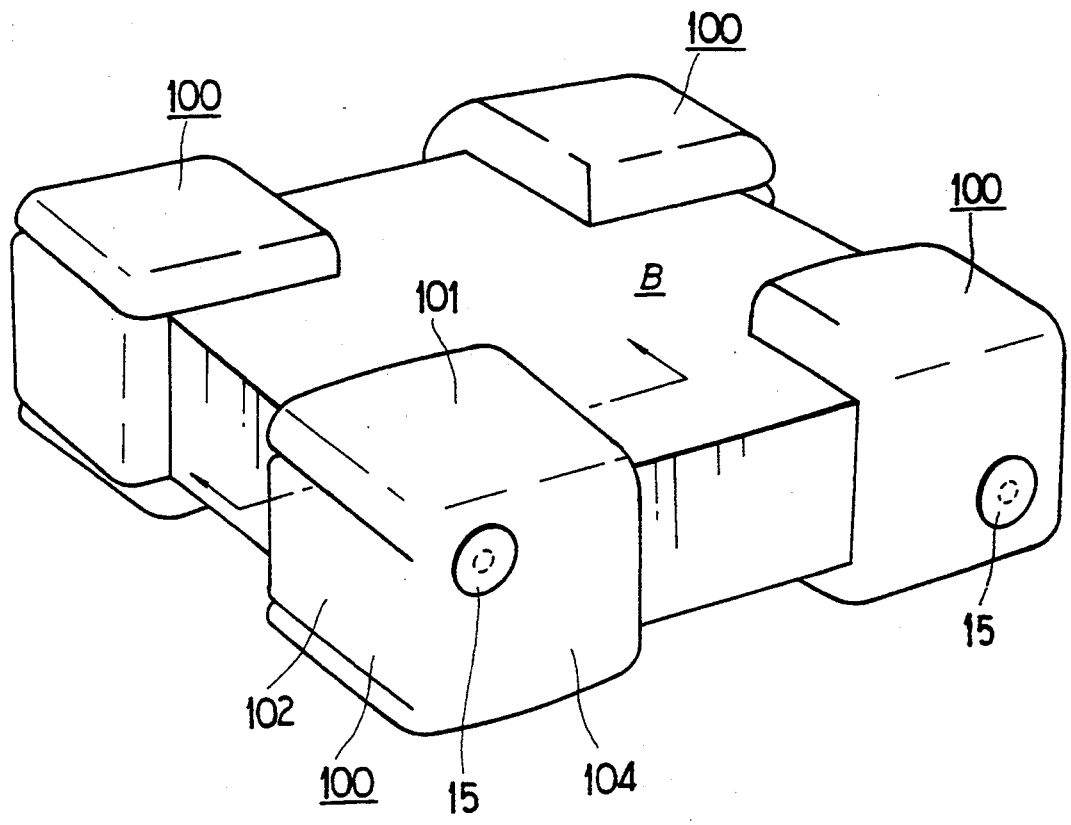
FIG. 35 is a perspective view of the wrapping means of FIG. 34, in its inflated state.
Figure 36:
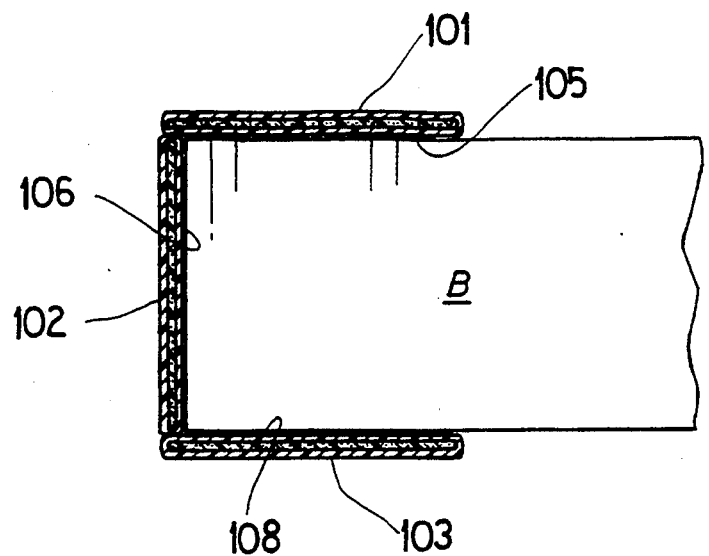
FIG. 36 is a partially sectional view of FIG. 34.
Figure 37:
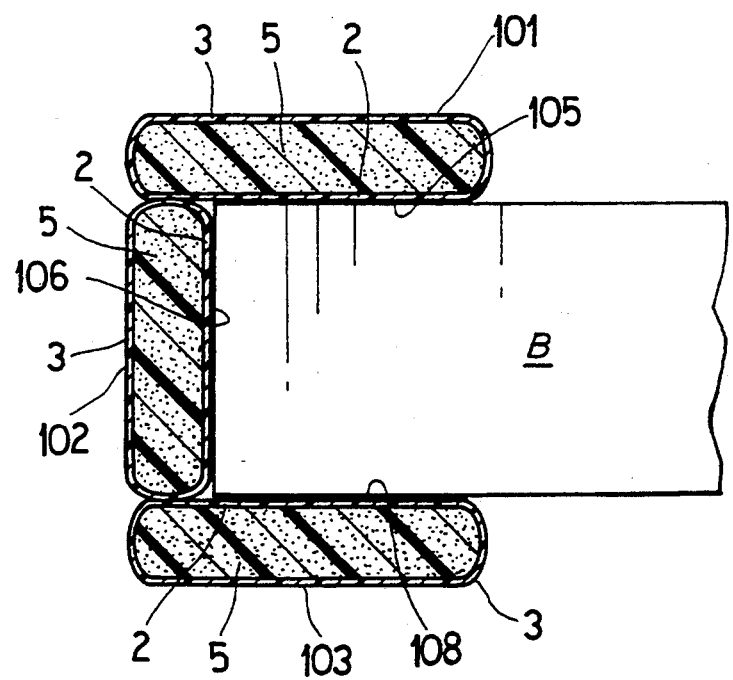
FIG. 37 is a partially sectional view of FIG. 35.

The wrapping means of this embodiment can protect the corner of a squarish article B as shown in FIG. 34 by attaching the wrapping body 100 to the corner of the article B with the adhesive straps 105–108 as shown in FIG. 36, and then opening the air valve 15 to inflate the wrapping body 100 as shown in FIG. 37. By applying four wrapping means to four corners of the article B, the article B can be protected without being covered entirely.

Figure 38:
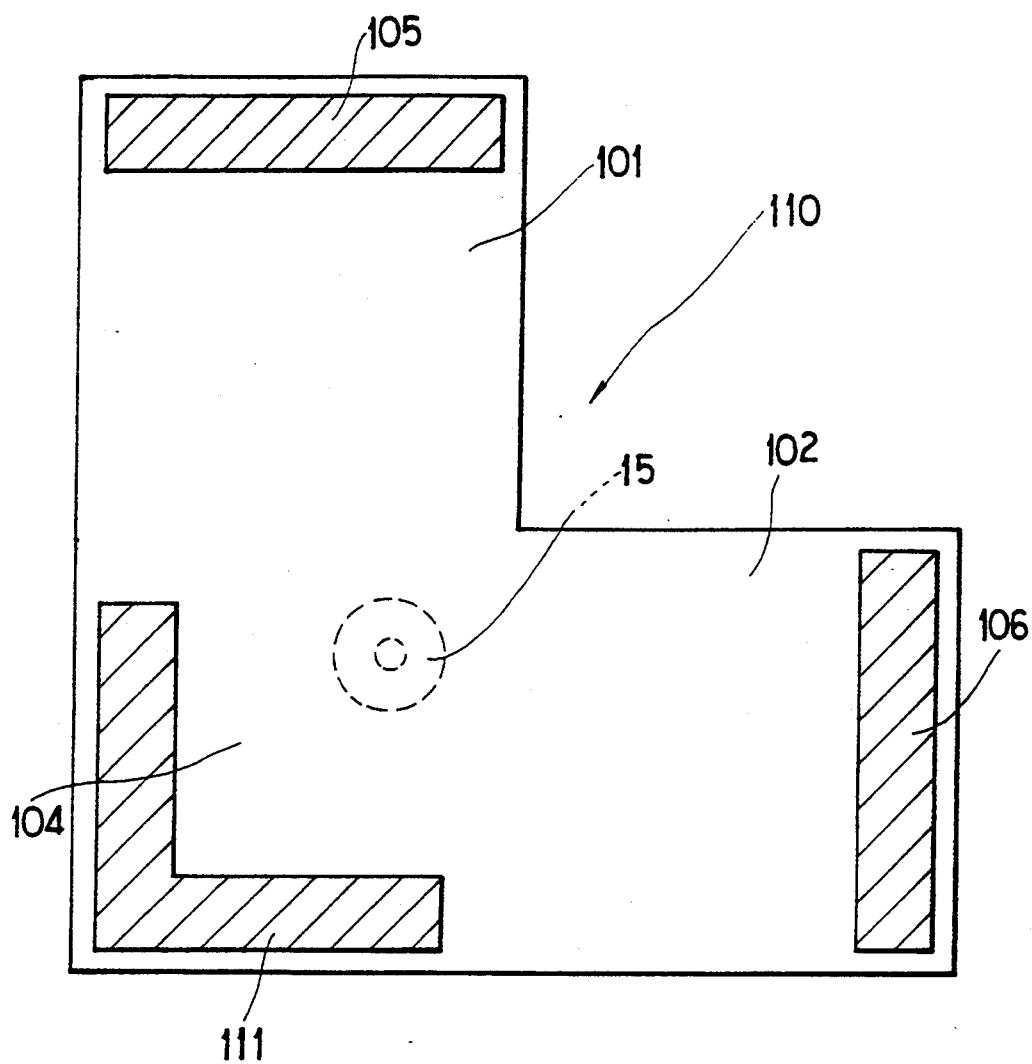
FIG. 38 is a plan view of a thirteenth embodiment of the wrapping means of this invention.

FIG. 38 and FIG. 39 show an embodiment in which a substantially L-shaped wrapping body 110 has a central part 104, an upper part 101 and a side part 102. These parts 104, 101 and 102 have adhesive straps 105, 106 and 111, respectively. According to this embodiment, the six corners of a substantially cubic article C can be protected in safety as shown in FIG. 39 by attaching each wrapping body 110 to a respective corner of the article C with the adhesive straps and opening the air valve 15 to introduce air into a cavity in the wrapping body, thus inflating the wrapping body 110.

Figure 40:
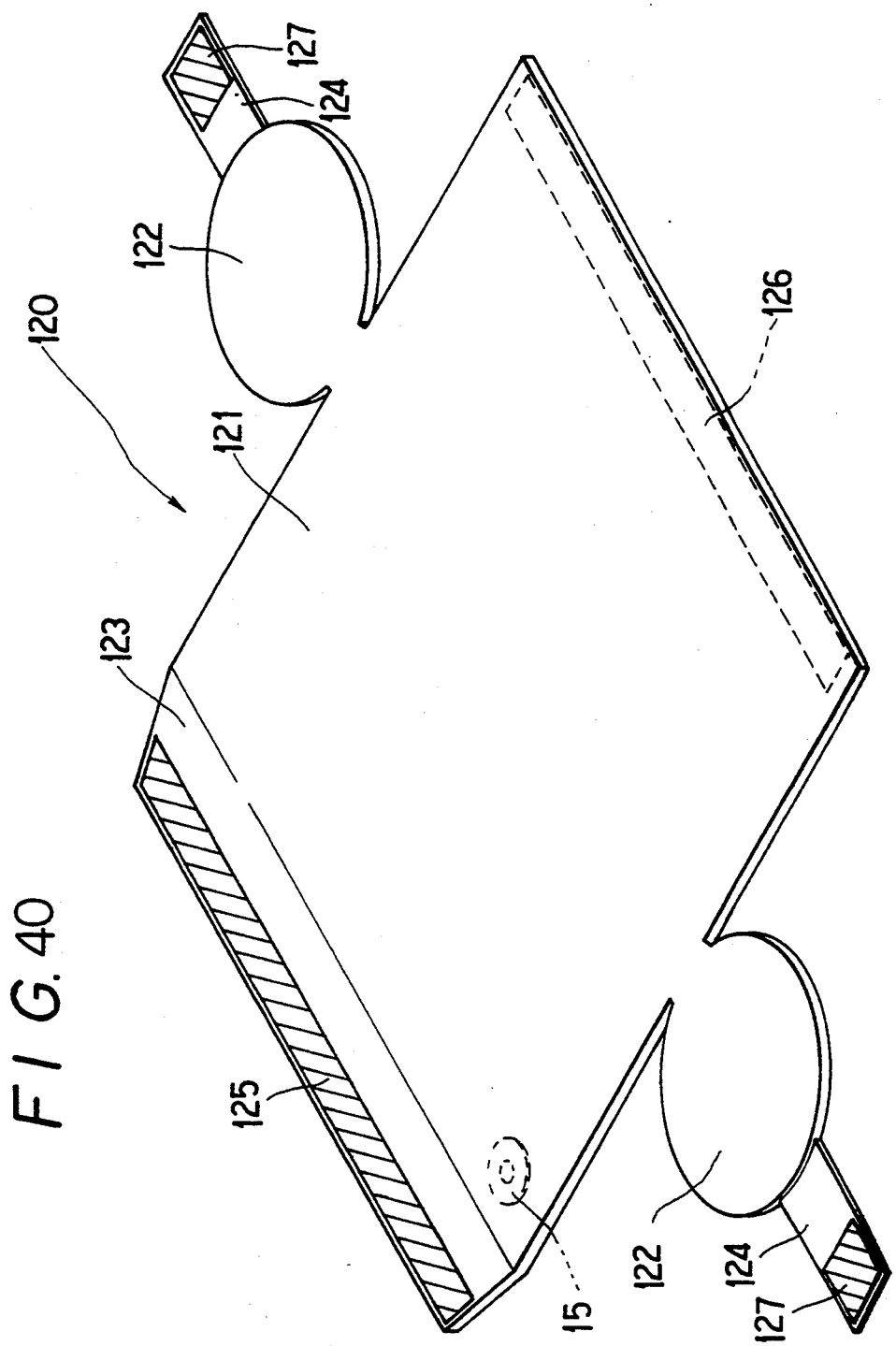
FIG. 40 is a perspective view of a fourteenth embodiment of the wrapping means of this invention.
Figure 41:
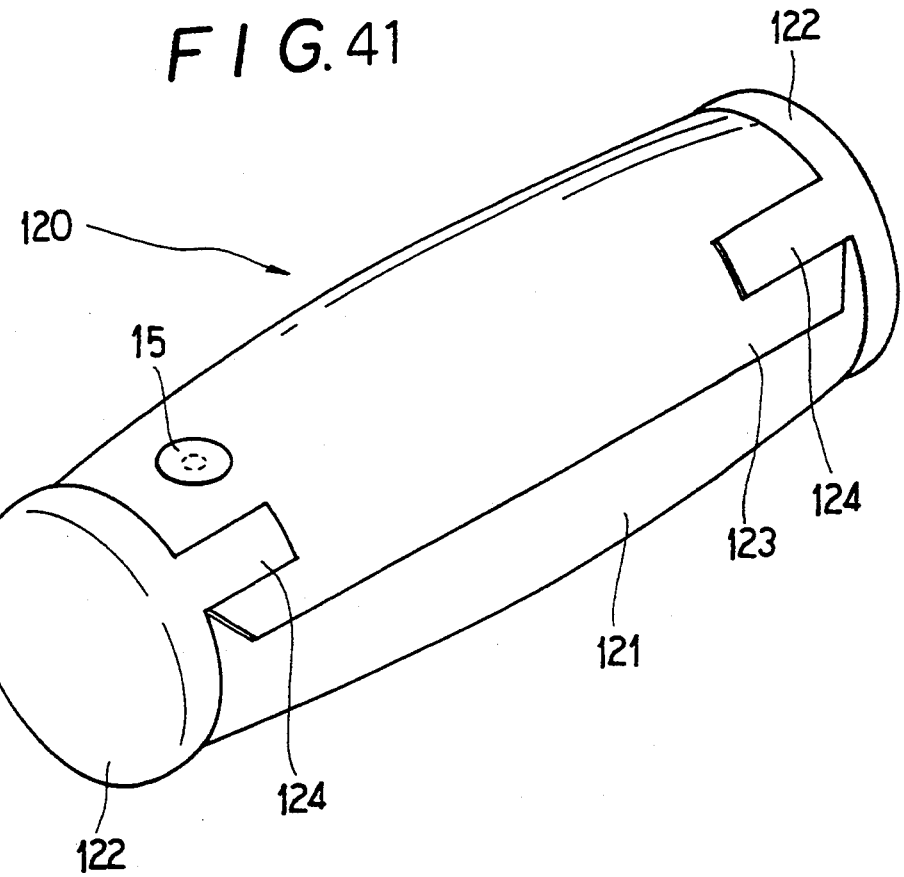
FIG. 41 is a perspective view of the wrapping means of FIG. 40, in use.
Figure 42:
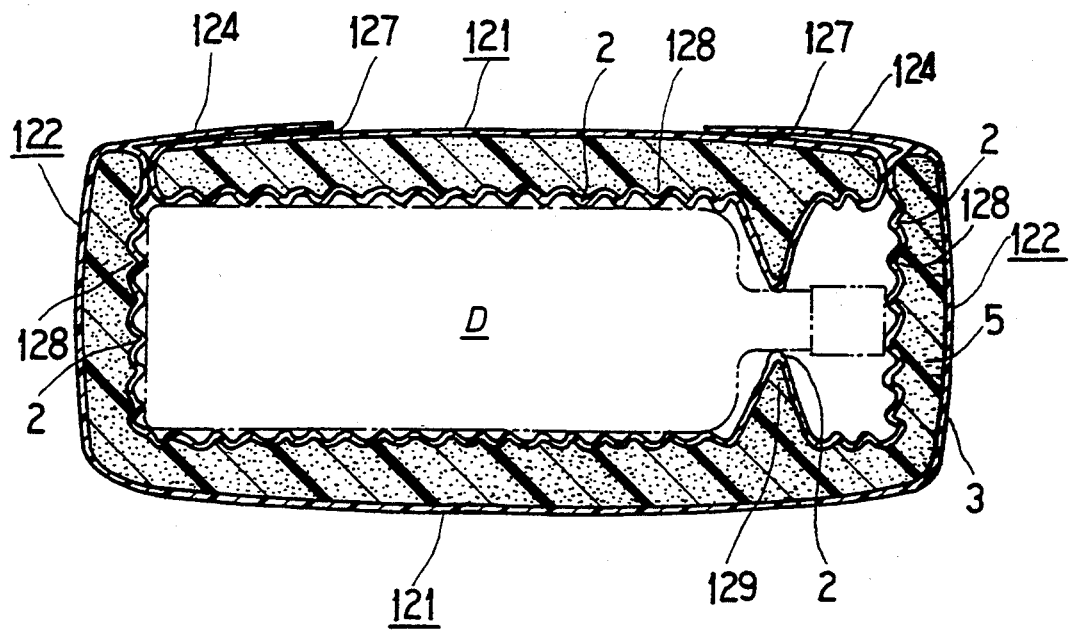
FIG. 42 is a sectional view of FIG. 41.

FIG. 40 to FIG. 42 show an embodiment comprising a wrapping body 120 having a substantially square shape. The wrapping body 120 has a central part 121, a cover flap 123 with pressure sensitive adhesive 125, and round-shaped side pads 122 with fastening strips 124 extending from the central part 121. The central part 121 of the wrapping body is applied with pressure sensitive adhesive 126 along the free end portion on the outer surface of the wrapping body 120.

Central Part 121 of wrapping body 120 is first rolled up around an article D and fixed with the pressure sensitive adhesives 125, 126. The end faces of the roll thus obtained are covered with the side pads 122 which are fastened by the fastening straps 124. Then, by opening the air valve 15, air is introduced into the cavity in the wrapping body to cause cushion material 5 placed in the cavity to expand. By making the inner surface of the sponge foam material 5 uneven as shown in FIG. 42, the flexible inner membrane 2 becomes ragged or deformed to increase the sliding friction thereof. Thus, with the cushion material 5 having a protuberant portion 129, the article D such as a bottle having a neck part can be securely held.

Figure 43:
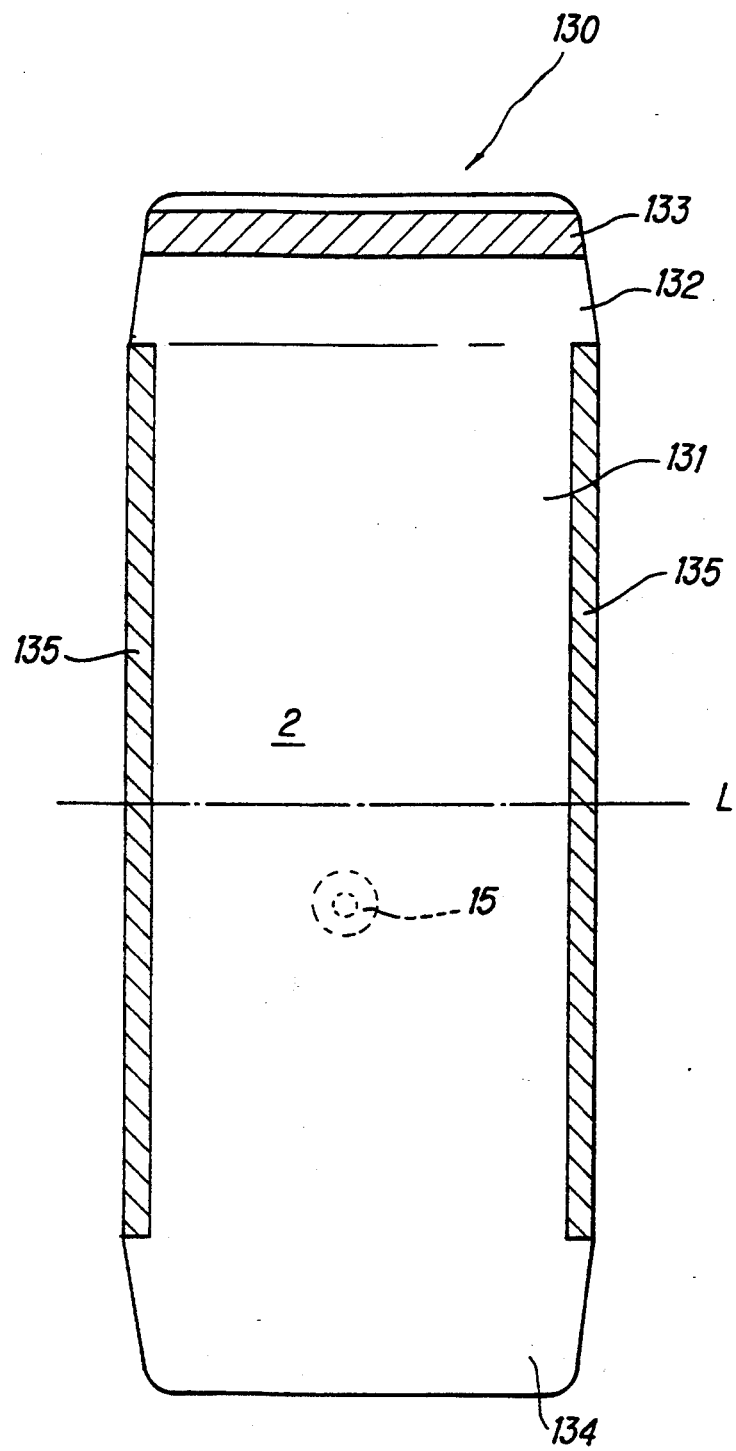
FIG. 43 is a plan view of a fifteenth embodiment of the wrapping means of this invention.
Figure 44:
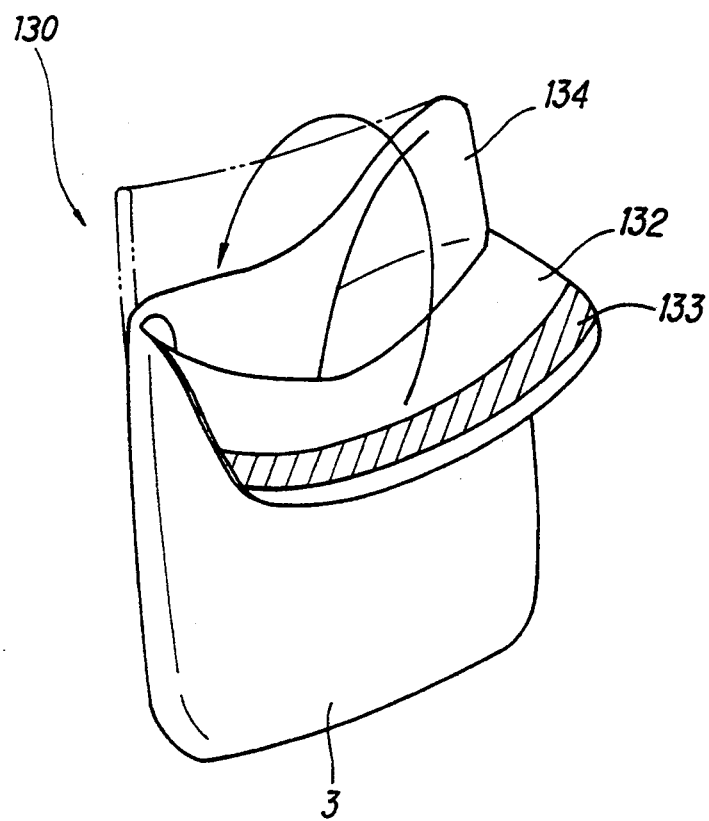
FIG. 44 is a perspective view of the wrapping means of FIG. 43, in a state shaped in a bag.
Figure 45:
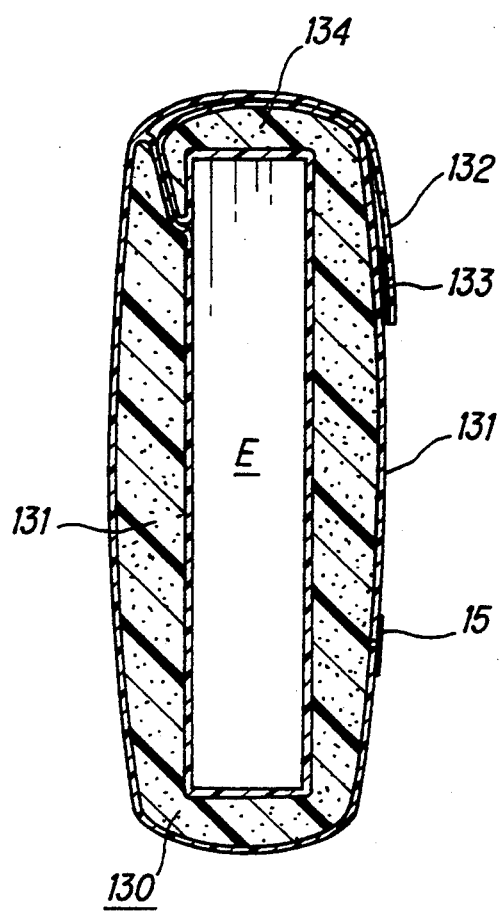
FIG. 45 is a sectional view of FIG. 44.

FIG. 43 through FIG. 45 show an embodiment in which a sheet-like wrapping body 130 comprises a slender base sheet 131, a lid cover 132 extending from the base sheet 131 in the longitudinal direction, and a folding flap 134. The lid cover 132 is provided with pressure sensitive adhesive 133. Along the side edge portions of the base sheet are provided pressure sensitive adhesives 135.

With this wrapping means, an article E such as a compact disk can be well wrapped by first folding the base sheet 131 in two along the center line L, fastening the folded base sheet 131 by the pressure sensitive adhesives 135, tucking the folding flap 134 into the inside of the folded base sheet 131, and lying the lid cover 132 upon the folded base sheet 131. Then, the air valve 15 is opened to introduce air into the cavity in the wrapping body 130, allowing the cushion material 5 to expand in the cavity. Thus, the article E is entirely protected.

Figure 46:
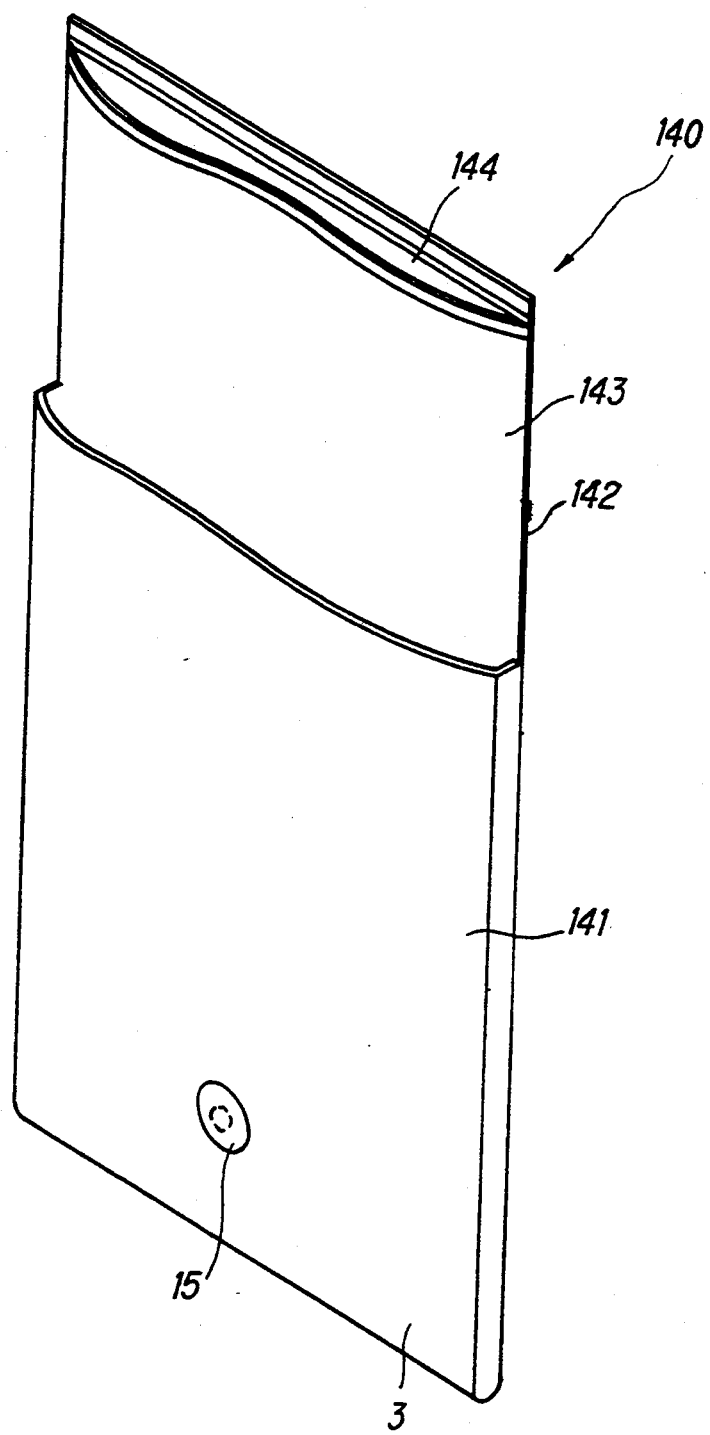
FIG. 46 is a perspective view of a sixteenth embodiment of the wrapping means of this invention.
Figure 47:
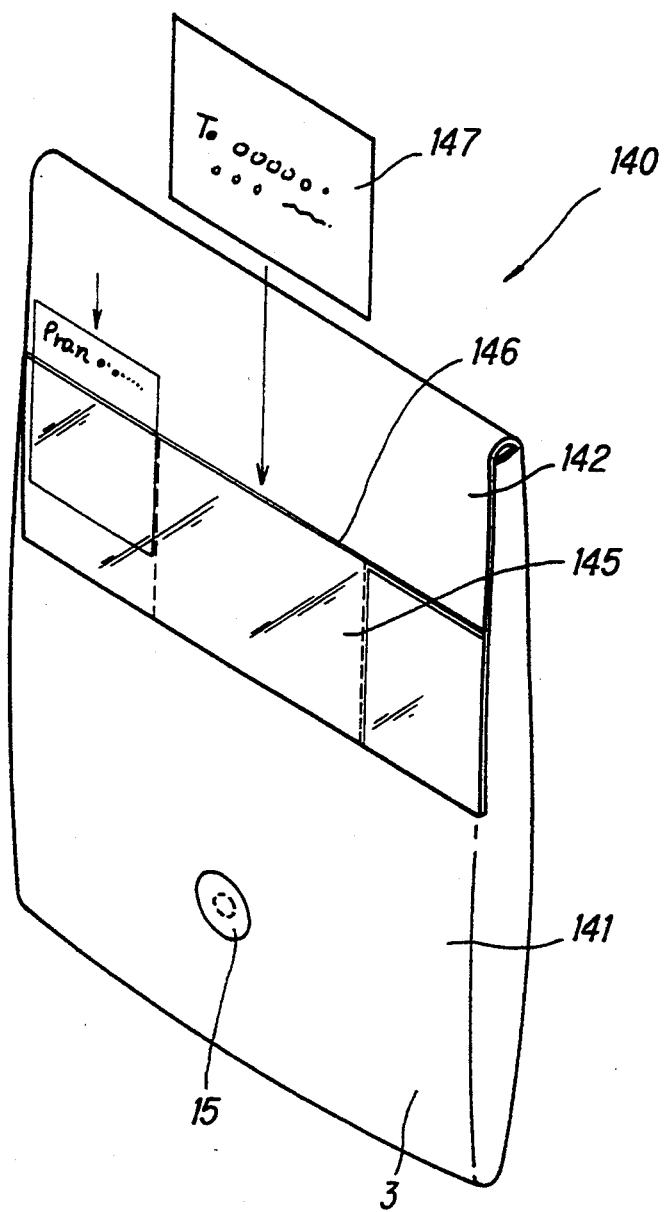
FIG. 47 is a perspective view of the wrapping means of FIG. 46, in use.
Figure 48:
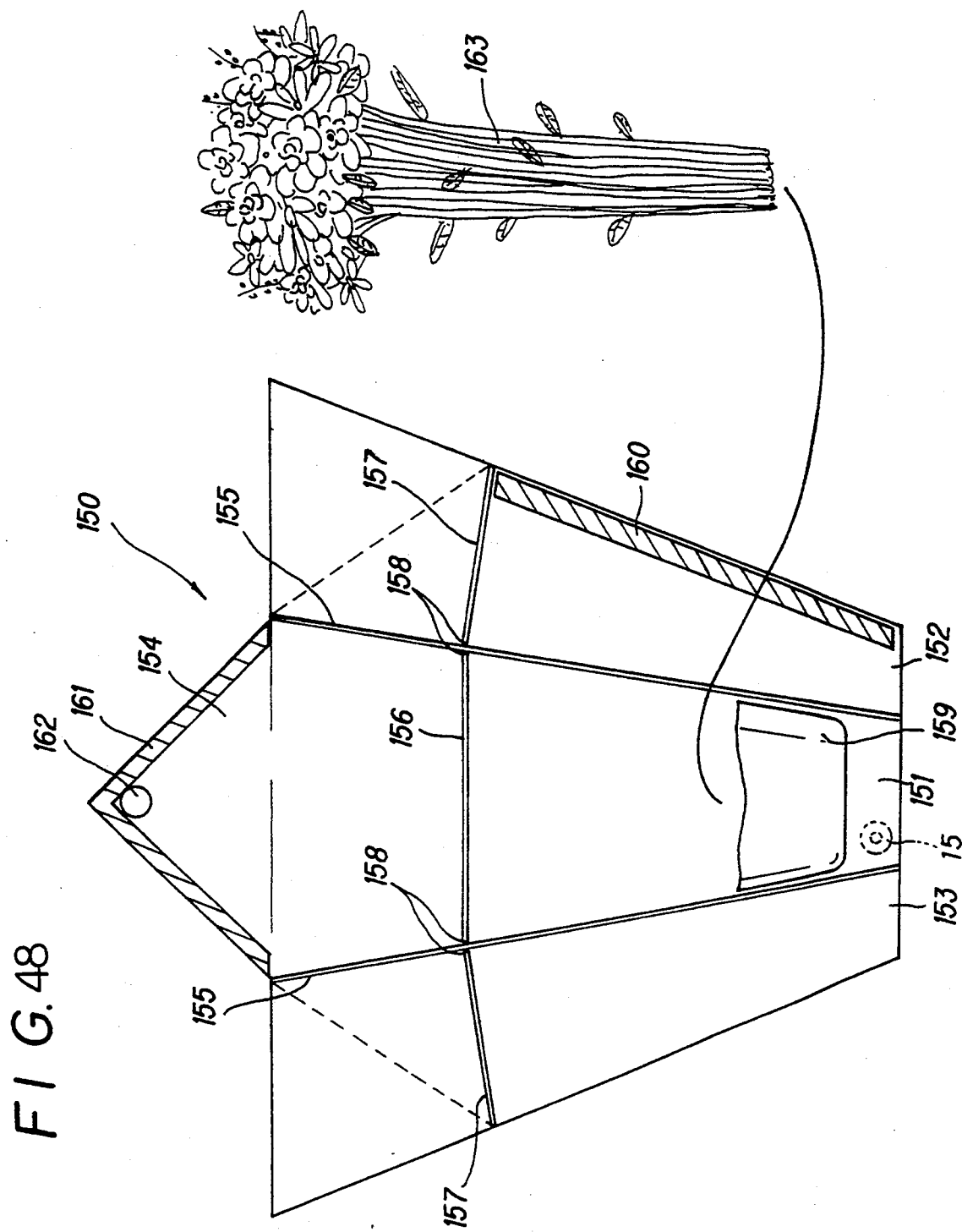
FIG. 48 is a plan view of a seventeenth embodiment of the wrapping means of this invention.

The embodiment shown in FIG. 46 and FIG. 47 comprises a sheet-like wrapping body 140 having a slender base sheet 141 similar to that in the aforementioned embodiment, which is folded and shaped as an envelope. The wrapping body 140 has a second bag member a pocket 144 formed of a folding portion 142 extending from the base sheet 141, and a film sheet 143 attached to the folding portion 142. The folding portion 142 is laminated on its outer side with a transparent film 145 to form a pocket 146 for a postcard or the like.

This wrapping means has the auxiliary pockets 144 and 146 for containing small articles such as a postcard in addition to an envelope-like space mainly formed inside the wrapping body 140 for accommodating postal matter or the like.

FIG. 48 through FIG. 51 show an embodiment in which a sheet-like wrapping body 150 comprises a base sheet 151 which is generally shaped in a substantially inverted truncated pyramid, side sheets 152 and 153 extending laterally from the base sheet 151, and a cover 154 extending upward from the base sheet 151. These sheets 151–153 may be preferably provided with vertical reinforcing frameworks 155 and horizontal reinforcing frameworks 156 and 157. The horizontal reinforcing frameworks 156 and 157 are slightly separated at points of intersection between the vertical reinforcing framework 155 and the horizontal reinforcing framework 156, 157 so as to easily fold and to enable the side sheets 152 and 153 to lie along the base sheet 151.

The side sheet 152 has pressure sensitive adhesive 160. The cover 154 has pressure sensitive adhesive 161 and is provided in the top portion thereof with a hook hole 162. The base sheet 151 has a pocket 159.

Figure 49:
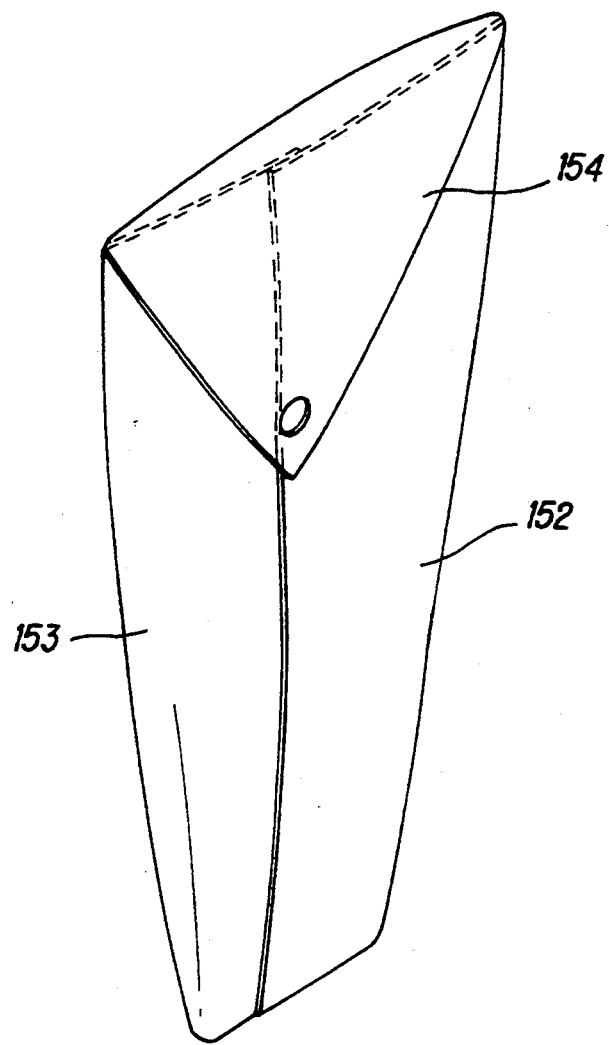
FIG. 49 is a perspective view of the wrapping means of FIG. 48, with a lid cover closed.
Figure 50:
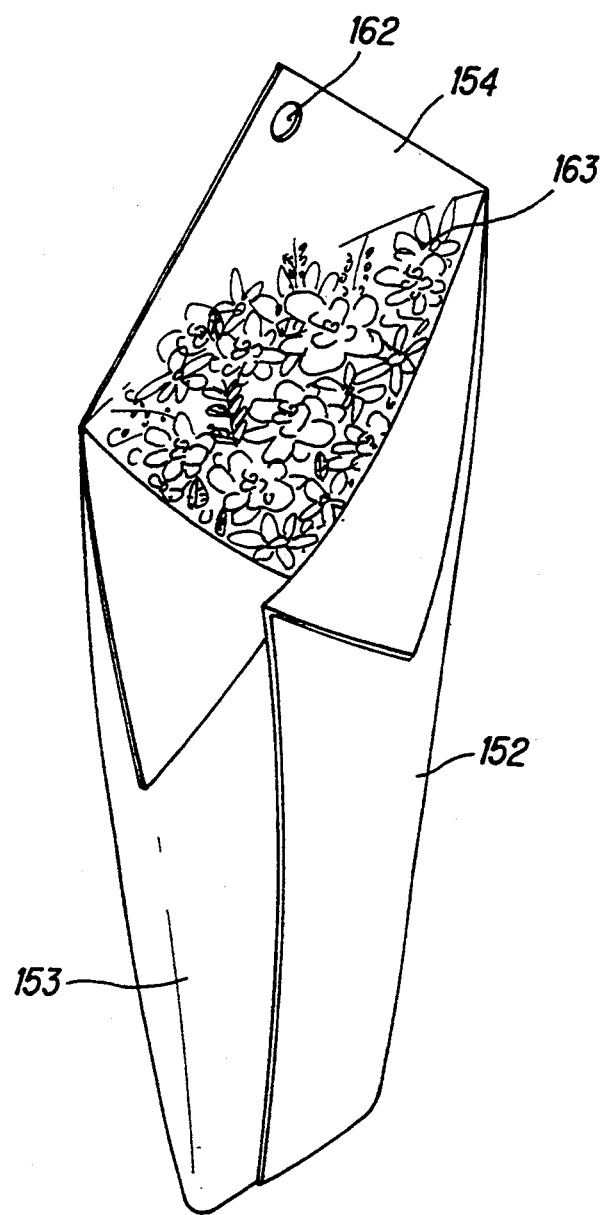
FIG. 50 is a perspective view of the wrapping means of FIG. 48, with the lid cover opened.

When the wrapping means is used for wrapping a bunch of flowers 163, the flowers are first laid on the base sheet 151 with the roots or stalks inserted into the pocket 159, and the side sheets 152 and 153 are folded onto the flowers and the base sheet 151. Finally, by folding downward the cover 154 to cover the petals of flowers as shown in FIG. 49, the flowers are entirely wrapped. Thus, the flower package obtained can be retained securely by means of the pressure sensitive adhesives 160 and 161 applied on the side sheet 152 and cover 154 and by opening the air valve 15 to introduce air into the inside of the wrapping body, thereby inflating the wrapping body.

Figure 51:
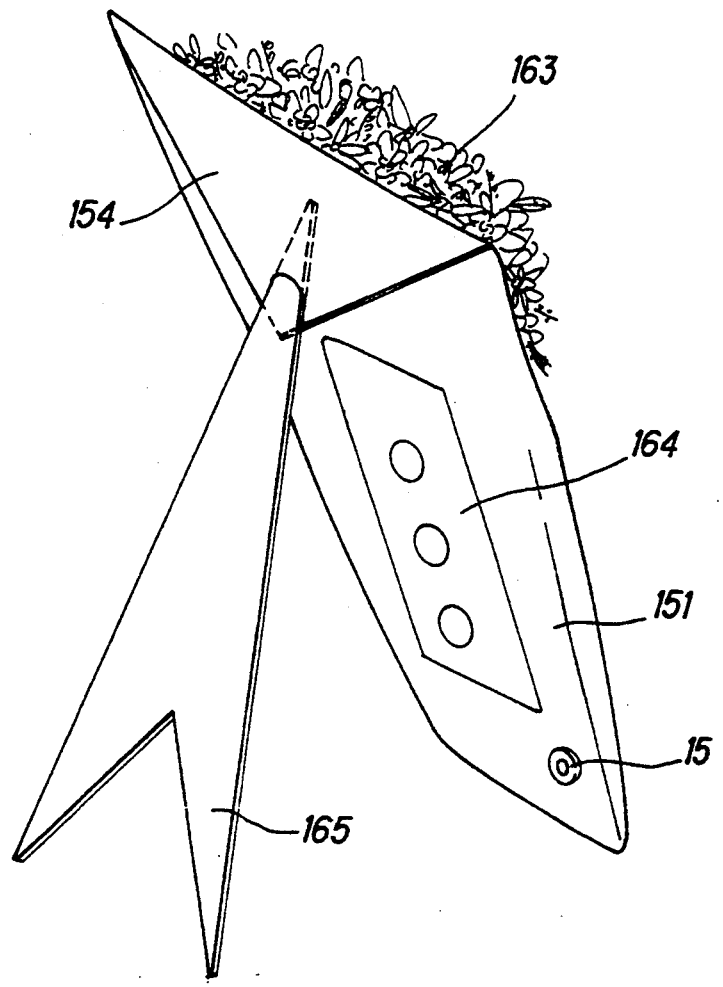
FIG. 51 is a perspective view of the wrapping means of FIG. 48, in a standing state.

According to this embodiment, the bunch of flowers can be displayed as wrapped with the wrapping means of this invention by opening the cover 154 and hanging the wrapping means by use of the hole 162 formed in the cover 154. By inserting a supporter 165 through the hole 162 formed in the cover 154 as shown in FIG. 51, the wrapping means can be used as a flower stand.

Figure 52:
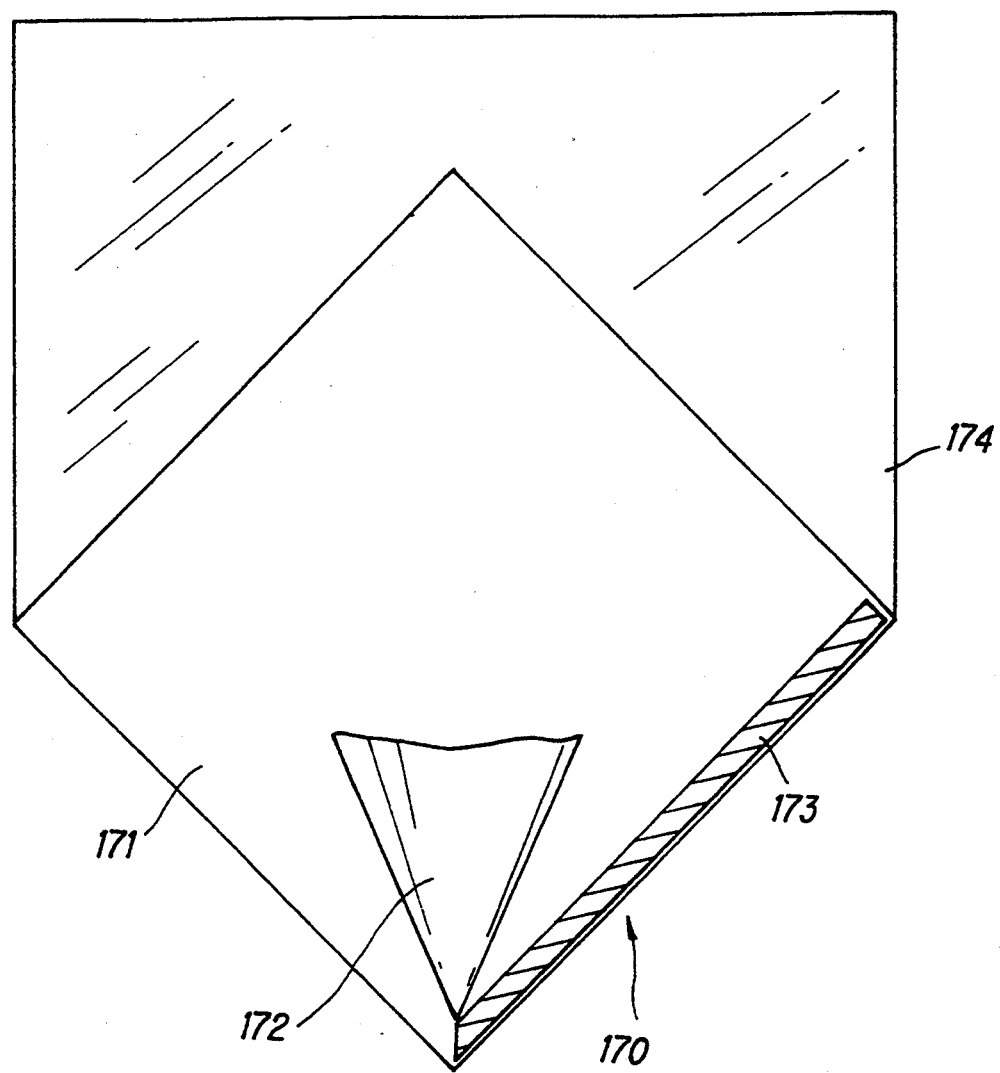
FIG. 52 is a plan view of an eighteenth embodiment of the wrapping means of this invention.
Figure 53:
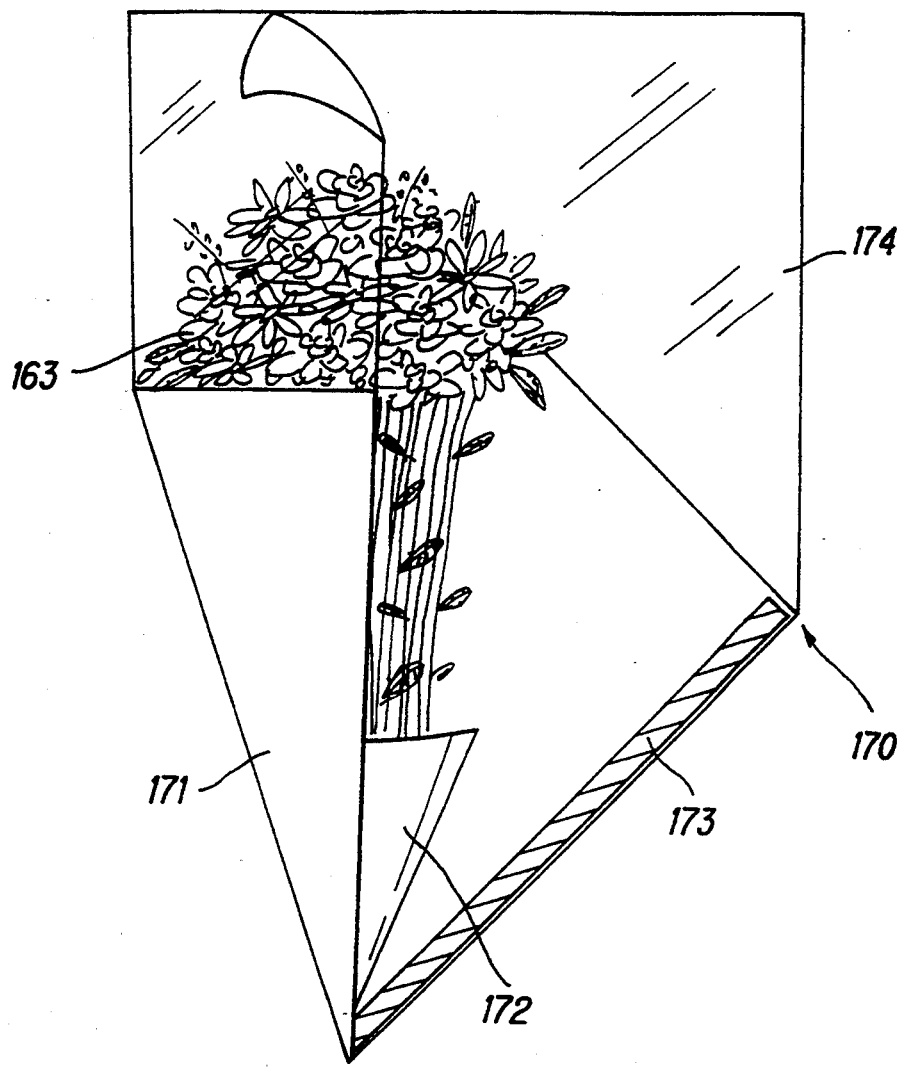
FIG. 53 is a plan view of FIG. 52, showing the process in which an article is wrapped.
Figure 54:
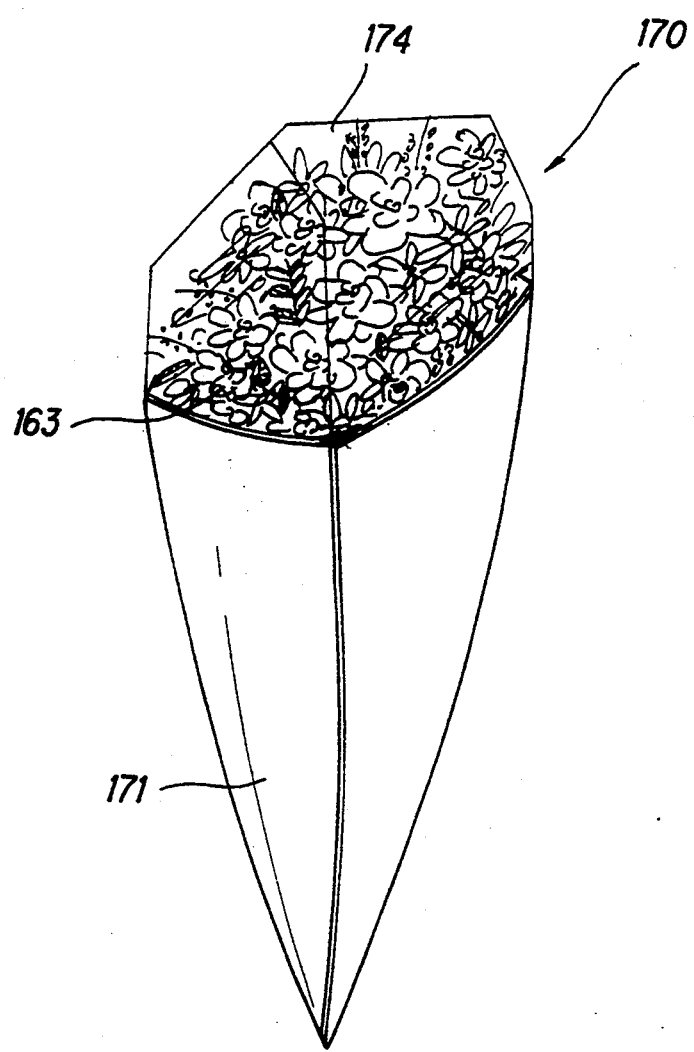
FIG. 54 is a perspective view of the wrapping means of FIG. 52, in use.

FIG. 52 to FIG. 54 show the an embodiment in which a wrapping body 170 comprises a base sheet 171 formed in a lozenge shape and having a pressure sensitive adhesive strap 173 attached to one lower oblique side of the lozenge-shaped base sheet 171 and a pocket 172 formed on the lower part of the base sheet 171. From the upper oblique sides of the base sheet 171, a cover 174 made of a transparent film extends upward.

When wrapping a bunch of flowers 163 with this wrapping means, the roots or stalks of the flowers are first inserted in the pocket 172, and then, both side parts of the base sheet 171 are folded to lie on the central part of the base sheet as shown in FIG. 53. Then, the transparent cover 174 is folded on the base sheet 171 to cover the petals of flowers, and finally, air is introduced into the inside of the wrapping body 170 to inflate the wrapping means. Thus, the wrapping means of this embodiment can be used as a flower case and the flowers can be displayed as wrapped as shown in FIG. 54.

Figure 55:
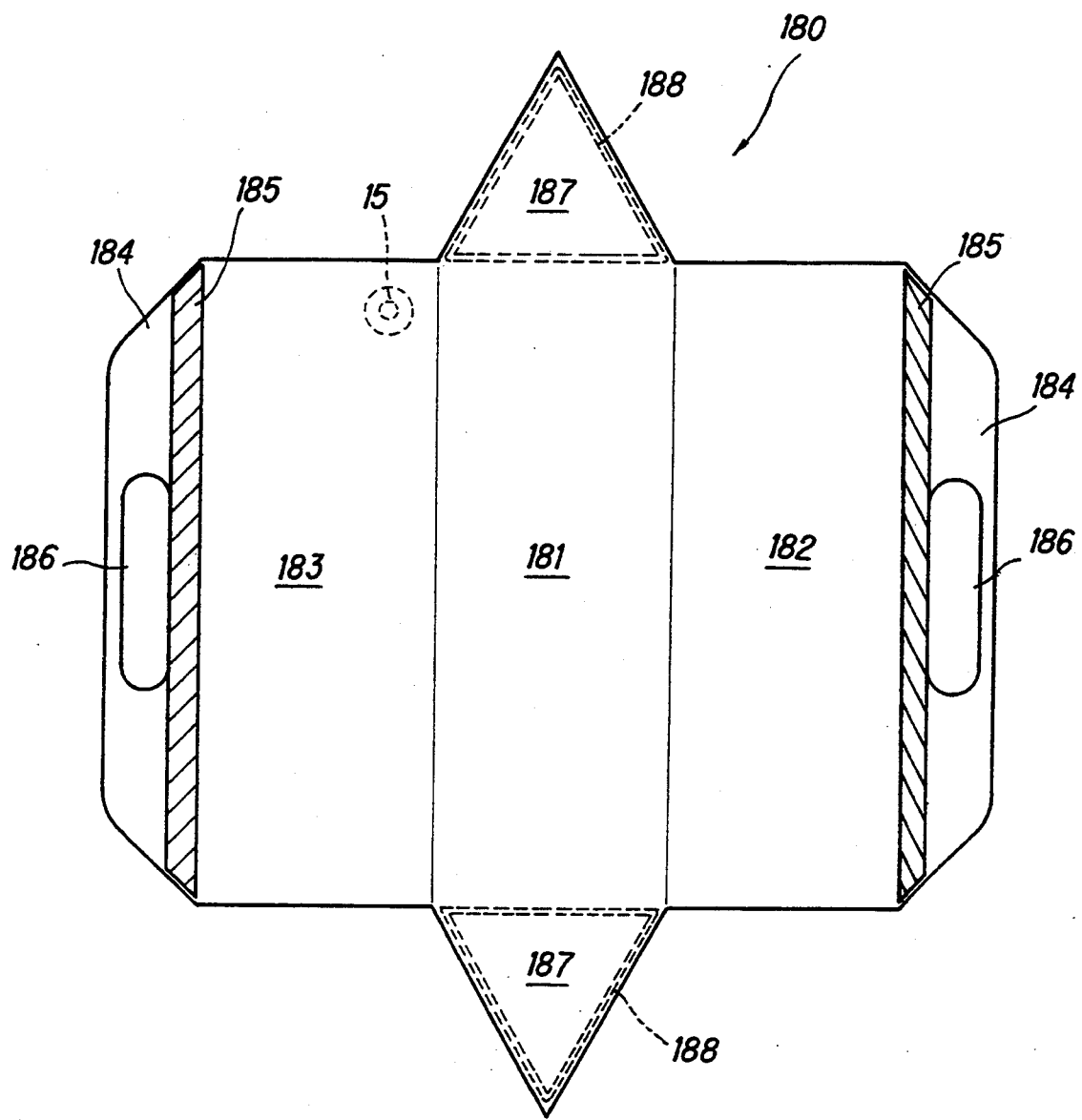
FIG. 55 is a plan view of the a nineteenth embodiment of the wrapping means of this invention.
Figure 56:
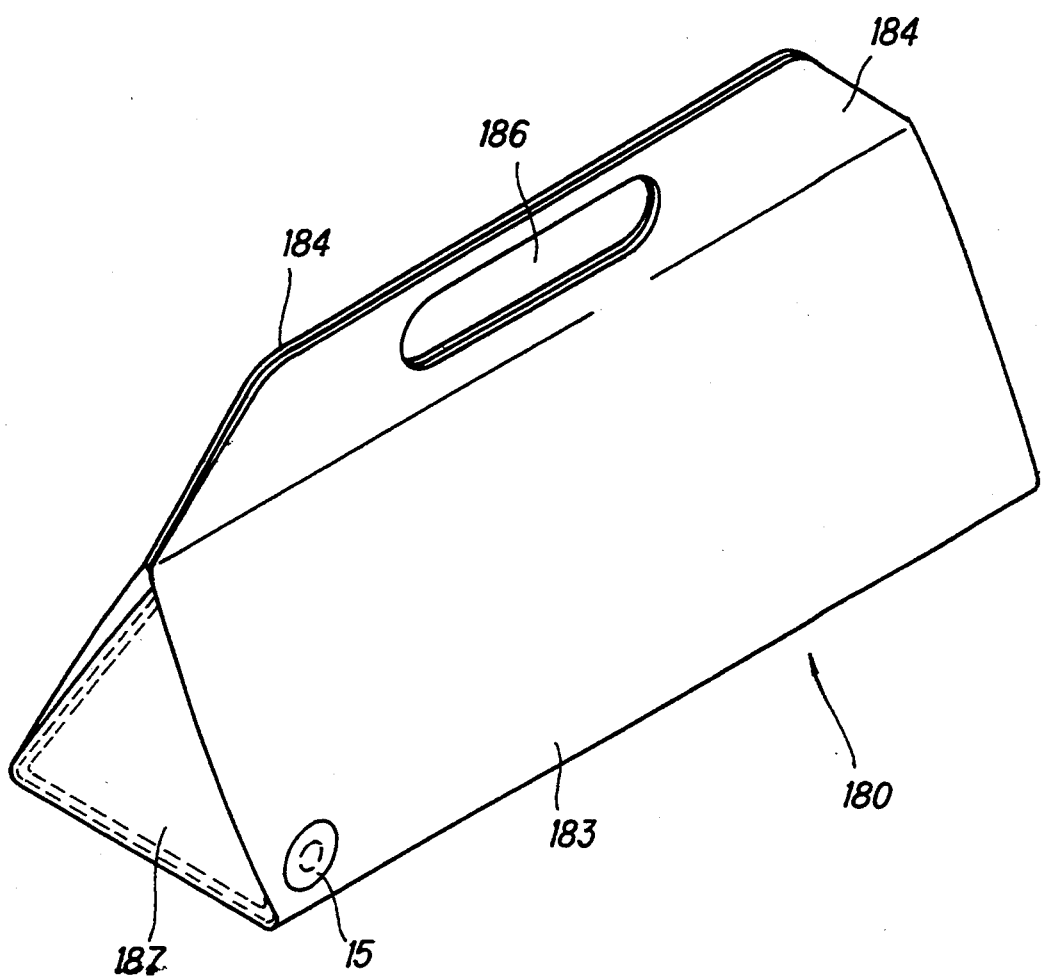
FIG. 56 is a perspective view of the wrapping means of FIG. 55, in use.
Figure 57:
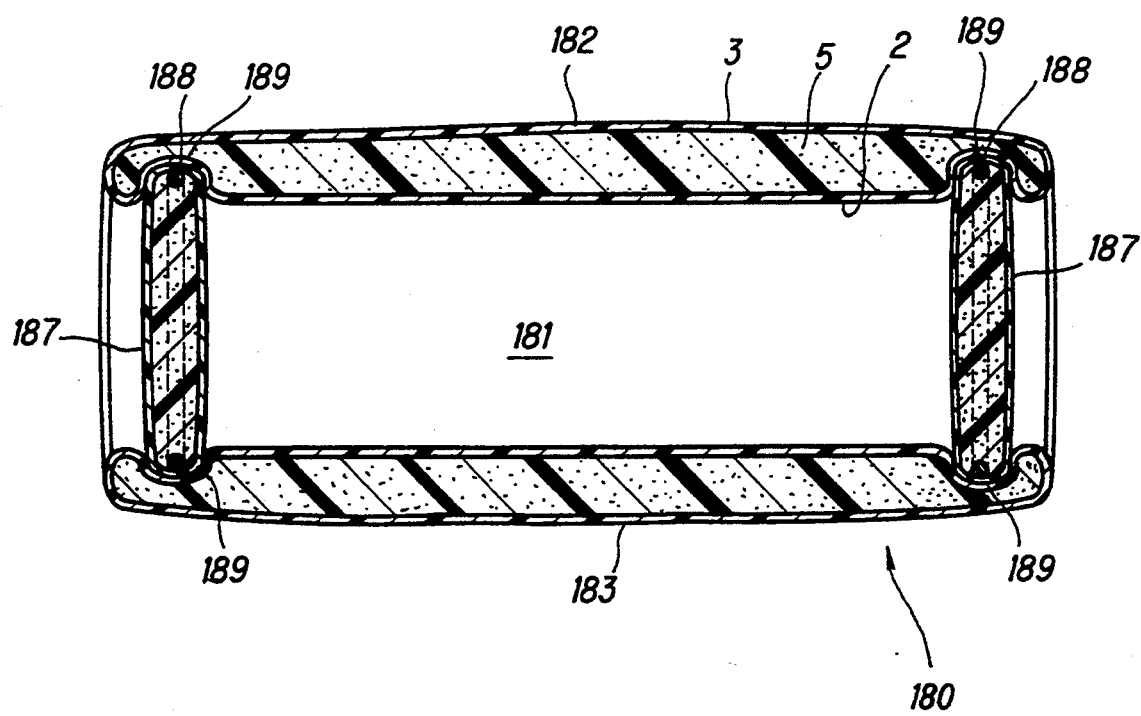
FIG. 57 is a sectional side view of FIG. 55.
Figure 59:
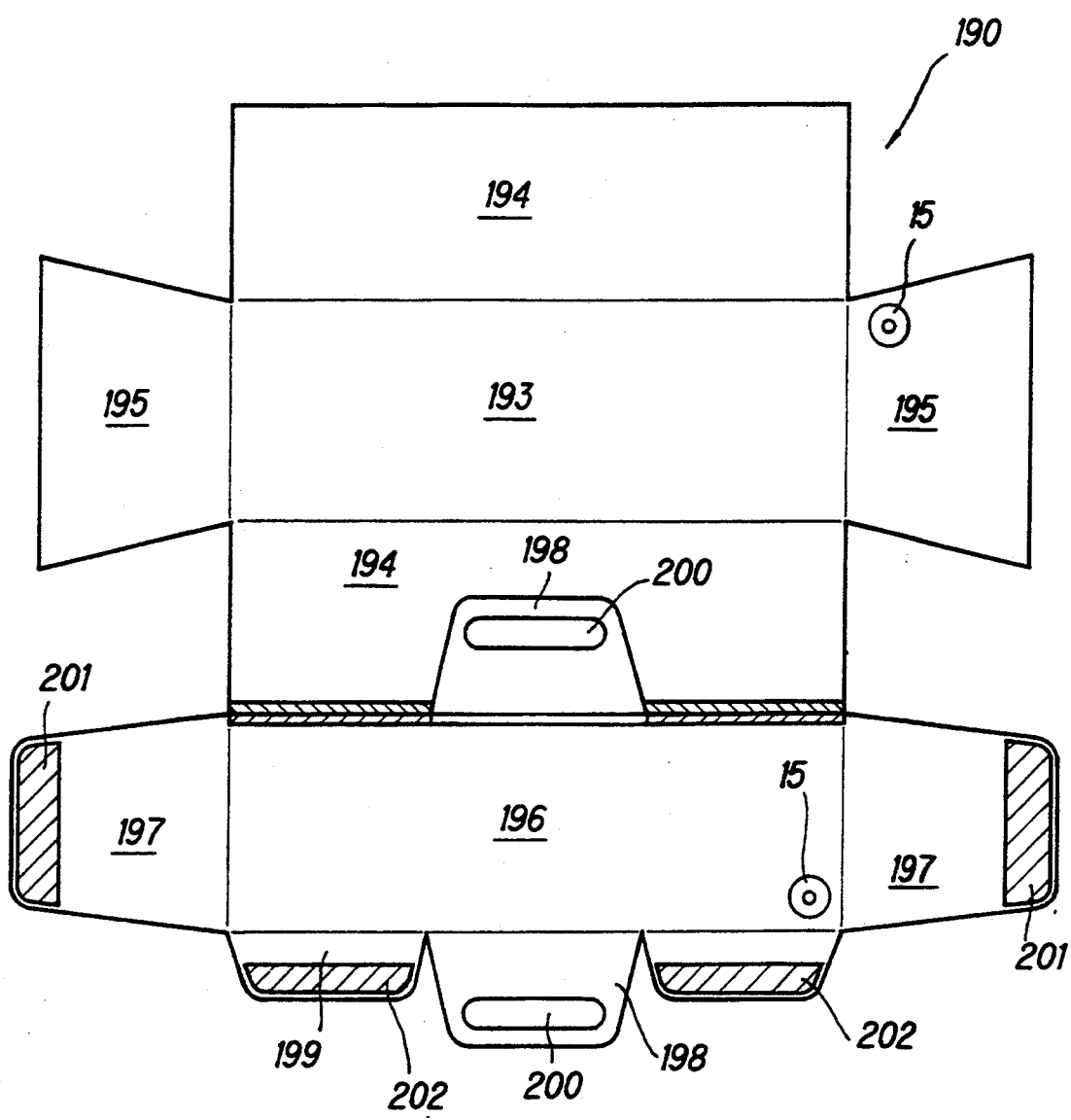
FIG. 59 is an unfolded view of FIG. 58, in its joined state.

FIG. 55 to FIG. 57 show an embodiment in which a sheet-like wrapping body 180 includes a rectangular base sheet 181, side sheets 182 and 183 extending laterally from the base sheet 181 and having cover members 184 with slots 186, and triangular-shaped upper and lower lids 187 extending upward and downward from the base sheet 181. The cover members 184 have respective pressure sensitive adhesives 185. It is preferable to provide the upper and lower lids 187 with triangular frameworks 188.

According to the wrapping means of this embodiment, a wrapping case shaped as a triangle can be produced by raising the upper and lower lids 187 and bending upward the side sheets 182 and 183 so as to put the the lids 187 between the upper and lower edges of the side sheets 182 and 183, as shown in FIG. 57. The wrapping case thus obtained is retained by the pressure sensitive adhesives 185 applied onto the cover members 184 which come into face contact with each other. Since the wrapping case inflates inwardly by introducing air into the wrapping body 180 through the air valve 15, various kinds of articles can be firmly held within the wrapping case.

FIG. 58 to FIG. 61 show an embodiment in which a wrapping body 190 comprises a base sheet 191 and a lid sheet 192 welded to the base sheet 191. The base sheet 191 has a central part 193, upper and lower parts 194 and side parts 195. The lid sheet 192 has a central part 196 and side parts 197. The central part 196 includes a pair of holder pieces 198 each having a slot 200, and cover members 199. It is desirable to apply pressure sensitive adhesives 201 and 202 onto the side parts 197 and the cover members 199.

Figure 60:
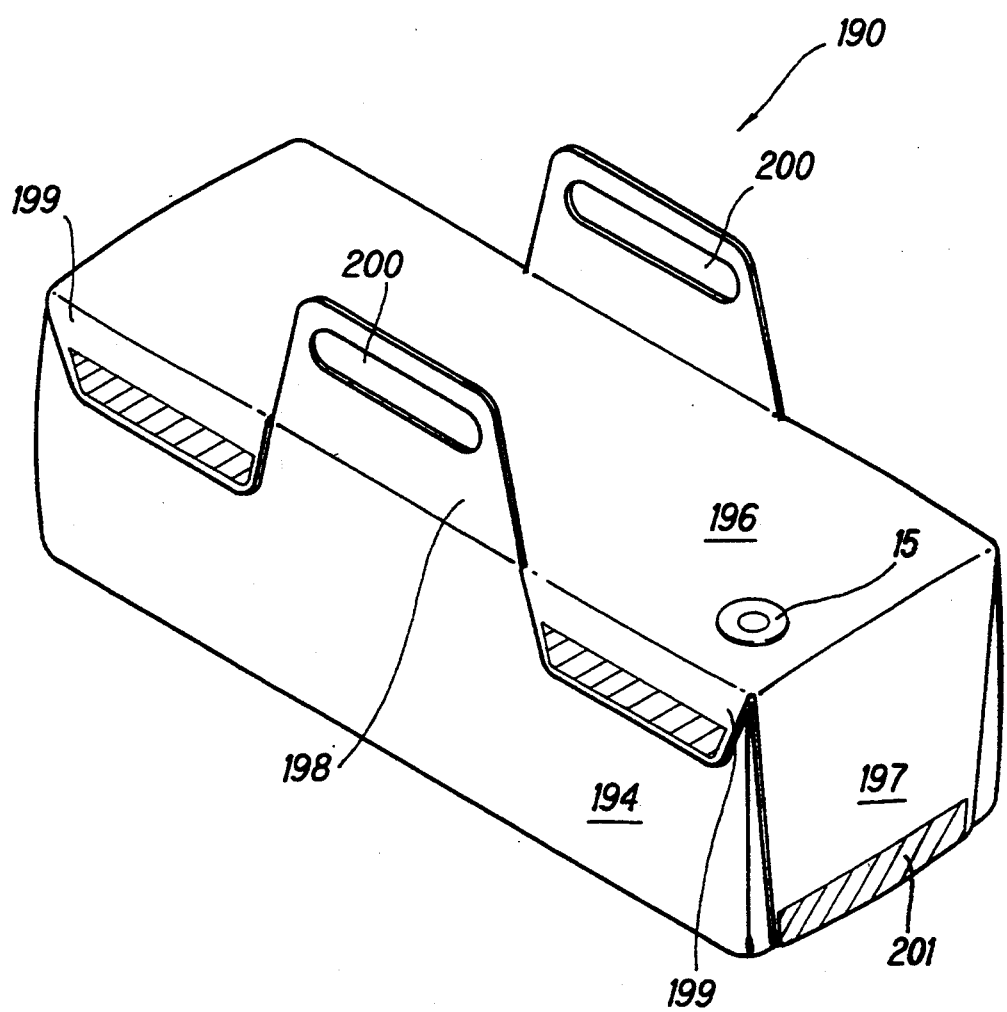
FIG. 60 is a perspective view of FIG. 58, in use.
Figure 61:
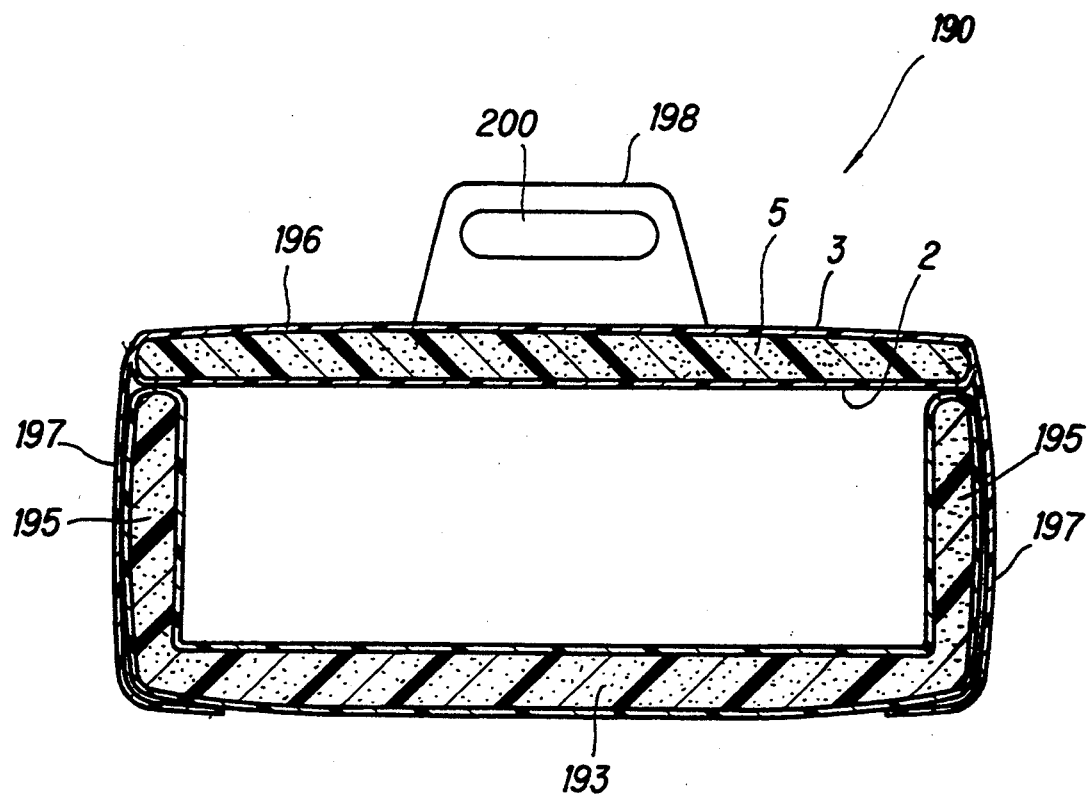
FIG. 61 is a sectional side view of FIG. 58.

The wrapping body 190 is properly folded and firmly fastened by the pressure sensitive adhesives to form a box-like container as shown in FIG. 60. Since the wrapping body 190 can be inflated by introducing air thereinto as shown in FIG. 61, various articles can be tightly held in the box-like container.

Figure 62:
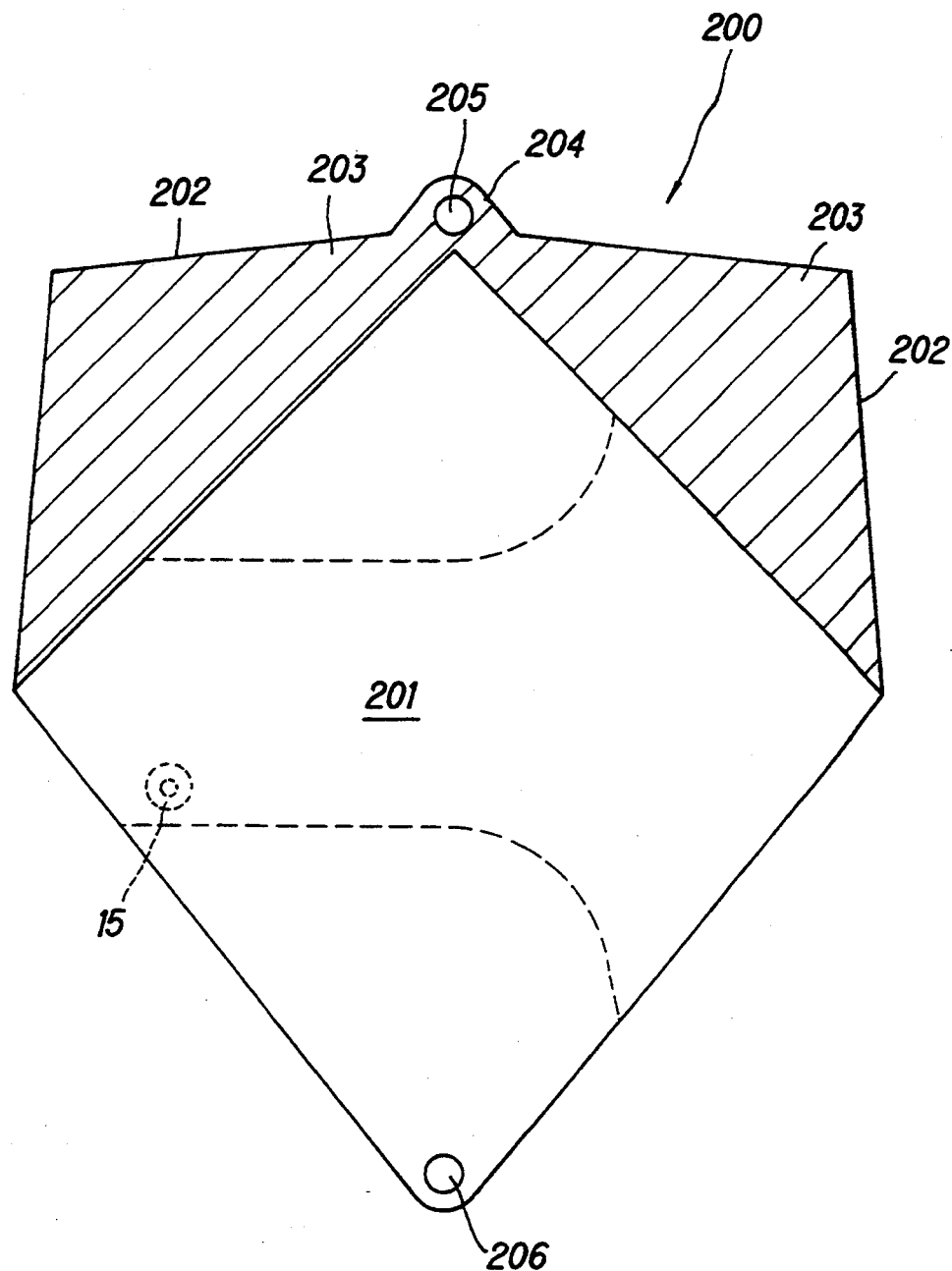
FIG. 62 is an unfolded view of a twenty-first embodiment of the wrapping means of this invention.
Figure 64:
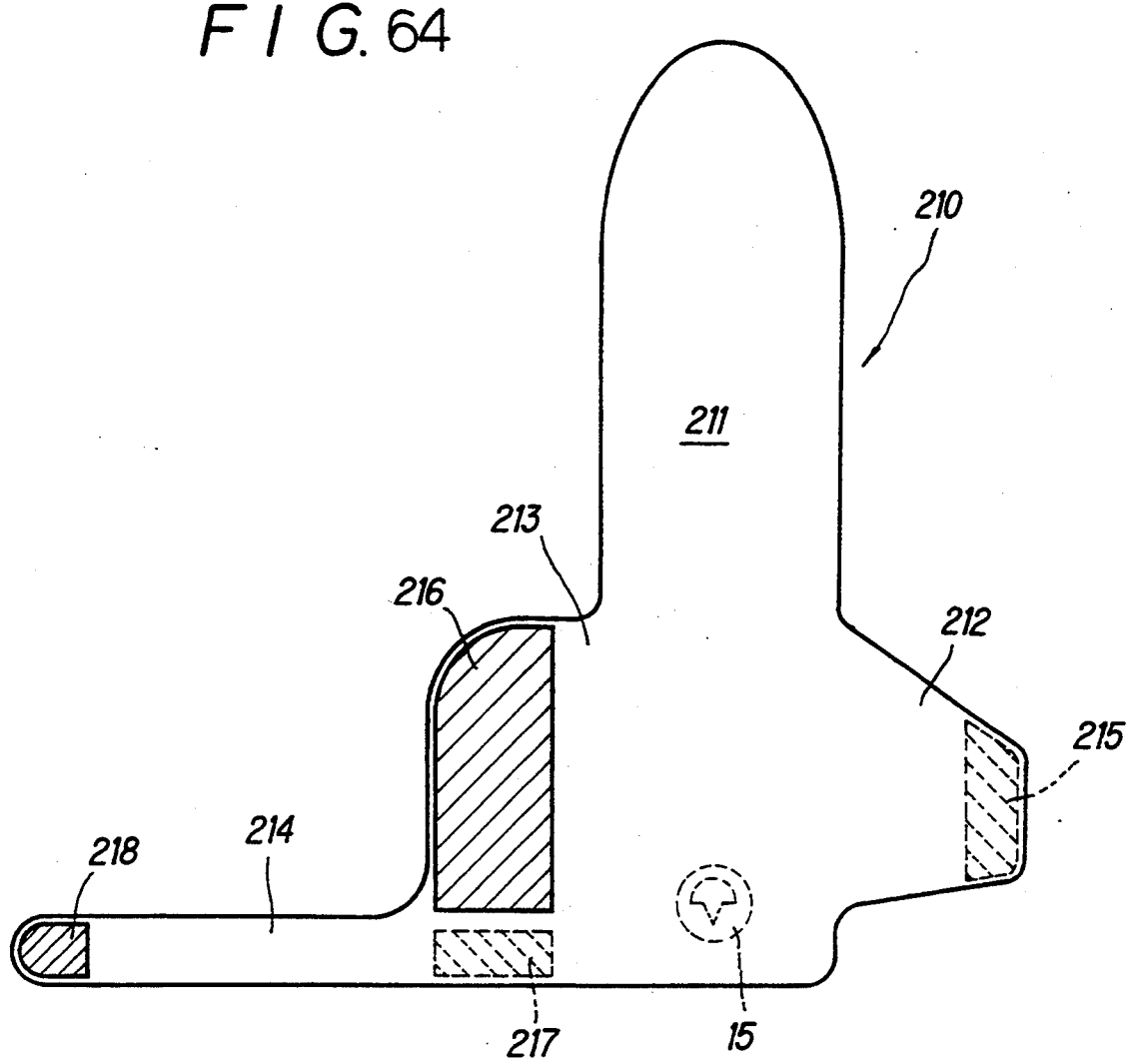
FIG. 64 is a front view of the twenty-second embodiment of the wrapping means of this invention.

FIG. 62 and FIG. 63 show an embodiment in which a sheet-like wrapping body 200 comprises a substantially lozenge-shaped base sheet 201 and cover sheets 202 shaped as triangles extending upward from the base sheet 201 and having pressure sensitive adhesives 203. Between the cover sheets 202, a hook piece 204 with a hole 205 is formed. In the lower portion of the base sheet 201, a hole 206 is bored.

This wrapping means can be used by first folding the base sheet 201 to two so as to bring the holes 205 and 206 into registration with each other, inserting a string 207 through the matching holes 205 and 206, and suspending the string 207 from the neck of a subject person. Then, upon insertion of the arm of the person into the double-folded base sheet 201, the cover sheets 202 are folded to lie on the base sheet 201 as illustrated in FIG. 63. By opening the air valve 15 to introduce air into the inside of the wrapping body 200, the wrapping body 200 inflates to firmly hold the arm.

Thus, the wrapping means of this embodiment can be used as a provisional plaster cast. By making the wrapping body 200 longer, even the upper arm of the person can be supported.

FIG. 64 to FIG. 68 show an embodiment in which a sheet-like wrapping body 210 comprises a base sheet 211 shaped substantially as a finger or projection, and tongue pieces 212 and 213 extending laterally from the lower part of the base sheet 211. The base sheet is generally made sufficiently longer than the finger of a subject person. The tongue piece 213 has a band strip 214. The tongue pieces 212, 213 and band strip 214 are provided with pressure sensitive adhesives 215–218.

Figure 65:
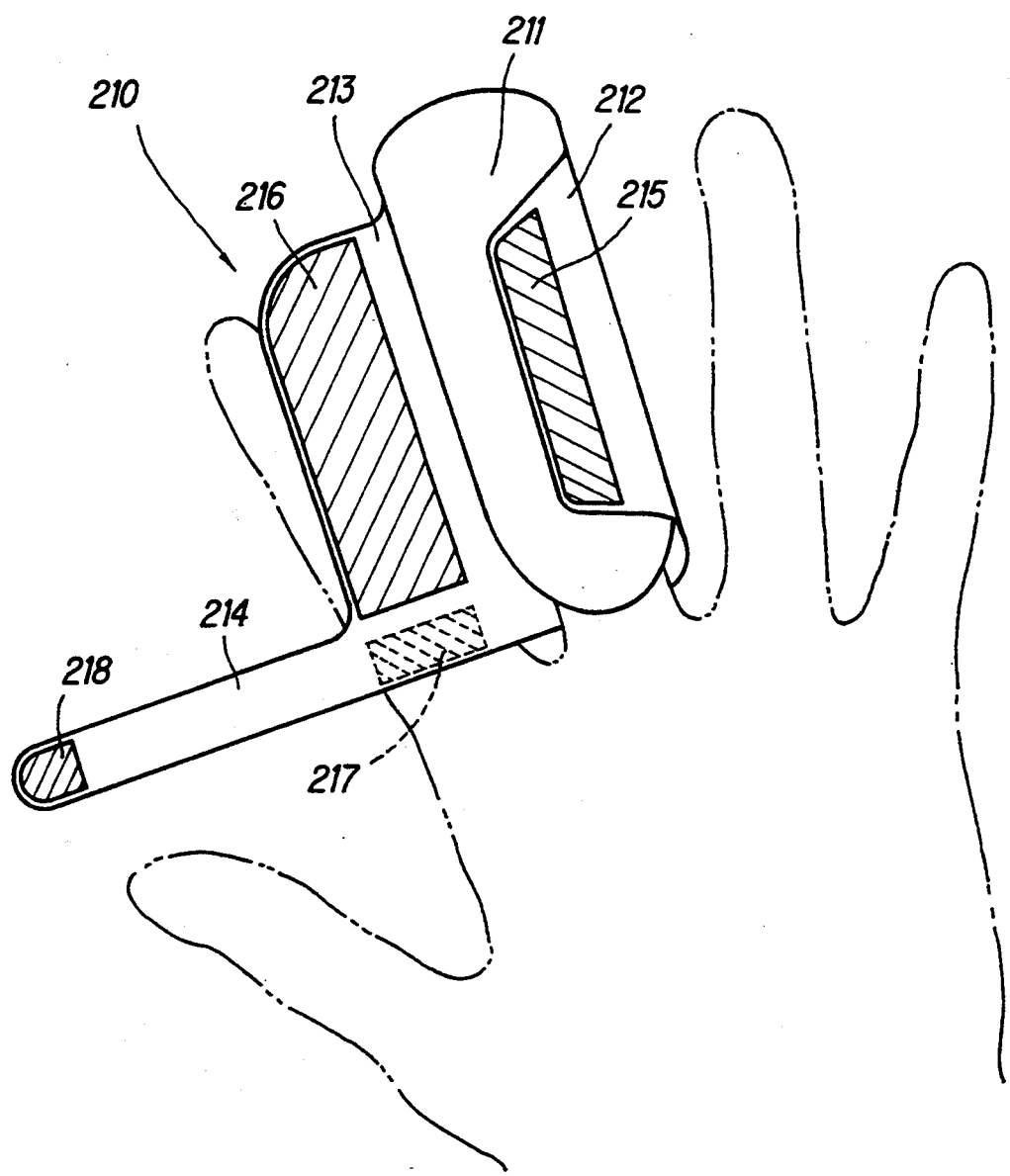
FIG. 65 is an explanatory view showing the process in which a finger is being wrapped with the wrapping means of FIG. 64.
Figure 66:
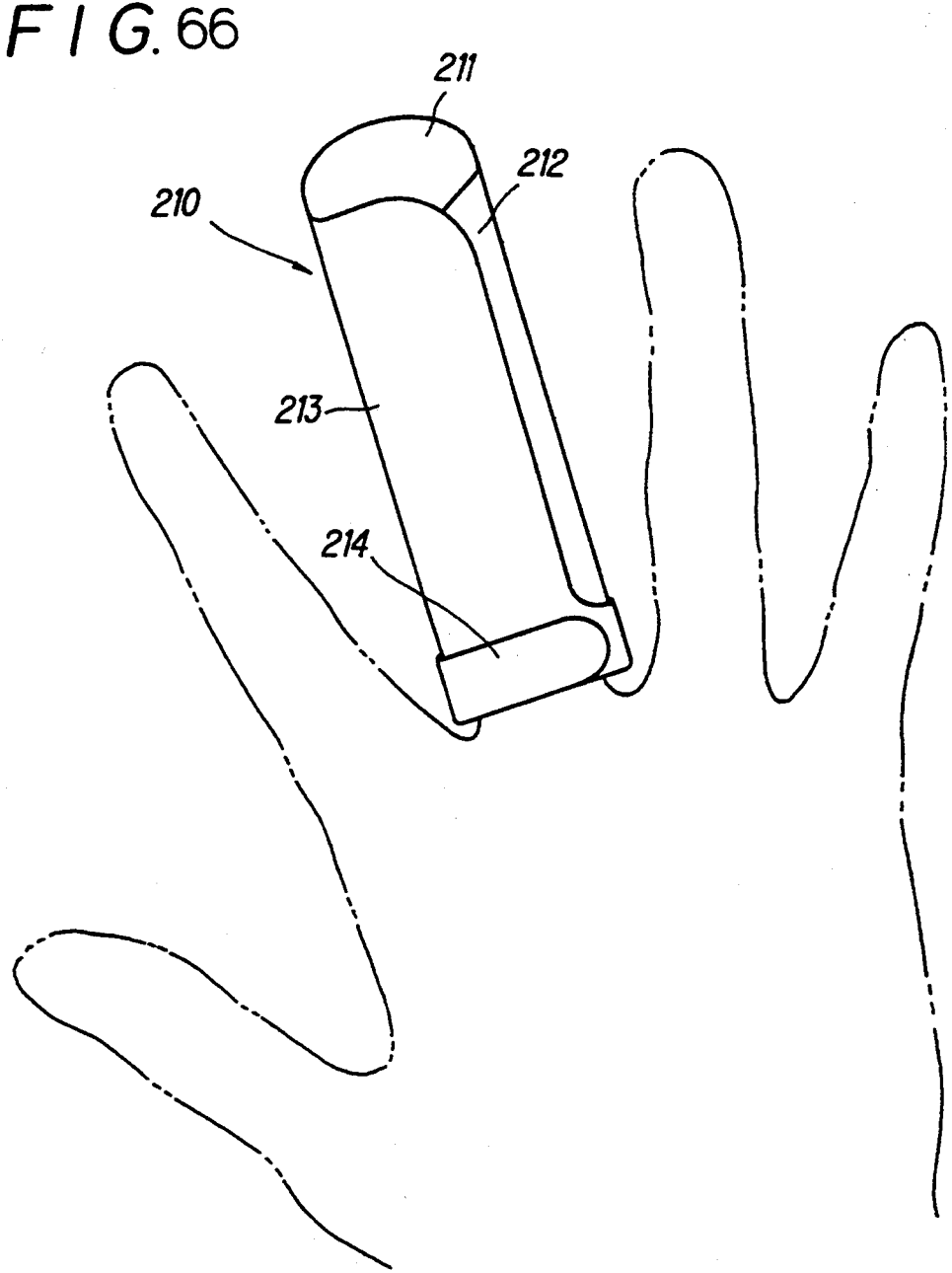
FIG. 66 is a view showing the state in which a finger is wrapped with the wrapping means of FIG. 64.

In use, the finger is first put on the lower half of the base sheet 211, and the upper half of the base sheet 211 is folded in two so as to be placed on the finger. Then, the tongue pieces 212 and 213 are wound round the finger as shown in FIG. 65. Finally, the band strip 214 is wound round the finger as shown in FIG. 66. The wound wrapping means is firmly fastened with the pressure sensitive adhesives.

Figure 67:
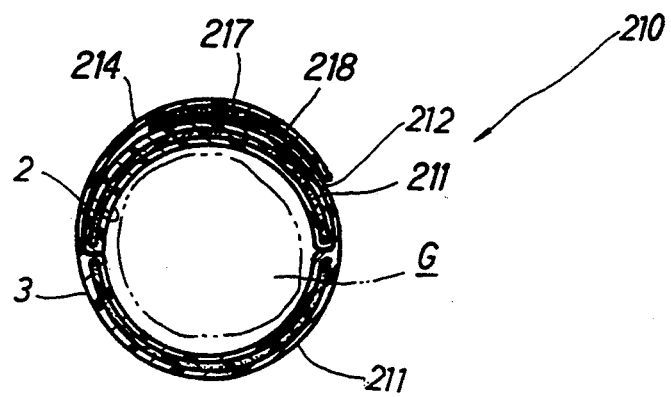
FIG. 67 is a cross-sectional view showing the wrapping means of FIG. 66, in its contracted state.
Figure 68:
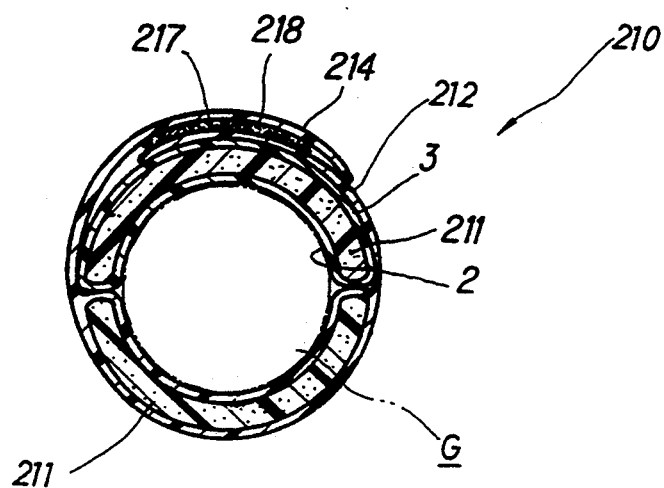
FIG. 68 is a cross-sectional view showing the wrapping means of FIG. 66, in its inflated state.

By introducing air into the wrapping body 210 shown in FIG. 67 to inflate the base sheet 211 as shown in FIG. 68, the finger G is suitably held. The wrapping means of this embodiment can be used as a plaster case for fingers. Instead of the pressure sensitive adhesives 215–218, male and female face fasteners may be used.

Figure 69:
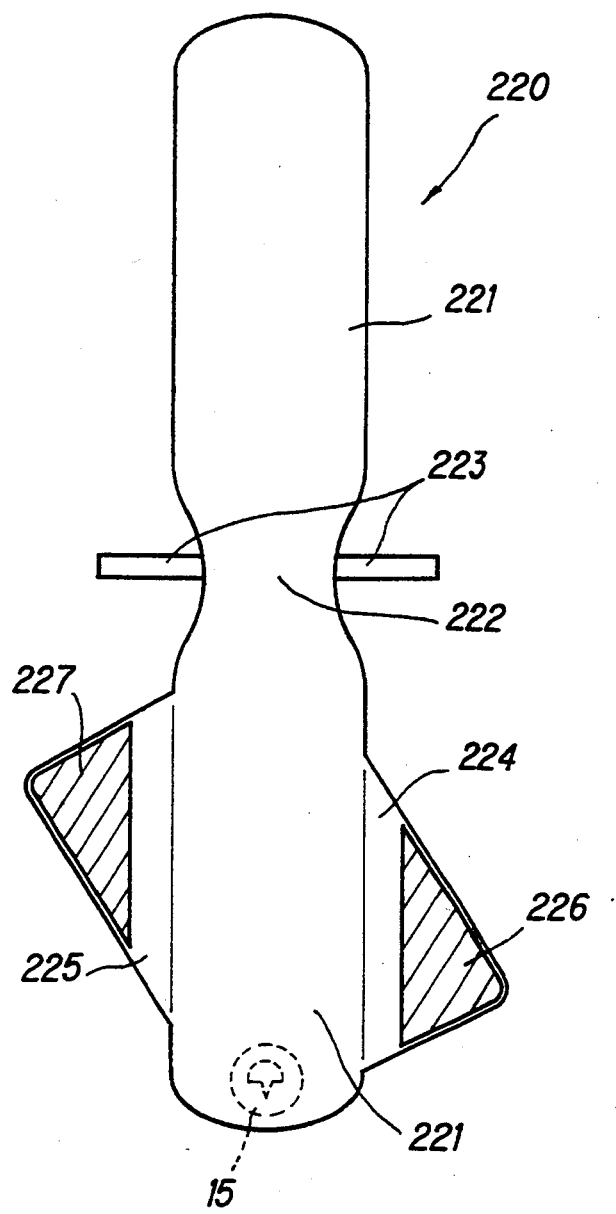
FIG. 69 is an unfolded plan view of a twenty-third embodiment of the wrapping means of this invention.
Figure 70:
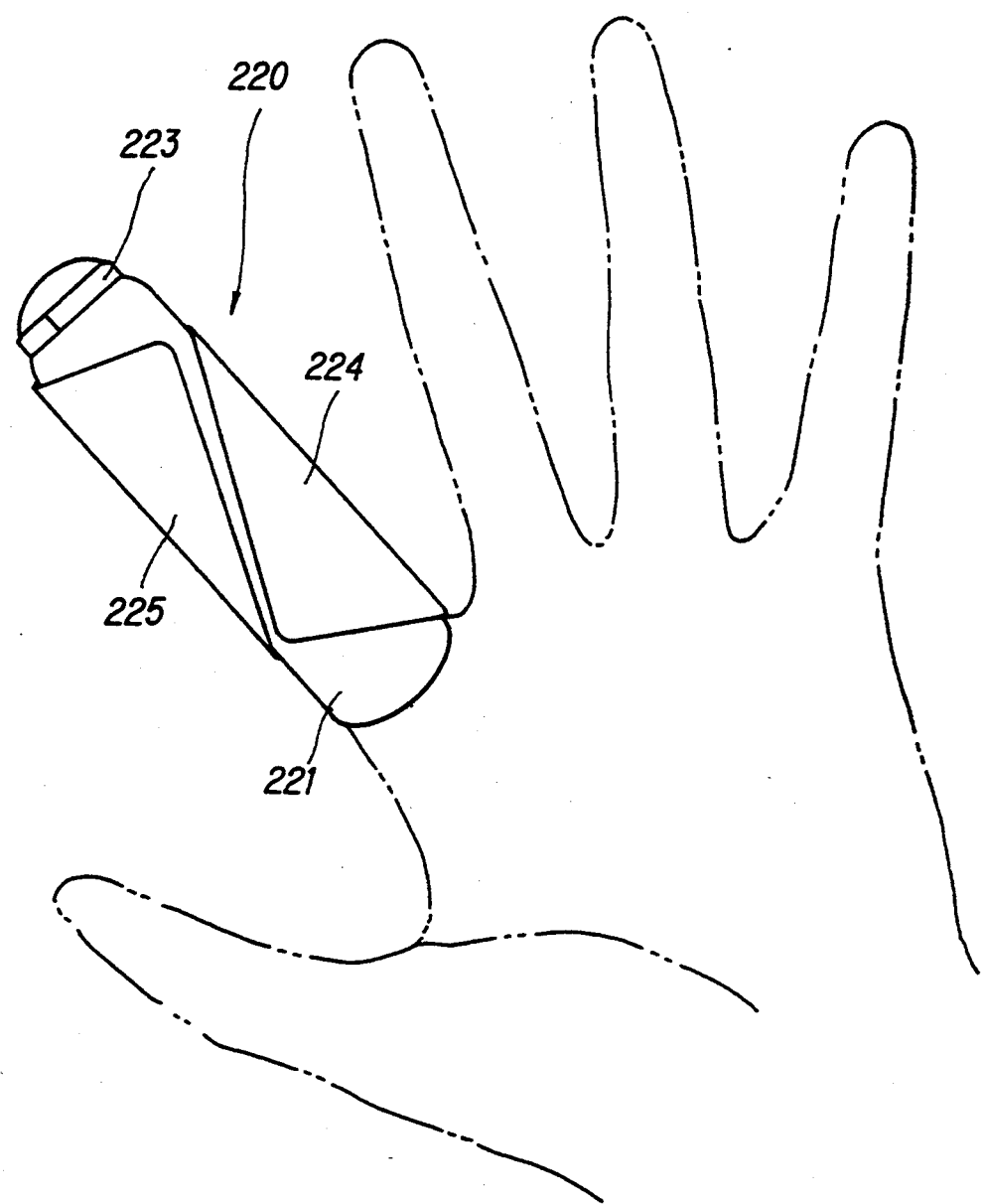
FIG. 70 is a view showing the state in which a finger is wrapped with the wrapping means of FIG. 69.

FIG. 69 and FIG. 70 show an embodiment in which a sheet-like wrapping body 220 comprises a pair of base sheets 221 joined to each other through a constricted part 222, cover sheets 224 and 225 extending laterally from the lower base sheet 221, and a slender string 223 attached to the constricted part 222 between the base sheets. The cover sheets 224 and 225 are provided with pressure sensitive adhesives 226 and 227 and formed so as not to meet each other when being folded on the lower base sheet 221.

The wrapping means of this embodiment can be suitably wound around a finger as shown in FIG. 70. Upon covering the finger with the base sheets 221 and cover sheets 224, the wrapping body 220 is inflated by introducing air into the inside thereof, and then the slender string is tied on the tip of the finger, thus tightly holding the finger.

Figure 71:
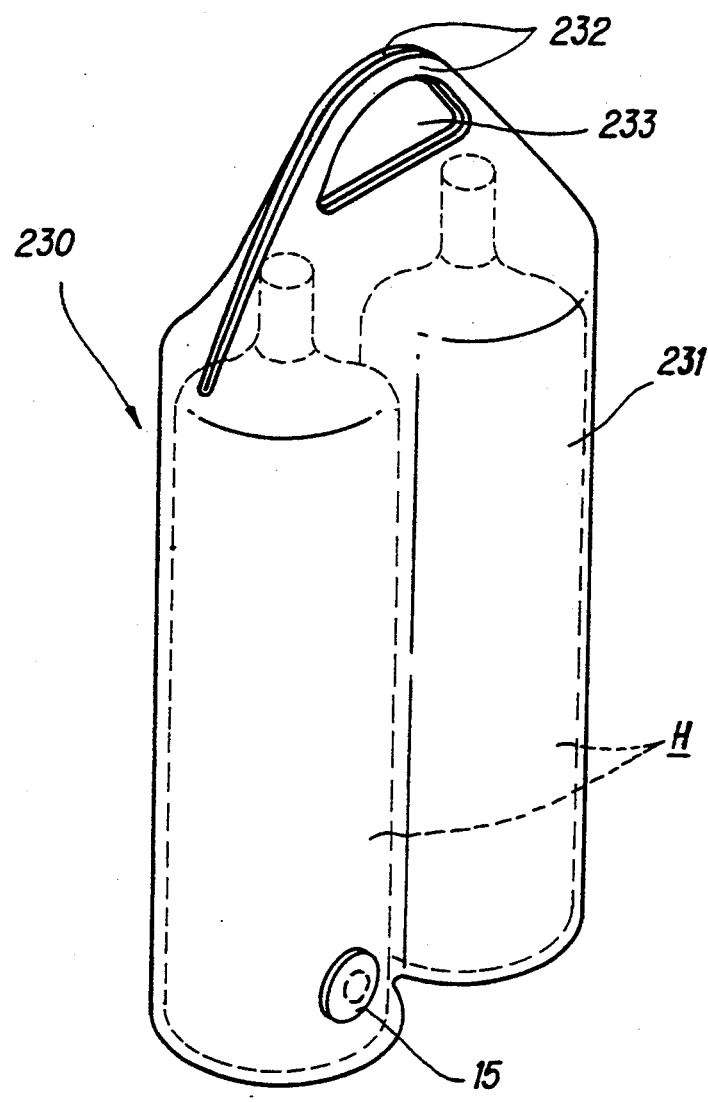
FIG. 71 is a perspective view of a twenty-fourth embodiment of the wrapping means of this invention.

FIG. 71 and FIG. 72 show an embodiment in which a sheet-like wrapping body 230 comprises a base sheet 231 having a generally rectangular shape, and cover sheets 232 with holding holes 233. According to this embodiment, bottles H can be securely held in the wrapping body so as to be carried easily.

Only one bottle can be securely held by the wrapping means of the embodiment shown in FIG. 73.

As is apparent from the foregoing, according to the wrapping means of this invention, given articles of various kinds can be securely wrapped with a sheet-like wrapping body irrespective of the shape and size of the article to be wrapped and effectively protected from any shocks. Furthermore, shocks which are possibly produced due to collision of the given articles to be wrapped can be remarkably alleviated by inserting the articles into independent pockets formed in the wrapping means of this invention.

Since the sheet-like wrapping body of this invention is made of a flexible membrane, articles of any shape and size can be easily wrapped with the wrapping body. In addition, since the engaging members and air valve disposed on the wrapping body are of simple structure, the wrapping means of this invention can be reused and is easy to handle. Thus, the efficiency of wrapping and carrying the given article can be remarkably improved.

Since the sheet-like wrapping body of this invention is basically made of sponge foaming resin and resilient plastic sheet material having gas barrier properties, it is possible to mass produce the wrapping means of this invention at a low cost by synthetic resin processing techniques.

Moreover, the wrapping means according to this invention can be used not only for wrapping articles of various kinds, but also protecting an injured portion of a living body from external physical shocks as a medical appliance.

Although the invention has been described in its preferred form with a certain degree of particularity, it is understood that the present disclosure of the preferred form can be changed in the details of construction, and the changes of combination and arrangement of parts may be resorted to without departing from the spirit and the scope of the invention as hereinafter claimed.

I claim:

1. A wrapping system comprising:
   a sheet-like wrapping body formed of first and second flexible membranes having gas barrier properties and joined in a two-ply state to define therebetween an air tight cavity, and a sheet-like foam cushion material positioned in a compressed state thereof in said cavity between said flexible membranes; and
   an air valve disposed on one of said flexible membranes to selectively introduce air into said cavity to cause said cushion material to expand from said compressed state, said air valve comprising a sealing member positioned on said one flexible membrane, said sealing member having a part forming a cutter to cut a vent hole in said one flexible membrane, after which said sealing member seals said vent hole.

2. A wrapping system as claimed in claim 1, further comprising engaging members on said flexible membranes to maintain said wrapping body in a wrapped state about an article to be wrapped.

3. A wrapping system as claimed in claim 2, wherein said engaging members comprise female and male fasteners.

4. A wrapping system as claimed in claim 2, wherein said engaging members comprise pressure sensitive adhesive.

5. A wrapping system as claimed in claim 2, wherein said engaging members form at least one slide fastener.

6. A wrapping system as claimed in claim 1, wherein at least a first said flexible membrane has thereon an article receiving pocket.

7. A wrapping system comprising:
   a sheet-like wrapping body formed of first and second flexible membranes having gas barrier properties and joined in a two-ply state to define therebetween an air tight cavity, and a sheet-like foam cushion material positioned in a compressed state thereof in said cavity between said flexible membranes; and an air valve disposed on one of said flexible membranes to selectively introduce air into said cavity to cause said cushion material to expand from said compressed state, said air valve comprising a sealing membrane positioned on said one flexible membrane, said sealing member having a pointed blade positioned such that pulling of said sealing member from said one flexible membrane automatically sticks said pointed blade into said one flexible membrane to thereby form a vent hole therein, after which said sealing member seals said vent hole.

8. A wrapping system as claimed in claim 7, further comprising engaging members on said flexible membranes to maintain said wrapping body in a wrapped state about an article to be wrapped.

9. A wrapping system as claimed in claim 8, wherein said engaging members comprise female and male fasteners.

10. A wrapping system as claimed in claim 8, wherein said engaging members comprise pressure sensitive adhesive.

11. A wrapping system as claimed in claim 8, wherein said engaging members form at least one slide fastener.

12. A wrapping system as claimed in claim 7, wherein at least a first said flexible membrane has thereon an article receiving pocket.

13. A wrapping system comprising:
a sheet-like wrapping body formed of first and second flexible membranes having gas barrier properties and joined in a two-ply state to define therebetween an air tight cavity, and a sheet-like foam cushion material positioned in a compressed state thereof in said cavity between said flexible membranes; and
an air valve disposed on one of said flexible membranes to selectively introduce air into said cavity to cause said cushion material to expand from said compressed state, said air valve comprising a slide plate disposed slidably between two plates having aligned vent openings, said slide plate having a cutter elastically urged toward said one flexible membrane and operable, by sliding said slide plate to align with said vent openings, snap through one said vent opening into said one flexible membrane to thereby form a vent hole therein.

14. A wrapping system as claimed in claim 13, further comprising engaging members on said flexible membrane to maintain said wrapping body in a wrapped state about an article to be wrapped.

15. A wrapping system as claimed in claim 14, wherein said engaging members comprise female and male fasteners.

16. A wrapping system as claimed in claim 14, wherein said engaging members comprise pressure sensitive adhesive.

17. A wrapping system as claimed in claim 14, wherein said engaging members form at least one slide fastener.

18. A wrapping system as claimed in claim 13, wherein at least a first said flexible membrane has thereon an article receiving pocket.

* * * * *